(12) United States Patent
Howard et al.

(10) Patent No.: US 8,633,185 B2
(45) Date of Patent: Jan. 21, 2014

(54) PYRROLOBENZODIAZEPINES

(75) Inventors: Philip Wilson Howard, London (GB); Zhizhi Chen, London (GB); Stephen John Gregson, London (GB)

(73) Assignee: Spirogen Sarl, St-Legier-La Chiesaz (CH)

( * ) Notice: Subject to any disclaimer, the term of this patent is extended or adjusted under 35 U.S.C. 154(b) by 861 days.

(21) Appl. No.: 12/610,478

(22) Filed: Nov. 2, 2009

(65) Prior Publication Data

US 2010/0113425 A1    May 6, 2010

Related U.S. Application Data

(63) Continuation of application No. 11/911,890, filed as application No. PCT/GB2006/001456 on Apr. 21, 2006, now Pat. No. 7,612,062.

(30) Foreign Application Priority Data

Apr. 21, 2005 (GB) .................................. 0508084.1
Nov. 7, 2005 (GB) .................................. 0522746.7

(51) Int. Cl.
C07D 519/00 (2006.01)
A61K 31/5517 (2006.01)
A61P 35/00 (2006.01)

(52) U.S. Cl.
USPC .......................................... 514/220; 540/496

(58) Field of Classification Search
USPC .......................................... 514/220; 540/496
See application file for complete search history.

(56) References Cited

U.S. PATENT DOCUMENTS

| | | | |
|---|---|---|---|
| 4,309,437 A | 1/1982 | Ueda et al. | |
| 5,418,241 A | 5/1995 | Jegham et al. | |
| 6,187,797 B1 | 2/2001 | Pruitt et al. | |
| 6,562,806 B1 | 5/2003 | Thurston et al. | |
| 6,608,192 B1 | 8/2003 | Thurston et al. | |
| 6,660,856 B2 | 12/2003 | Wang | |
| 6,747,144 B1 | 6/2004 | Thurston et al. | |
| 6,909,006 B1 | 6/2005 | Thurston et al. | |
| 7,049,311 B1 | 5/2006 | Thurston et al. | |
| 7,067,511 B2 | 6/2006 | Thurston et al. | |
| 7,265,105 B2 | 9/2007 | Thurston et al. | |
| 7,407,951 B2 | 8/2008 | Thurston et al. | |
| 7,429,658 B2 | 9/2008 | Howard et al. | |
| 7,528,126 B2 | 5/2009 | Howard et al. | |
| 7,557,099 B2 | 7/2009 | Howard et al. | |
| 7,612,062 B2 | 11/2009 | Howard et al. | |
| 2003/0195196 A1 | 10/2003 | Thurston et al. | |
| 2004/0092736 A1 | 5/2004 | Thurston et al. | |
| 2004/0138269 A1 | 7/2004 | Sun et al. | |
| 2004/0198722 A1 | 10/2004 | Thurston et al. | |
| 2007/0072846 A1 | 3/2007 | Vishnuvajjala et al. | |
| 2007/0173497 A1 | 7/2007 | Howard et al. | |
| 2007/0191349 A1 | 8/2007 | Howard et al. | |
| 2007/0249591 A1 | 10/2007 | Howard et al. | |
| 2008/0090812 A1 | 4/2008 | Pepper et al. | |
| 2008/0214525 A1 | 9/2008 | Howard et al. | |

FOREIGN PATENT DOCUMENTS

| | | |
|---|---|---|
| EP | 1193270 | 4/2002 |
| GB | 2053894 | 2/1981 |
| JP | 55069587 | 5/1980 |
| JP | 58180487 | 10/1983 |
| WO | 93/18045 | 9/1993 |
| WO | 00/12506 | 3/2000 |
| WO | 00/12507 | 3/2000 |
| WO | 00/12508 | 3/2000 |
| WO | 00/12509 | 3/2000 |
| WO | WO 2004/043963 | 5/2004 |
| WO | WO 2005/023814 | 3/2005 |
| WO | WO 2005/040170 | 5/2005 |
| WO | WO 2005/042535 | 5/2005 |
| WO | WO 2005/085250 | 9/2005 |

(Continued)

OTHER PUBLICATIONS

Althius, T. H. and Hess, H. J., "Synthesis and Identification of the Major Metabolites of Prazosin Formed in Dog and Rat," J. Medicinal Chem. (1977) 20(1):146-148.

(Continued)

Primary Examiner — Bruck Kifle
(74) Attorney, Agent, or Firm — Michael Best & Friedrich LLP

(57) ABSTRACT

Compounds of the formula I:

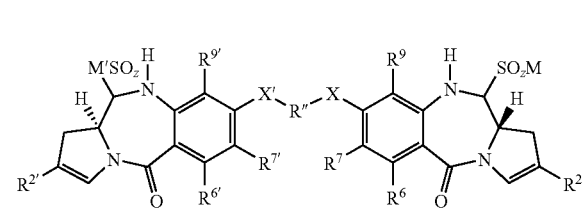

or solvate thereof, wherein:
$R^2$ is an optionally substituted $C_{5-20}$ aryl group;
$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;
$R^7$ is selected from H, R, OH, OR, SH, SR, $NH_2$, NHR, NHRR', nitro, $Me_3Sn$ and halo;
R" is a $C_{3-12}$ alkylene group, which chain may be interrupted by one or more heteroatoms and/or aromatic rings;
X is selected from O, S, or NH;
z is 2 or 3;
M is a monovalent pharmaceutically acceptable cation;
$R^{2'}$, $R^{6'}$, $R^{7'}$, $R^{9'}$, X' and M' are selected from the same groups as $R^2$, $R^6$, $R^7$, $R^9$, X and M respectively, or M and M' may together represent a divalent pharmaceutically acceptable cation.

3 Claims, 2 Drawing Sheets

(56) References Cited

FOREIGN PATENT DOCUMENTS

| WO | WO 2005/085251 | 9/2005 |
|---|---|---|
| WO | WO 2005/085259 | 9/2005 |
| WO | WO 2005/085260 | 9/2005 |
| WO | WO 2005/110423 | 11/2005 |

OTHER PUBLICATIONS

Arima et al., "Studies on Tomaymycin, a New Antibiotic. I. Isolation and Properties of Tomaymycin," J. Antibiotics (1972) 25:437-444.

Berge et al., "Pharmaceutical Salts," J. Pharm. Sci. (1977) 66:1-19.

Bose et al., "New Approaches to Pyrrolo[2,1-c][1,4]benzodiazepines: Synthesis, DNA-binding and cytotoxicity of DC-81," Tetrahedron, 48, 751-758 (1992).

Farmer, J.D. et al., "Synthesis and DNA crosslinking ability of a dimeric anthramycin analog," Tetrahedron Letters (1988) 29(40):5105-5108, Abstract only.

Gregson, S. et al., "Synthesis of a novel C2/C2'-exo unsaturated pyrrolobenzodiazepine cross-linking agent with remarkable DNA binding affinity and cytotoxicity," Chemical Communications, 797-798 (1999).

Hara et al., "DC 102, a new glycosidic pyrrolo(1,4)benzodiazepine antibiotic produced by streptomyces sp.", J. Antibiotics, 41, 702-704 (1988).

Hochlowski, J. et al., "Abbeymycin, a new anthramycin-type antibiotic produced by a streptomycete," J. Antibiotics, 40, 145-148 (1987).

Howard, P.W. et al., "Design, synthesis and biological evaluation of ZC-423, a novel C2-aryl substituted pyrrolobenzodiazepine (PBD) dimer," Clinical Cancer Research (2005) 11(23):90155-90165 (A205).

Howard, P.W. et al., "The design, synthesis and biological evaluation of a set of C2-aryl substituted pyrrolo[2,1-c][1,4]benzodiazepine dimers," EJC Supplements (2006) 4(12):95—Poster Abstract 301.

Hurley, L. and Needham-Vandevanter, D., "Covalent Binding of Antitumor Antibiotics in the Minor Groove of DNA. Mechanism of Action of CC-1065 and the Pyrrolo(1,4)benzodiazepines," Acc. Chem. Res., 19, 230-237 (1986).

Itoh et al., "Sibanomicin, a new pyrrolo(1,4)benzodiazepine antitumor antibiotic produced by a micromonospora sp." J. Antibiotics, 41, 1281-1284 (1988).

Kamal, A. et al., "Design, synthesis and evaluation of new noncrosslinking pyrrolobenzodiazepine dimers with efficient DNA binding ability and potent antitumor activity," J. Med. Chem. (2002) 45:4679-4688.

Kaneko, T. et al., "Bicyclic and tricyclic analogues of anthramycin," J. Med. Chem. (1985) 28:388-392.

Kohn, K., "Anthramycin," Antibiotics III, Springer-Verlag, NY, 3-11 (1975).

Konishi, M. et al., "Chicamycin, a new antitumor antibiotic II. Structure determination of chicamycins A and B," J. Antibiotics, 37, 200-206 (1984).

Kunimoto et al., "Mazethramycin, a new member of anthramycin group antibiotics," J. Antibiotics, 33, 665-667 (1980).

Langley, D.R. and Thurston, D.E., "A versatile and efficient synthesis of carbinolamine-containing pyrrolo[1,4]benzodiazepines via the cyclization of N-92-aminobenzoyl)pyrrolidine-2-carboxaldehyde diethyl thioacetals: total synthesis of prothracarcin," J. Org. Chem., 52, 91-97 (1987).

Langlois, N. et al., "Synthesis and cytotoxicity on sensitive and doxorubicin-resistant cell lines of new pyrrolo[2,1-c][1,4]benzodiazepines related to anthramycin," J. Med. Chem. (2001) 44:3754-3757.

Leber, J.D. et al., "A revised structure for sibiromycin," J. Am. Chem. Soc., 110, 2992-2993 (1988).

Leimgruber, W. et al., "Isolation and characterization of anthramycin, a new antitumor antibiotic," J. Am. Chem. Soc., 87, 5791-5793 (1965).

Leimgruber, W. et al., "The structure of anthramycin," J. Am. Chem. Soc., 87, 5793-5795 (1965).

Shimizu, K et al., "Prothracarcin, a Novel Antitumor Antibiotic," J. Antibiotics, 35, 972-978 (1982).

Takeuchi, T. et al., "Neothramycins A and B, New Antitumor Antibiotics," J. Antibiotics, 29, 93-96 (1976).

Thurston, D.E. and Bose, D.S., "Synthesis of DNA-Interactive Pyrrolo[2,1-c][1,4]benzodiazepines," Chem. Rev., 94:433-465 (1994).

Thurston, D.E. and Thompson, A.S., "The molecular recognition of DNA," Chem. Brit., 26, 767-772 (1990).

Tsunakawa, M. et al., "Porothramycin, a new antibiotic of the anthramycin group: Production, isolation, structure and biological activity," J. Antibiotics, 41:1366-1373 (1988).

Umezawa, H. et al., Chemical Abstract No. 4427a, "Mazethramycins" Chemical Abstracts, vol. 90, No. 1, 428 (1979).

Weidner-Wells, M.A. et al., "Photochemical approach to the synthesis of the pyrrolo[1,4]benzodiazepine antibiotics," J. Org. Chem. (1989) 54:5746-5758.

Workman, P. et al., "United Kingdom Co-ordinating Committee on Cancer Research (UKCCCR) guidelines for the welfare of animals in experimental neoplasia (second edition)," Br. J. Cancer (1998) 77(1):1-10.

United States Office Action for U.S. Appl. No. 09/763,813 dated Sep. 10, 2002 (11 pages).

United States Office Action for U.S. Appl. No. 09/763,813 dated Feb. 28, 2003 (8 pages).

United States Office Action for U.S. Appl. No. 09/763,813 dated May 21, 2003 (7 pages).

United States Office Action for U.S. Appl. No. 09/763,767 dated May 23, 2002 (20 pages).

United States Office Action for U.S. Appl. No. 09/763,767 dated Nov. 15, 2002 (19 pages).

United States Office Action for U.S. Appl. No. 09/763,767 dated May 20, 2003 (11 pages).

United States Office Action for U.S. Appl. No. 09/763,767 dated Jan. 14, 2004 (11 pages).

United States Office Action for U.S. Appl. No. 09/763,767 dated Aug. 4, 2004 (7 pages).

United States Office Action for U.S. Appl. No. 09/763,767 dated Jun. 9, 2005 (5 pages).

United States Office Action for U.S. Appl. No. 11/367,241 dated Jun. 22, 2006 (11 pages).

United States Office Action for U.S. Appl. No. 11/367,241 dated Nov. 24, 2006 (16 pages).

United States Office Action for U.S. Appl. No. 09/763,814 dated Sep. 13, 2001 (16 pages).

United States Office Action for U.S. Appl. No. 09/763,814 dated Apr. 23, 2002 (23 pages).

United States Office Action for U.S. Appl. No. 09/763,814 dated Jul. 24, 2002 (8 pages).

United States Office Action for U.S. Appl. No. 09/763,814 dated Sep. 23, 2002 (8 pages).

United States Office Action for U.S. Appl. No. 09/673,768 dated Dec. 14, 2001 (7 pages).

United States Office Action for U.S. Appl. No. 09/673,768 dated Jul. 12, 2002 (4 pages).

United States Office Action for U.S. Appl. No. 09/673,768 dated Dec. 24, 2002 (4 pages).

United States Office Action for U.S. Appl. No. 10/021,213 dated May 20, 2003 (10 pages).

United States Office Action for U.S. Appl. No. 10/379,049 dated Mar. 21, 2005 (14 pages).

United States Office Action for U.S. Appl. No. 10/379,049 dated Oct. 5, 2005 (17 pages).

United States Office Action for U.S. Appl. No. 10/379,049 dated Apr. 26, 2006 (9 pages).

United States Office Action for U.S. Appl. No. 10/602,521 dated Sep. 24, 2007 (12 pages).

United States Office Action for U.S. Appl. No. 10/602,521 dated Mar. 26, 2008 (8 pages).

United States Office Action for U.S. Appl. No. 10/602,521 dated May 31, 2008 (8 pages).

United States Office Action for U.S. Appl. No. 10/602,521 dated Jul. 15, 2008 (7 pages).

(56) References Cited

OTHER PUBLICATIONS

United States Office Action for U.S. Appl. No. 10/602,521 dated Dec. 10, 2008 (12 pages).
United States Office Action for U.S. Appl. No. 10/824,743 dated Jul. 31, 2006 (6 pages).
United States Office Action for U.S. Appl. No. 10/824,743 dated Jan. 17, 2007 (15 pages).
United States Office Action for U.S. Appl. No. 10/824,743 dated Oct. 9, 2007 (12 pages).
United States Office Action for U.S. Appl. No. 10/534,825 dated Sep. 7, 2006 (7 pages).
United States Office Action for U.S. Appl. No. 10/534,825 dated Mar. 2, 2007 (7 pages).
United States Office Action for U.S. Appl. No. 10/571,274 dated Oct. 31, 2007 (6 pages).
United States Office Action for U.S. Appl. No. 10/598,470 dated May 23, 2008 (6 pages).
United States Office Action for U.S. Appl. No. 10/598,482 dated May 22, 2008 (9 pages).
United States Office Action for U.S. Appl. No. 10/598,482 dated Nov. 24, 2008 (6 pages).
United States Office Action for U.S. Appl. No. 10/598,691 dated Mar. 21, 2008 (7 pages).
United States Office Action for U.S. Appl. No. 11/569,007 dated Oct. 15, 2008 (12 pages).
United States Office Action for U.S. Appl. No. 10/598,518 dated Mar. 13, 2009 (7 pages).
Dupont, C. et al., "Synthesis of rhazinilam analogue acting as an inhibitor of tubulin assembly," Tetrahedron Lett. (2000) 41:5853-5856.
Firsching, A. et al., "Antiproliferative and angiostatic activity of suramin analogues," Cancer Res. (1995) 55:4957-4961.
Wolff, M.E., Burger's Medicinal Chemistry, 4th Edition, Part I, Wiley: New York (1979) 336-337.
United States Office Action for U.S. Appl. No. 11/569,007 dated Jun. 1, 2009 (10 pages).
United States Office Action for U.S. Appl. No. 10/591,140 dated Jul. 6, 2009 (16 pages).
United States Office Action for U.S. Appl. No. 10/602,521 dated Sep. 9, 2009 (14 pages).
United States Office Action for U.S. Appl. No. 10/598,518 dated Sep. 28, 2009 (6 pages).
United States Patent Office Action for U.S. Appl. No. 10/591,140 dated Jan. 19, 2010 (7 pages).
United States Patent Office Action for U.S. Appl. No. 12/089,459 dated Oct. 14, 2010 (13 pages).
United States Patent Office Action for U.S. Appl. No. 10/591,140 dated Dec. 6, 2010 (7 pages).
Dattolo. G. et al., "Polycondensed nitrogen hterecycles. IX. 5,6-dihydro-7H-pyrrolo[1,2-d][1,4]benzodiazepin-6-one," J. Heterocyclic. Chem. (1980) 17:701-703.
Xie, G. et la., "Bisindolylmalemides linked to DNA minor groove binding lexitropsins: synthesis, inhibitory activity against topoisomerasel, and biological evaluation," J. Med. Chem. (1996) 39:1049-1055.

PYRROLOBENZODIAZEPINES

CROSS-REFERENCE TO RELATED APPLICATIONS

This patent application is a continuation of U.S. application Ser. No. 11/911,890, filed Oct. 18, 2007, now U.S. Pat. No. 7,612,062, which is a national stage filing under 35 U.S.C. 371 of International Application No. PCT/GB2006/001456, filed Apr. 21, 2006, which claims foreign priority benefits to United Kingdom Application No. 0522746.7, filed Nov. 7, 2005 and United Kingdom Application No. 0508084.1, filed Apr. 21, 2005. These applications are incorporated herein by reference in their entireties.

The present invention relates to pyrrolobenzodiazepines (PBDs), and in particular pyrrolobenzodiazepine dimers bearing C2 aryl substitutions.

BACKGROUND TO THE INVENTION

Some pyrrolobenzodiazepines (PBDs) have the ability to recognize and bond to specific sequences of DNA; the preferred sequence is PuGPu. The first PBD antitumour antibiotic, anthramycin, was discovered in 1965 (Leimgruber, et al., *J. Am. Chem. Soc.*, 87, 5793-5795 (1965); Leimgruber, et al., *J. Am. Chem. Soc.*, 87, 5791-5793 (1965)). Since then, a number of naturally occurring PBDs have been reported, and over 10 synthetic routes have been developed to a variety of analogues (Thurston, et al., *Chem. Rev.* 1994, 433-465 (1994)). Family members include abbeymycin (Hochlowski, et al., *J. Antibiotics*, 40, 145-148 (1987)), chicamycin (Konishi, et al., *J. Antibiotics*, 37, 200-206 (1984)), DC-81 (Japanese Patent 58-180 487; Thurston, et al., *Chem. Brit.*, 26, 767-772 (1990); Bose, et al., *Tetrahedron*, 48, 751-758 (1992)), mazethramycin (Kuminoto, et al., *J. Antibiotics*, 33, 665-667 (1980)), neothramycins A and B (Takeuchi, et al., *J. Antibiotics*, 29, 93-96 (1976)), porothramycin (Tsunakawa, et al., *J. Antibiotics*, 41, 1366-1373 (1988)), prothracarcin (Shimizu, et al, *J. Antibiotics*, 29, 2492-2503 (1982); Langley and Thurston, *J. Org. Chem.*, 52, 91-97 (1987)), sibanomicin (DC-102)(Hara, et al., *J. Antibiotics*, 41, 702-704 (1988); Itoh, et al., *J. Antibiotics*, 41, 1281-1284 (1988)), sibiromycin (Leber, et al., *J. Am. Chem. Soc.*, 110, 2992-2993 (1988)) and tomamycin (Arima, et al., *J. Antibiotics*, 25, 437-444 (1972)). PBDs are of the general structure:

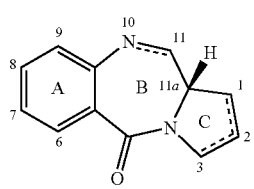

They differ in the number, type and position of substituents, in both their aromatic A rings and pyrrolo C rings, and in the degree of saturation of the C ring. In the B-ring there is either an imine (N=C), a carbinolamine(NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position which provides them with a right-handed twist when viewed from the C ring towards the A ring. This gives them the appropriate three-dimensional shape for isohelicity with the minor groove of B-form DNA, leading to a snug fit at the binding site (Kohn, In *Antibiotics III*. Springer-Verlag, New York, pp. 3-11 (1975); Hurley and Needham-VanDevanter, *Acc. Chem. Res.*, 19, 230-237 (1986)). Their ability to form an adduct in the minor groove, enables them to interfere with DNA processing, hence their use as antitumour agents.

The present inventors have previously disclosed, in WO 2004/043963, cytotoxic compounds having an aryl group at the C2 position, for example:

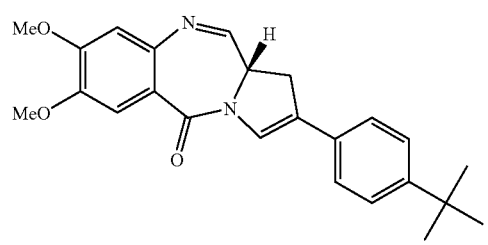 [SMILES: COc1cc2c(cc1OC)C(=O)N1C=C(c3ccc(C(C)(C)C)cc3)C[C@H]1C=N2]

The present inventors have also previously disclosed, in co-pending PCT application PCT/GB2005/000768 (published as WO 2005/085251), dimeric PBD compounds bearing C2 aryl substituents, such as:

ZC-207

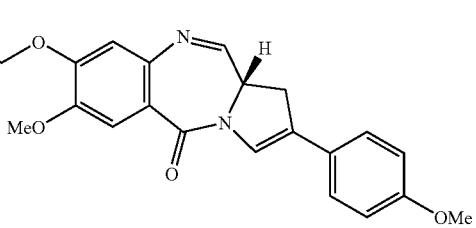

DISCLOSURE OF THE INVENTION

Figure 1:
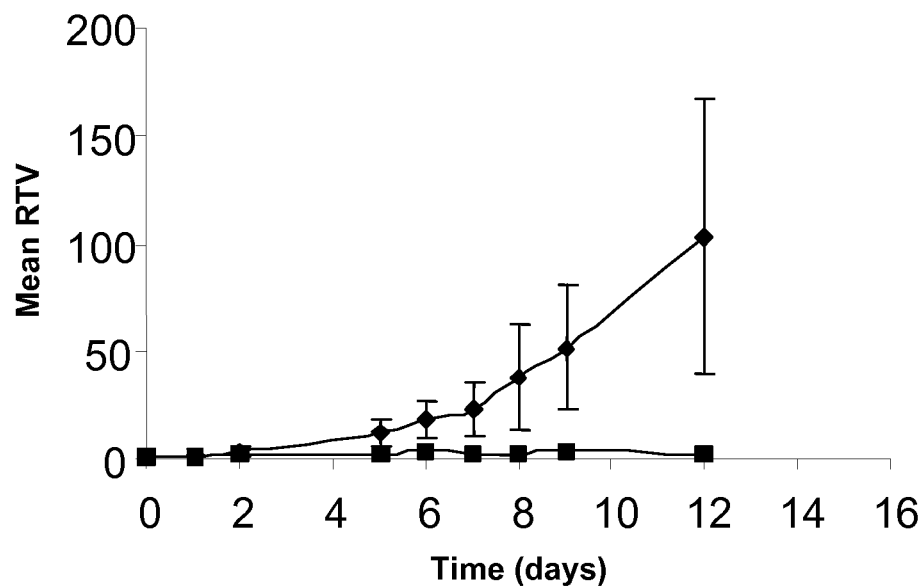
FIG. 1 is a graph of relative tumour volume (RTV) versus time during treatment of mice bearing LOX IMVI (human melanoma) with ZC423.

The present inventors have encountered some issues with the solubility of compounds such as ZC-207, which they have resolved by the use of a different form of these compounds.

The present invention comprises a compound with the formula I:

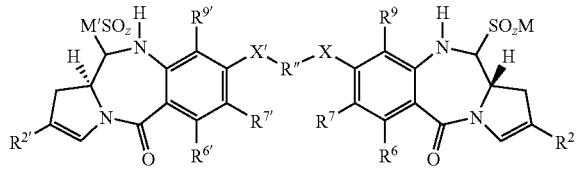

or solvate thereof, wherein:
$R^2$ is an optionally substituted $C_{5-20}$ aryl group;
$R^6$ and $R^9$ are independently selected from H, R, OH, OR, SH, SR, $NH_2$, NHR, NRR', nitro, $Me_3Sn$ and halo;
where R and R' are independently selected from optionally substituted $C_{1-12}$ alkyl, $C_{3-20}$ heterocyclyl and $C_{5-20}$ aryl groups;
$R^7$ is selected from H, R, OH, OR, SH, SR, $NH_2$, NHR, NHRR', nitro, $Me_3Sn$ and halo;
R" is a $C_{3-12}$ alkylene group, which chain may be interrupted by one or more heteroatoms,
e.g. O, S, NH, and/or aromatic rings, e.g. benzene or pyridine;
X is selected from O, S, or NH;
z is 2 or 3;
M is a monovalent pharmaceutically acceptable cation;
$R^{2'}$, $R^{6'}$, $R^{7'}$, $R^{9'}$, X' and M' are selected from the same groups as $R^2$, $R^6$, $R^7$, $R^9$, X and M respectively, or M and M' may together represent a divalent pharmaceutically acceptable cation.

Pyrrolobenzodiazepines having an imine bond are known to convert to the di-carbinolamine form in water, and isolated pyrrolobenzodiazepines often exist as a mixture of the imine, mono-carbinolamine and di-carbinolamine forms. Furthermore, if the compound is isolated as a solid with a mixture of these three forms, the balance between them may change over time. Although this does not pose a problem for administration of the compound, it can provide difficulties in accurately assessing the amount of active substance in a given amount of powder. Compounds of the present invention, at least to some extent, overcome this difficulty whilst remaining activity, and are thus suited to formulation as pharmaceuticals.

Dimeric pyrrolobenzodiazepines offer advantages over monomeric pyrrolobenzodiazepines in that they possess the ability to cross-link DNA in the minor groove, which can lead to an increase in cytotoxicity.

Further aspects of the invention relate to the compounds use in methods of therapy (particularly in treating proliferative diseases), pharmaceutical compositions comprising the compounds, and their use in the manufacture of a medicament for the treatment of a proliferative disease.

DEFINITIONS

Substituents

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

$C_{1-12}$ alkyl: The term "$C_{1-12}$ alkyl" as used herein, pertains to a monovalent moiety obtained by removing a hydrogen atom from a carbon atom of a hydrocarbon compound having from 1 to 12 carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$), butyl ($C_4$), pentyl ($C_5$), hexyl ($C_6$) and heptyl ($C_7$).

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{2-12}$ Alkenyl: The term "$C_{2-12}$ alkenyl" as used herein, pertains to an alkyl group having one or more carbon-carbon double bonds.

Examples of unsaturated alkenyl groups include, but are not limited to, ethenyl (vinyl, $—CH=CH_2$), 1-propenyl ($—CH=CH—CH_3$), 2-propenyl (allyl, $—CH—CH=CH_2$), isopropenyl (1-methylvinyl, $—C(CH_3)=CH_2$), butenyl ($C_4$), pentenyl ($C_5$), and hexenyl ($C_6$).

$C_{2-12}$ alkynyl: The term "$C_{2-12}$ alkynyl" as used herein, pertains to an alkyl group having one or more carbon-carbon triple bonds.

Examples of unsaturated alkynyl groups include, but are not limited to, ethynyl (ethinyl, $—C≡CH$) and 2-propynyl (propargyl, $—CH_2—C≡CH$).

$C_{3-12}$ cycloalkyl: The term "$C_{3-12}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:
saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$);
unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$) and methylcyclohexene ($C_7$); and
saturated polycyclic hydrocarbon compounds:
norcarane ($C_7$), norpinane ($C_7$), norbornane ($C_7$).

$C_{3-20}$ heterocyclyl: The term "$C_{3-20}$ heterocyclyl" as used herein, pertains to a monovalent moiety obtained by removing a hydrogen atom from a ring atom of a heterocyclic compound, which moiety has from 3 to 20 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl", as used herein, pertains to a heterocyclyl group having 5 or 6 ring atoms.

Examples of monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-20}$ aryl: The term "$C_{5-20}$ aryl", as used herein, pertains to a monovalent moiety obtained by removing a hydrogen atom from an aromatic ring atom of an aromatic compound, which moiety has from 3 to 20 ring atoms. Preferably, each ring has from 5 to 7 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups".

Examples of carboaryl groups include, but are not limited to, those derived from benzene (i.e. phenyl) ($C_6$), naphthalene (CO, azulene (CO, anthracene ($C_{14}$), phenanthrene ($C_{14}$), naphthacene (CO, and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$ (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH($OR^1$)($OR^2$), wherein $R^1$ and $R^2$ are independently acetal substituents, for example, a $C_{1-7}$ alkyl group, a $C_{3-20}$ heterocyclyl group, or a $C_{5-20}$ aryl group, preferably a $C_{1-7}$ alkyl group, or, in the case of a "cyclic" acetal group, $R^1$ and $R^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)($OR^1$), wherein $R^1$ is a hemiacetal substituent, for example, a $C_{1-7}$ alkyl group, a $C_{3-20}$ heterocyclyl group, or a $C_{5-20}$ aryl group, preferably a $C_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, C$_{1-7}$ alkyl group, a C$_{3-20}$ heterocyclyl group, or a C$_{5-20}$ aryl group, preferably hydrogen or a C$_{1-7}$ alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a C$_{1-7}$ alkyl group (also referred to as C$_{1-7}$alkylacyl or C$_{1-7}$alkanoyl), a C$_{3-20}$ heterocyclyl group (also referred to as C$_{3-20}$ heterocyclylacyl), or a C$_{5-20}$ aryl group (also referred to as C$_{5-20}$ arylacyl), preferably a C$_{1-7}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a C$_{1-7}$ alkyl group, a C$_{3-20}$ heterocyclyl group, or a C$_{5-20}$ aryl group, preferably a C$_{1-7}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a C$_{1-7}$ alkyl group, a C$_{3-20}$ heterocyclyl group, or a C$_{5-20}$ aryl group, preferably a C$_{1-7}$ alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amino: —NR$^1$R$^2$, wherein R$^1$ and R$^2$ are independently amino substituents, for example, hydrogen, a C$_{1-7}$ alkyl group (also referred to as C$_{1-7}$ alkylamino or di-C$_{1-7}$ alkylamino), a C$_{3-20}$ heterocyclyl group, or a C$_{5-20}$ aryl group, preferably H or a C$_{1-7}$ alkyl group, or, in the case of a "cyclic" amino group, R$^1$ and R$^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R$^1$ and R$^2$, together with the nitrogen atom to which they are attached, form a heterocyclic structure as in, for example, piperidinocarbonyl, morpholinocarbonyl, thiomorpholinocarbonyl, and piperazinocarbonyl.

Thioamido (thiocarbamyl): —C(=S)NR$^1$R$^2$, wherein R$^1$ and R$^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Acylamido (acylamino): —NR$^1$C(=O)R$^2$, wherein R$^1$ is an amide substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group, and R$^2$ is an acyl substituent, for example, a C$_{1-7}$ alkyl group, a C$_{3-20}$ heterocyclyl group, or a C$_{5-20}$ aryl group, preferably hydrogen or a C$_{1-7}$ alkyl group. Examples of acylamide groups include, but are not limited to, —NHC(=O)CH$_3$, —NHC(=O)CH$_2$CH$_3$, and —NHC(=O)Ph. R$^1$ and R$^2$ may together form a cyclic structure, as in, for example, succinimidyl, maleimidyl, and phthalimidyl:

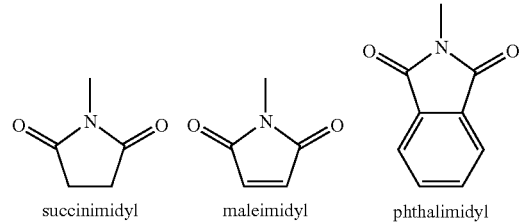

succinimidyl    maleimidyl    phthalimidyl

Aminocarbonyloxy: —OC(=O)NR$^1$R$^2$, wherein R$^1$ and R$^2$ are independently amino substituents, as defined for amino groups. Examples of aminocarbonyloxy groups include, but are not limited to, —OC(=O)NH$_2$, —OC(=O)NHMe, —OC(=O)NMe$_2$, and —OC(=O)NEt$_2$.

Ureido: —N(R$^1$)CONR$^2$R$^3$ wherein R$^2$ and R$^3$ are independently amino substituents, as defined for amino groups, and R$^1$ is a ureido substituent, for example, hydrogen, a C$_{1-7}$ alkyl group, a C$_{3-20}$ heterocyclyl group, or a C$_{5-20}$ aryl group, preferably hydrogen or a C$_{1-7}$ alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

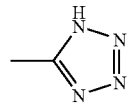

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of imino groups include, but are not limited to, =NH, =NMe, and =NEt.

Amidine (amidino): —C(=NR)NR$_2$, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH$_2$, —C(=NH)NMe$_2$, and —C(=NMe)NMe$_2$.

Nitro: —NO$_2$.

Nitroso: —NO.

Azido: —N$_3$.

Cyano (nitrile, carbonitrile): —CN.

Isocyano: —NC.

Cyanato: —OCN.

Isocyanato: —NCO.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a $C_{1-7}$ alkyl group (also referred to as a $C_{1-7}$alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH$_3$ and —SCH$_2$CH$_3$.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH$_3$ and —SSCH$_2$CH$_3$.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH$_3$ and —S(=O)CH$_2$CH$_3$.

Sulfone (sulfonyl): —S(=O)$_2$R, wherein R is a sulfone substituent, for example, a $C_{1-7}$ alkyl group, a $C_{3-20}$ heterocyclyl group, or a $C_{5-20}$ aryl group, preferably a $C_{1-7}$ alkyl group, including, for example, a fluorinated or perfluorinated $C_{1-7}$ alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$CH$_2$CH$_2$NH$_2$ (tauryl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —S(=O)OH, —SO$_2$H.

Sulfonic acid (sulfo): —S(=O)$_2$OH, —SO$_3$H.

Sulfinate (sulfinic acid ester): —S(=O)OR; wherein R is a sulfinate substituent, for example, a $C_{1-7}$ alkyl group, a $C_{3-20}$ heterocyclyl group, or a $C_{5-20}$ aryl group, preferably a $C_{1-7}$ alkyl group. Examples of sulfinate groups include, but are not limited to, —S(=O)OCH$_3$ (methoxysulfinyl; methyl sulfinate) and —S(=O)OCH$_2$CH$_3$ (ethoxysulfinyl; ethyl sulfinate).

Sulfonate (sulfonic acid ester): —S(=O)$_2$OR, wherein R is a sulfonate substituent, for example, a $C_{1-7}$ alkyl group, a $C_{3-20}$ heterocyclyl group, or a $C_{5-20}$ aryl group, preferably a $C_{1-7}$ alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a $C_{1-7}$ alkyl group, a $C_{3-20}$ heterocyclyl group, or a $C_{3-20}$ aryl group, preferably a $C_{1-7}$ alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a $C_{1-7}$ alkyl group, a $C_{3-20}$ heterocyclyl group, or a $C_{5-20}$ aryl group, preferably a $C_{1-7}$ alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a $C_{1-7}$ alkyl group, a $C_{3-20}$ heterocyclyl group, or a $C_{5-20}$ aryl group, preferably a $C_{1-7}$ alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a $C_{1-7}$ alkyl group, a $C_{3-20}$ heterocyclyl group, or a $C_{5-20}$ aryl group, preferably a $C_{1-7}$ alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a $C_{1-7}$ alkyl group, a $C_{3-20}$ heterocyclyl group, or a $C_{3-20}$ aryl group, preferably a $C_{1-7}$ alkyl group. Examples of sulfinamino groups include, but are not limited to, —NHS(=O)CH$_3$ and —N(CH$_3$)S(=O)C$_6$H$_5$.

Phosphino (phosphine): —PR$_2$, wherein R is a phosphino substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphino groups include, but are not limited to, —PH$_2$, —P(CH$_3$)$_2$, —P(CH$_2$CH$_3$)$_2$, —P(t-Bu)$_2$, and —P(Ph)$_2$.

Phospho: —P(=O)$_2$.

Phosphinyl (phosphine oxide): —P(=O)R$_2$, wherein R is a phosphinyl substituent, for example, a $C_{1-7}$ alkyl group, a $C_{3-20}$ heterocyclyl group, or a $C_{3-20}$ aryl group, preferably a $C_{1-7}$ alkyl group or a $C_{5-20}$ aryl group. Examples of phosphinyl groups include, but are not limited to, —P(=O)(CH$_3$)$_2$, —P(=O)(CH$_2$CH$_3$)$_2$, —P(=O)(t-Bu)$_2$, and —P(=O)(Ph)$_2$.

Phosphonic acid (phosphono): —P(=O)(OH)$_2$.

Phosphonate (phosphono ester): —P(=O)(OR)$_2$, where R is a phosphonate substituent, for example, —H, a $C_{1-7}$ alkyl group, a $C_{3-20}$ heterocyclyl group, or a $C_{5-20}$ aryl group, preferably —H, a $C_{1-7}$ alkyl group, or a $C_{5-20}$ aryl group. Examples of phosphonate groups include, but are not limited to, —P(=O)(OCH$_3$)$_2$, —P(=O)(OCH$_2$CH$_3$)$_2$, —P(=O)(O-t-Bu)$_2$, and —P(=O)(OPh)$_2$.

Phosphoric acid (phosphonooxy): —OP(=O)(OH)$_2$.

Phosphate (phosphonooxy ester): —OP(=O)(OR)$_2$, where R is a phosphate substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphate groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

Phosphorous acid: —OP(OH)$_2$.

Phosphite: —OP(OR)$_2$, where R is a phosphite substituent, for example, —H, a C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphite groups include, but are not limited to, —OP(OCH$_3$)$_2$, —OP(OCH$_2$CH$_3$)$_2$, —OP(O-t-Bu)$_2$, and —OP(OPh)$_2$.

Phosphoramidite: —OP(OR$^1$)—NR$_2^2$, where R$^1$ and R$^2$ are phosphoramidite substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidite groups include, but are not limited to, —OP(OCH$_2$CH$_3$)—N(CH$_3$)$_2$, —OP(OCH$_2$CH$_3$)—N(i-Pr)$_2$, and —OP(OCH$_2$CH$_2$CN)—N(i-Pr)$_2$.

Phosphoramidate: —OP(=O)(OR$^1$)—NR$_2^2$, where R$^1$ and R$^2$ are phosphoramidate substituents, for example, —H, a (optionally substituted) C$_{1-7}$ alkyl group, a C$_{3-20}$ heterocyclyl group, or a C$_{5-20}$ aryl group, preferably —H, a C$_{1-7}$ alkyl group, or a C$_{5-20}$ aryl group. Examples of phosphoramidate groups include, but are not limited to, —OP(=O)(OCH$_2$CH$_3$)—N(CH$_3$)$_2$, —OP(=O)(OCH$_2$CH$_3$)—N(i-Pr)$_2$, and —OP(=O)(OCH$_2$CH$_2$CN)—N(i-Pr)$_2$.

Bisoxyalkylene: —O—(CH$_2$)$_n$—O—, where n=1-3, which bonds to adjacent atoms. Examples of bisoxyalkylene groups include, but are not limited to, —O—CH$_2$—O—.

Alkylene

C$_{3-12}$ alkylene: The term "C$_{3-12}$ alkylene", as used herein, pertains to a bidentate moiety obtained by removing two hydrogen atoms, either both from the same carbon atom, or one from each of two different carbon atoms, of a hydrocarbon compound having from 3 to 12 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below.

Examples of linear saturated C$_{3-12}$ alkylene groups include, but are not limited to, —(CH$_2$)$_n$—where n is an integer from 3 to 12, for example, —CH$_2$CH$_2$CH$_2$— (propylene), —CH$_2$CH$_2$CH$_2$CH$_2$— (butylene), —CH$_2$CH$_2$CH$_2$CH$_2$CH$_2$— (pentylene) and —CH$_2$CH$_2$CH$_2$CH$_2$CH$_2$CH$_2$CH$_2$— (heptylene).

Examples of branched saturated C$_{3-12}$ alkylene groups include, but are not limited to, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated C$_{3-12}$ alkylene groups (C$_{3-12}$ alkenylene, and alkynylene groups) include, but are not limited to, —CH=CH—CH$_2$—, —CH$_2$—CH=CH$_2$—, —CH=CH—CH$_2$—CH$_2$—, —CH=CH—CH$_2$—CH$_2$—CH$_2$—, —CH=CH—CH=CH—CH$_2$—, —CH=CH—CH=CH—CH$_2$—CH$_2$—, —CH=CH—CH$_2$—CH=CH—, —CH=CH—CH$_2$—CH$_2$—CH=CH—, and —CH$_2$—C≡C—CH$_2$—.

Examples of branched partially unsaturated C$_{3-12}$ alkylene groups (C$_{3-12}$ alkenylene and alkynylene groups) include, but are not limited to, —C(CH$_3$)=CH—, —C(CH$_3$)=CH—CH$_2$—, —CH=CH—CH(CH$_3$)— and —C≡C—CH(CH$_3$)—.

Examples of alicyclic saturated C$_{3-12}$ alkylene groups (C$_{3-12}$ cycloalkylenes) include, but are not limited to, cyclopentylene (e.g. cyclopent-1,3-ylene), and cyclohexylene (e.g. cyclohex-1,4-ylene).

Examples of alicyclic partially unsaturated C$_{3-12}$ alkylene groups (C$_{3-12}$ cycloalkylenes) include, but are not limited to, cyclopentenylene (e.g. 4-cyclopenten-1,3-ylene), cyclohexenylene (e.g. 2-cyclohexen-1,4-ylene; 3-cyclohexen-1,2-ylene; 2,5-cyclohexadien-1,4-ylene).

Pharmaceutically Acceptable Cations

Examples of pharmaceutically acceptable monovalent and divalent cations are discussed in Berge, et al., *J. Pharm. Sci.*, 66, 1-19 (1977), which is incorporated herein by reference.

The pharmaceutically acceptable cation may be inorganic or organic.

Examples of pharmaceutically acceptable monovalent inorganic cations include, but are not limited to, alkali metal ions such as Na$^+$ and K$^+$. Examples of pharmaceutically acceptable divalent inorganic cations include, but are not limited to, alkaline earth cations such as Ca$^{2+}$ and Mg$^{2+}$. Examples of pharmaceutically acceptable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Proliferative Diseases

One of ordinary skill in the art is readily able to determine whether or not a candidate compound treats a proliferative condition for any particular cell type. For example, assays which may conveniently be used to assess the activity offered by a particular compound are described in the examples below.

The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g. histocytoma, glioma, astrocyoma, osteoma), cancers (e.g. lung cancer, small cell lung cancer, gastrointestinal cancer, bowel cancer, colon cancer, breast carinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g. of connective tissues), and atherosclerosis.

Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Methods of Treatment

As described above, the present invention provide the use of a compound of formula I in a method of therapy. Also provided is a method of treatment, comprising administering to a subject in need of treatment a therapeutically-effective amount of a compound of formula I, preferably in the form of a pharmaceutical composition. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A compound may be administered alone or in combination with other treatments, either simultaneously or sequentially dependent upon the condition to be treated. Examples of treatments and therapies include, but are not limited to, chemotherapy (the administration of active agents, including, e.g. drugs; surgery; and radiation therapy.

Pharmaceutical compositions according to the present invention, and for use in accordance with the present invention, may comprise, in addition to the active ingredient, i.e. a compound of formula I, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

In particular, a reference to group (—SO$_z$M) also includes the anionic form (—SO$_z^-$), or solvate thereof, as well as conventional protected forms.

Isomers and Solvates

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

In some embodiments, compounds of the present invention have the following stereochemistry at the C11 position:

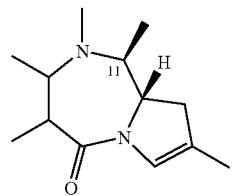

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

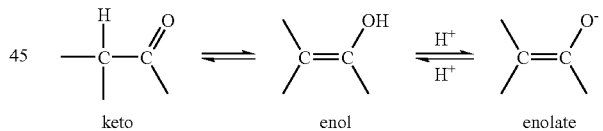

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

General Synthetic Routes

The synthesis of PBD compounds is extensively discussed in WO 00/12508, which discussion is incorporated herein by reference.

As discussed in that patent application, a key step in a preferred route to PBDs is a cyclisation to produce the B-ring, involving generation of an aldehyde (or functional equivalent thereof) at what will be the 11-position, and attack thereon by the Pro-N10-nitrogen:

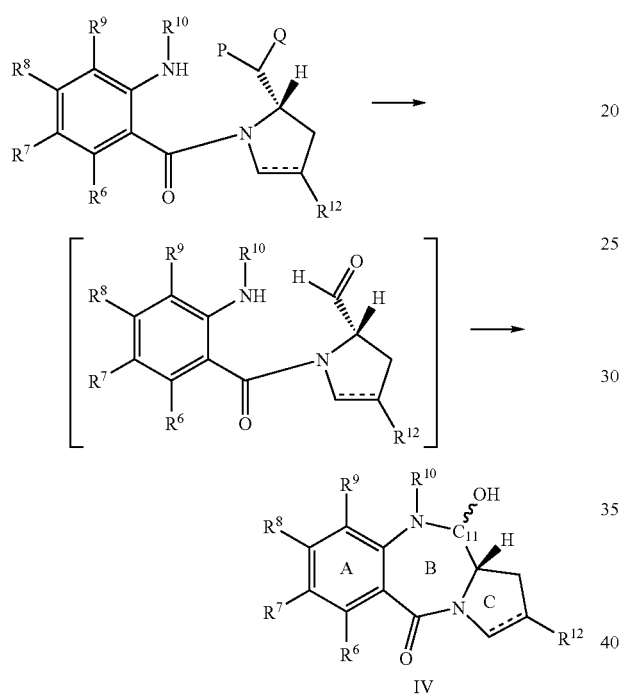

wherein the substituents are as defined above, $R^8$ represents the link (—X—R''—X—) to the other PBD moiety, $R^{10}$ is a nitrogen protecting group and $R^{12}$ is $R^2$ or a precursor thereof. The "masked aldehyde" —CPQ may be an acetal or thioacetal, in which case the cyclisation involves unmasking. Alternatively, it may be an alcohol —CHOH, in which case the reaction involves oxidation, e.g. by means of TPAP, TEMPO or DMSO (Swern oxidation).

The masked aldehyde compound can be produced by condensing a corresponding 2,4-substituted pyrrolidine with a 2-nitrobenzoic acid:

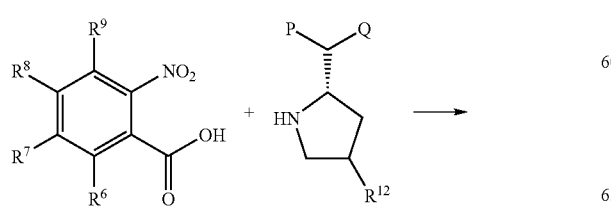

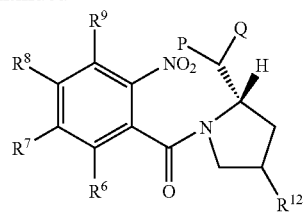

The nitro group can then be reduced to —NH$_2$ and protected by reaction with a suitable agent, e.g. a chloroformate, which provides the removable nitrogen protecting group in the compound of formula IV.

A process involving the oxidation-cyclization procedure is illustrated in scheme 1 (an alternative type of cyclisation will be described later with reference to scheme 2).

Scheme 1

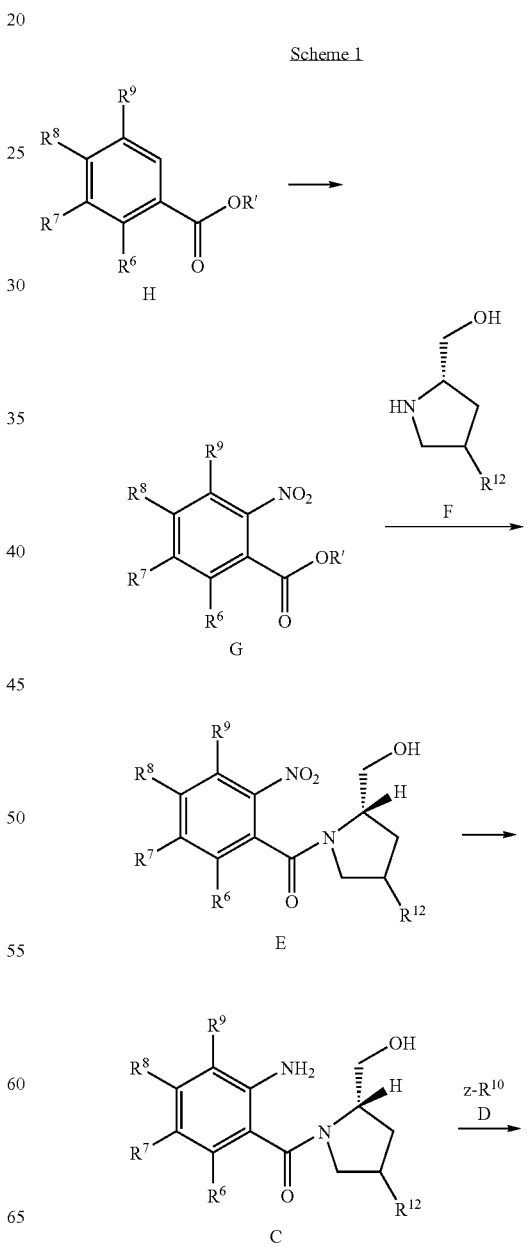

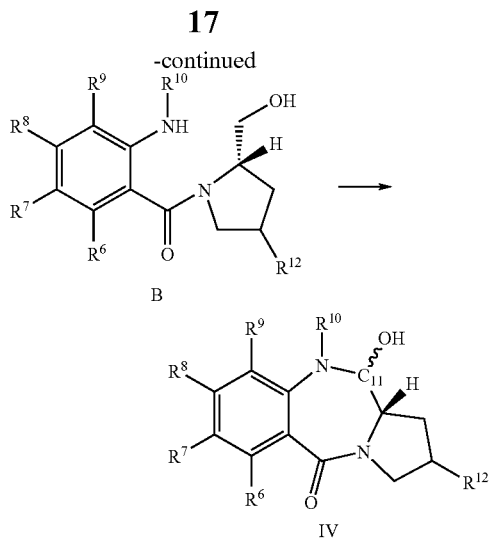

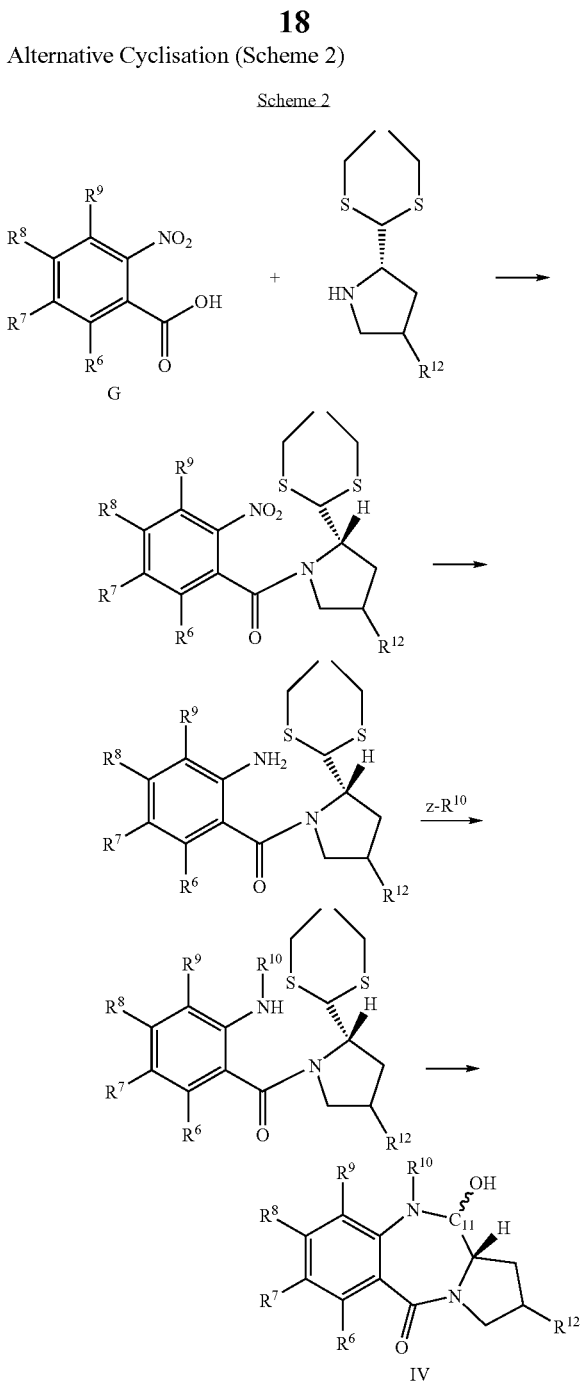

Alternative Cyclisation (Scheme 2)

Exposure of the alcohol (B) (in which the Pro-N10-nitrogen is generally protected as carbamate) to tetrapropylammonium perruthenate (TPAP)/N-methylmorpholine N-oxide (NMO) over A4 sieves results in oxidation accompanied by spontaneous B-ring closure to afford the desired product IV. The TPAP/NMO oxidation procedure is found to be particularly convenient for small scale reactions while the use of DMSO-based oxidation methods, particularly Swern oxidation, proves superior for larger scale work (e.g. >1 g). A particularly preferred oxidising agent is (diacetoxyiodo)benzene (1.1 eq) and TEMPO (0.1 eq) dissolved in $CH_2Cl_2$.

The uncyclized alcohol (B) may be prepared by the reaction of a nitrogen protection reagent of formula D, which is preferably a chloroformate or acid chloride, to a solution of the amino alcohol C, generally in solution, generally in the presence of a base such as pyridine (preferably 2 equivalents) at a moderate temperature (e.g. at 0° C.). Under these conditions little or no O-acylation is usually observed.

The key amino alcohol C may be prepared by reduction of the corresponding nitro compound E, by choosing a method which will leave the rest of the molecule intact. Treatment of E with tin (II) chloride in a suitable solvent, e.g. refluxing methanol, generally affords, after the removal of the tin salts, the desired product in high yield.

Exposure of E to hydrazine/Raney nickel avoids the production of tin salts and may result in a higher yield of C, although this method is less compatible with the range of possible C and A-ring substituents. For instance, if there is C-ring unsaturation (either in the ring itself, or in $R_2$ or $R_3$), this technique may be unsuitable. Another suitable means of reduction would be catalytic hydrogenation using palladium on carbon as a catalyst.

The nitro compound of formula E may be prepared by coupling the appropriate o-nitrobenzoyl chloride to a compound of formula F, e.g. in the presence of $K_2CO_3$ at –25° C. under a $N_2$ atmosphere. Compounds of formula F can be readily prepared, for example by olefination of the ketone derived from L-trans-hydroxy proline. The ketone intermediate can also be exploited by conversion to the enol triflate for use in palladium mediated coupling reactions.

The o-nitrobenzoyl chloride is synthesised from the o-nitrobenzoic acid (or alkyl ester after hydrolysis) of formula G, which itself is prepared from the vanillic acid (or alkyl ester) derivative H. Many of these are commercially available and some are disclosed in Althuis, T. H. and Hess, H. J., *J. Medicinal Chem.*, 20(1), 146-266 (1977).

In scheme 1, the final or penultimate step was an oxidative cyclisation. An alternative, using thioacetal coupling, is shown in scheme 2. Mercury-mediated unmasking causes cyclisation to the protected PBD compound IV.

The thioacetal compound may be prepared as shown in scheme 2: the thioacetal protected C-ring [prepared via a literature method: Langley, D. R. & Thurston, D. E., *J. Organic Chemistry*, 52, 91-97 (1987)] is coupled to the o-nitrobenzoic acid (or alkyl ester after hydrolysis) (G) using a literature procedure. The resulting nitro compound cannot be reduced by hydrogenation, because of the thioacetal group, so the tin(II) chloride method is used to afford the amine. This is then N-protected, e.g., by reaction with a chloroformate or acid chloride, such as 2,2,2-trichloroethylchloroformate.

Acetal-containing C-rings can be used as an alternative in this type of route with deprotection involving other methods, including the use of acidic conditions.

Dimer Synthesis (Scheme 3)

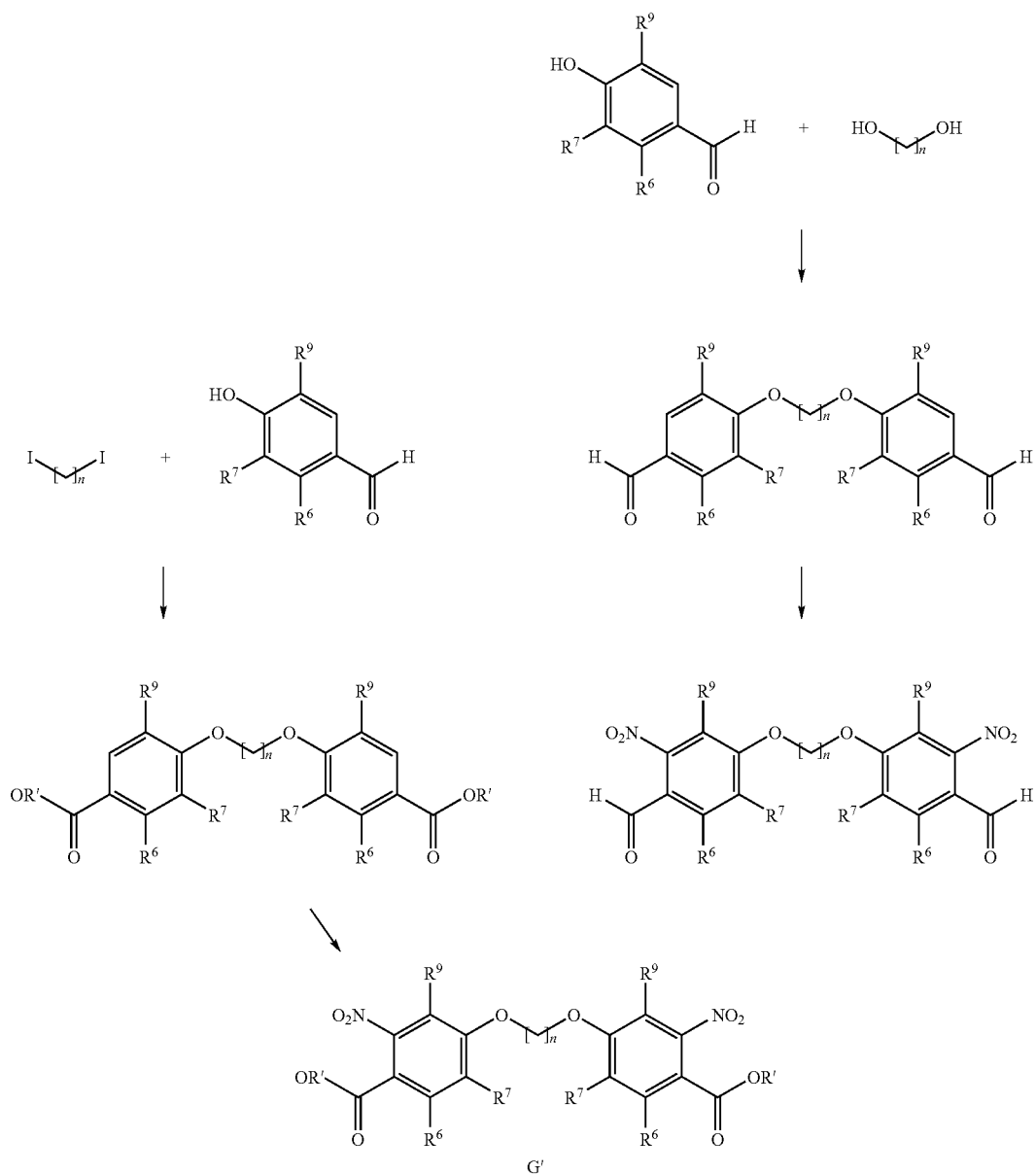

PBD dimers, as in the present invention, may be synthesized using the strategy developed for the synthesis of the protected PBD monomers. The synthesis routes illustrated in scheme 3 show compounds when the dimer linkage is of the formula —O—(CH$_2$)$_n$—O—, and may be readily modified for other dimer linkages. The step of dimer formation is normally carried out to form a bis(nitro acid) G'. This compound can then be treated as compound G in either scheme 1 or scheme 2 above.

The bis(nitro acid) G' may be obtained by nitrating (e.g. using 70% nitric acid) the bis(carboxylic acid). This can be synthesised by alkylation of two equivalents of the relevant benzoic acid with the appropriate diiodoalkane under basic conditions. Many benzoic acids are commercially available and others can be synthesised by conventional methods. Alternatively, the relevant benzoic acid esters can be joined together by a Mitsunobu etherification with an appropriate alkanediol, followed by nitration, and then hydrolysis (not illustrated).

An alternative synthesis of the bis(nitro acid) involves oxidation of the bis(nitro aldehyde), e.g. with potassium permanganate. This can be obtained in turn by direct nitration of the bis(aldehyde), e.g. with 70% HNO$_3$. Finally, the bis(aldehyde) can be obtained via the Mitsunobu etherification of two equivalents of the benzoic aldehyde with the appropriate alkanediol.

Alternative Routes to PBDs

Alternative methods of synthesising N10 protected PBDs are disclosed WO 2005/023814, which is incorporated herein, and which describes the use of isocyanate intermediates.

Introduction of C2 Aryl Substituent: Introducing Leaving Group at C2

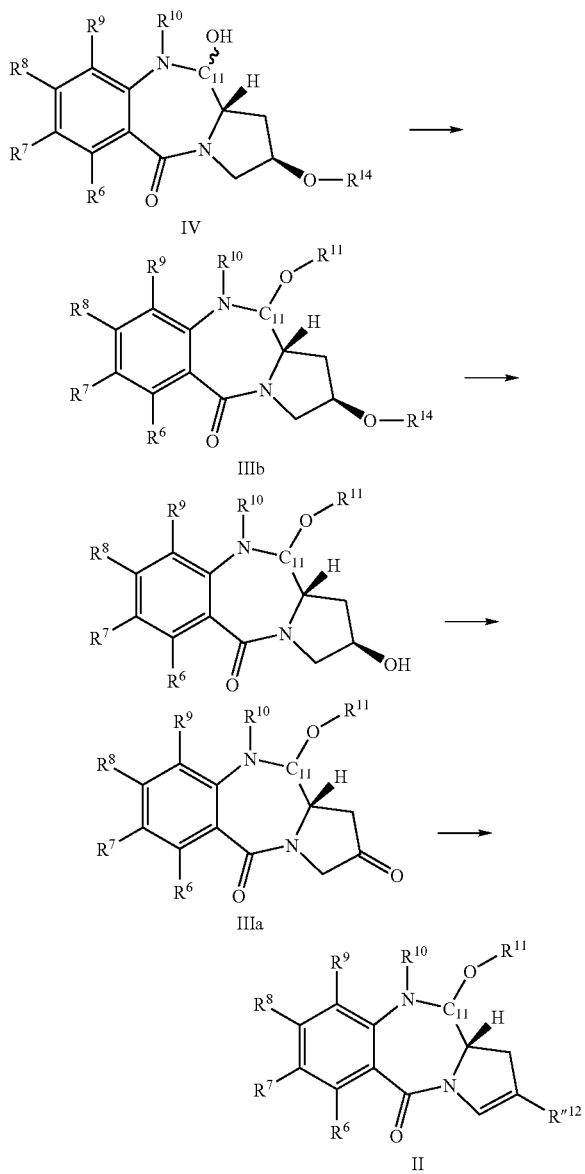

The C2 aryl substituent may be in place in compounds of formula IV, by starting with the appropriate material, in which case the N10 may be deprotected to yield the desired compound (see below). Alternatively, the following method can be used where $R^{12}$ is a protected hydroxy group. Following cyclisation to form the B-ring, the C11-alcohol IV is then preferably re-protected, by conventional means to provide IIIb. For example, if $R^{11}$ is TBS, the protection can take place by reacting IV with TBSOTf and 2,6-lutidine. Cleavage of the C2-protecting group from IIIb then provides the C2 alcohol. For example, where the C2 protecting group ($R^{14}$) is acyl, this deprotection may be performed by addition of an aqueous solution of $K_2CO_3$.

This reprotection at the C11 position and deprotection of the C2 alcohol allows subsequent reaction of selectively the C2 alcohol position leaving the C11 position unaffected. The C2-alcohol may then be oxidized to the ketone IIIb. Preferably this oxidation is performed under Swern conditions, in good yield. However, other oxidation methods involving TPAP or the Dess Martin reagent also provide the ketone in good yield.

$R'''^{12}$ in the compound of formula II may be $—OSO_2CH_3$, $—OSO_2(C_nF_{2n+1})$ where n=0, 1 or 4, or $—OSO_2R^S$, in which case the conversion from IIIb may be achieved by treatment with the appropriate anhydride. For example, if $R'''^{12}$ is triflate that reaction with trifluoromethanesulfonic anhydride in DCM in the presence of pyridine.

$R'''^{12}$ in the compound of formula II may also be —I or —Br, in which case the conversion from IIIb may be achieved by reaction with hydrazine and iodine or bromine respectively.

$R'''^{12}$ in the compound of formula II may also be —Cl, where the conversion from IIIb may be achieved by reaction with a phosphorous oxychloride (e.g. $POCl_3$).

Introduction of C2 Aryl Substituent: Replacement of Leaving Group

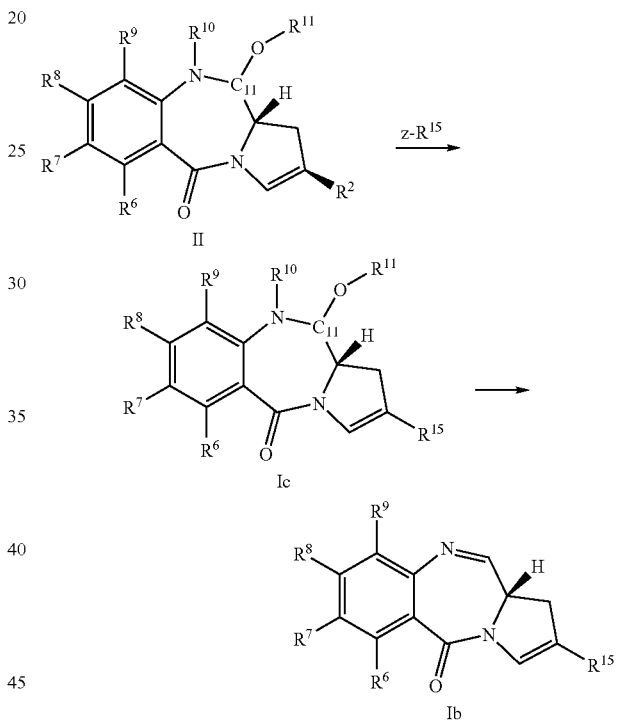

This compound of formula II may be reacted under a variety of conditions to yield PBD precursor molecules with pendant groups coupled at the C2 position Ic.

In particular, the use of palladium catalysed coupling is preferred, such as Suzuki, Stille and Heck coupling. The palladium catalyst may be any suitable catalyst, for example $Pd(PPh_3)_4$, $Pd(OCOCH_3)_2$, $PdCl_2$, $Pd(dba)_3$. The compounds which are coupled may be any suitable reactant, e.g. for Heck, alkenes with an $sp^2H$; for Stille, organostannanes; and for Suzuki, organoboron derivatives.

In a preferred aspect of the invention, the coupling may be performed under microwave conditions. Typically, the palladium catalyst, such as $Pd(PPh_3)_4$, is solid supported, for example on polystyrene, to facilitate work-up and allow potential recycling of catalyst. Unreacted boronic acid can be sequestered following complete consumption of triflate using PS-DEAM, with a phase separator cartridge being used to isolate the coupling product. Such a method allows for the parallel synthesis of more than one (e.g. up to 10, or 30) compound at the same time.

The imine bond in the compound of formula Ic can be unprotected by standard methods to yield the unprotected compound Ib (which may be in its carbinolamine or carbinolamine ether form, depending on the solvents used). For example if $R^{19}$ is Alloc, then the deprotection is carried using palladium to remove the N10 protecting group, followed by the elimination of water. If $R^{19}$ is Troc, then the deprotection is carried out using a Cd/Pb couple to yield the compound of formula Ib.

Reference is also made to the synthesis discussion and examples in WO 2004/043963 and WO 2005/085251, which are herein incorporated by reference.

Conversion to Sulphur Containing Form

The conversion of compounds of formula Ib to those of the present invention may be carried out by the addition of the appropriate bisulphite salt or sulphinate salt, followed by an appropriate purification step. Further methods are described in GB 2 053 894, which is herein incorporated by reference.

Further Preferences

It is preferred that X is O.

It is preferred that R" represents a linear saturated $C_{3-12}$ alkylene group, and more preferably an alkylene group having 3, 5, 7, 8, 9, 10, 11 or 12 carbon atoms. Of these $C_3$ and $C_5$ linear saturated alkylene groups are preferred.

$R^9$ is preferably H.

$R^6$ is preferably selected from H, OH, OR, SH, $NH_2$, nitro and halo, and is more preferably H or halo, and most preferably is H.

$R^7$ is preferably selected from H, OH, OR, SH, SR, $NH_2$, NHR, NRR', and halo, and more preferably independently selected from H, OH and OR, where R is preferably selected from optionally substituted $C_{1-7}$ alkyl, $C_{3-10}$ heterocyclyl and $C_{3-10}$ aryl groups. Particularly preferred substituents at the 7-position are OMe and $OCH_2Ph$.

$R^2$ is preferably an optionally substituted $C_{5-7}$ aryl group, and most preferably an optionally substituted phenyl group.

In some embodiments, $R^2$ is a $C_{9-12}$ aryl group, for example napthy-1-yl or napth-2-yl. Further examples of $C_{9-12}$ aryl groups include quinolinyl, for example, quinolin-2-yl, quinolin-3-yl and quinolin-6-yl.

In other embodiments, $R^2$ is a $C_{5-7}$ heteroaryl group, for example furanyl, thiophenyl and pyridyl. Of these thiophenyl is preferred, for example, thiophen-2-yl and thiophen-3-yl.

The $C_{5-20}$ aryl group may bear any substituent group. It preferably bears from 1 to 3 substituent groups, with 1 and 2 being more preferred, and singly substituted groups being most preferred.

Preferred $C_{5-20}$ aryl substituents, particularly for phenyl, include: halo (e.g. F, Cl, Br); $C_{1-7}$ alkoxy (e.g. methoxy, ethoxy); $C_{1-7}$ alkyl (e.g. methyl, trifluoromethyl, ethyl, propyl, t-butyl); bis-oxy-alkylene (e.g. bis-oxy-methylene, —O—$CH_2$—O—).

Particularly preferred substituted $C_{5-20}$ aryl groups include, but are not limited to, 4-methyl-phenyl, 4-methoxyphenyl, 3-methoxyphenyl, 4-fluoro-phenyl, 3,4-bisoxymethylene-phenyl, 4-triflouoromethylphenyl, 4-methylthiophenyl, 4-cyanophenyl and 4-phenoxyphenyl.

Particularly preferred unsubstituted $C_{5-20}$ aryl groups include, but are not limited to thiophen-2-yl, napth-2-yl, quinolin-3-yl and quinolin-6-yl.

If R is optionally substituted $C_{1-12}$ alkyl, it is preferred that it is optionally substituted $C_{1-7}$ alkyl.

It is preferred that both PBD monomers are identically substituted.

It is preferred that M and M' are monovalent pharmaceutically acceptable cations, and are more preferably $Na^+$.

z is preferably 3.

Preferred compounds include:

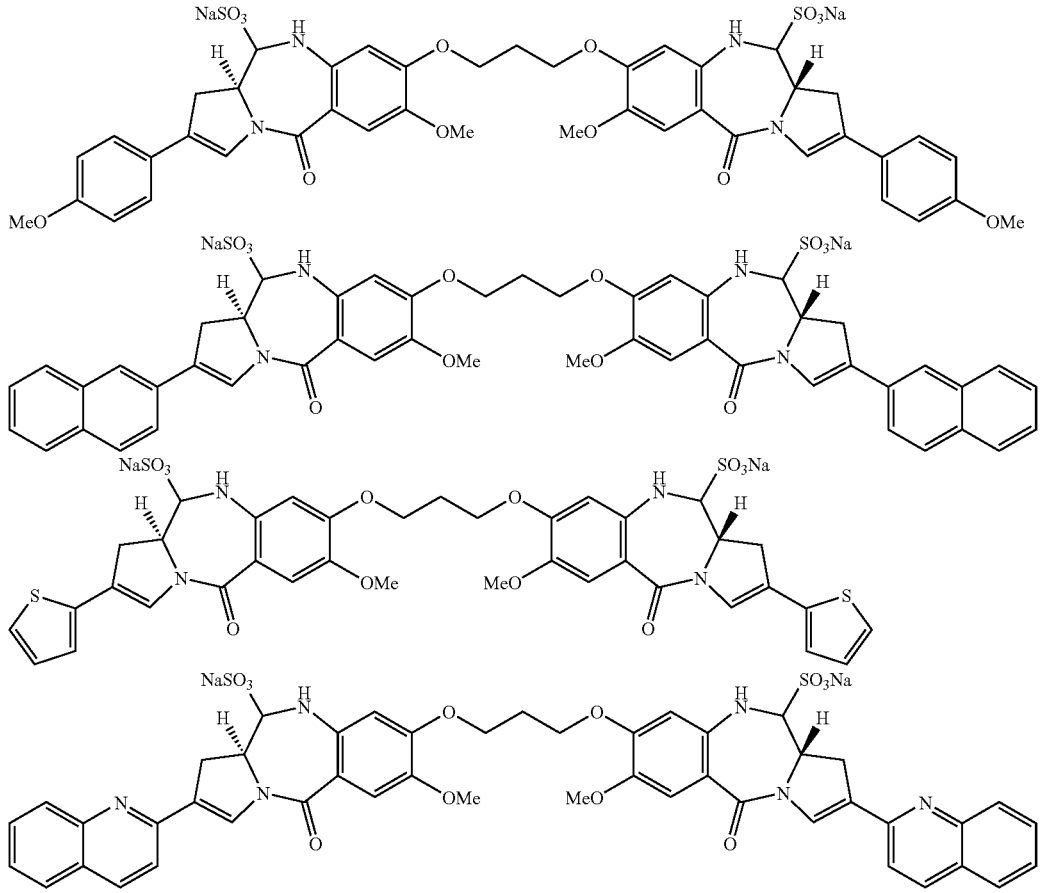

-continued
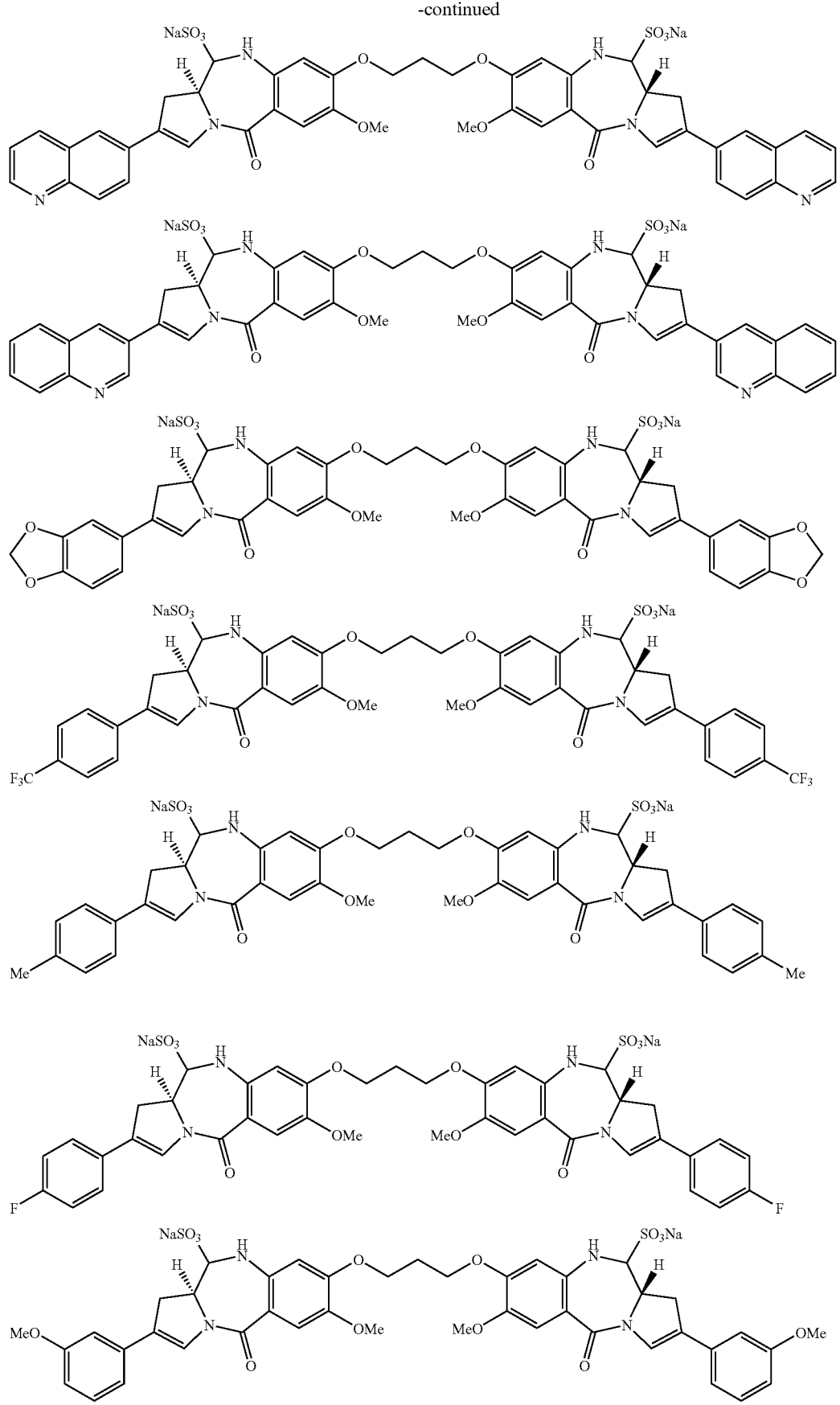

-continued
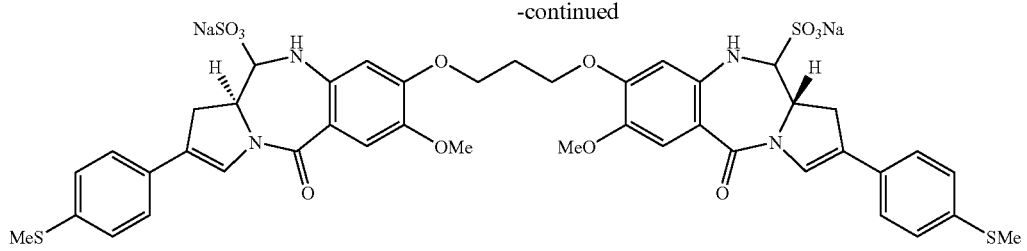
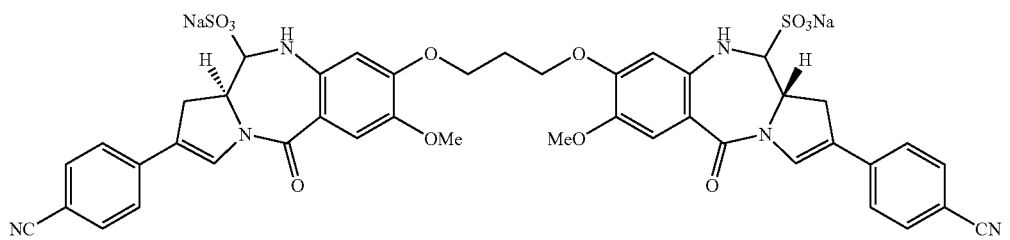
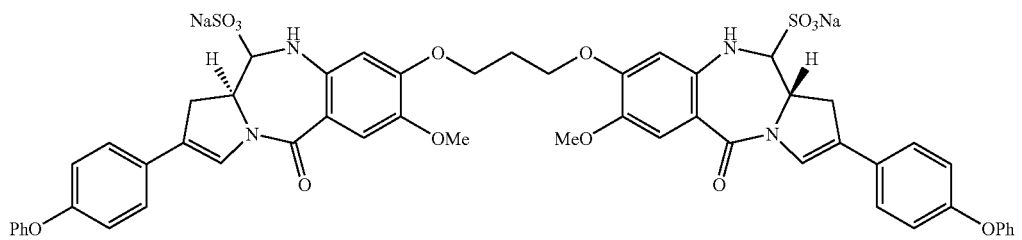
More preferred compounds include:
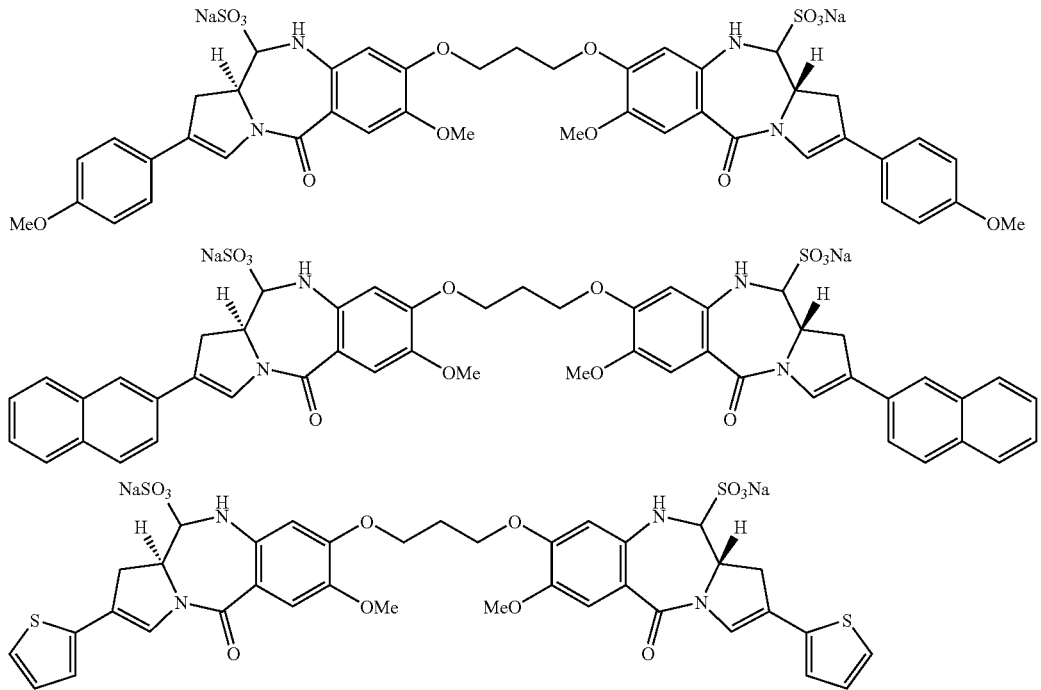

A most preferred compound is:

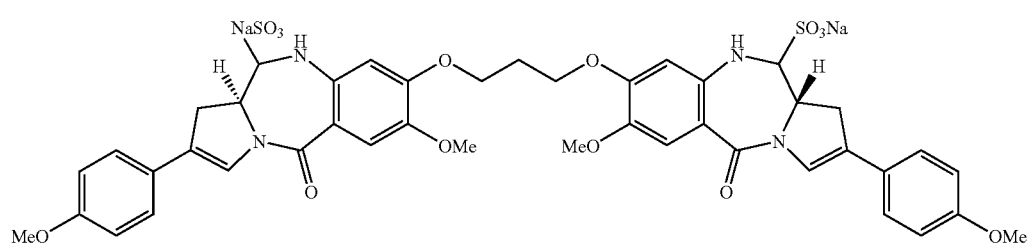
ZC-423

The above preferred compounds may also have a $C_5$ alkylene linking chain.

EXAMPLES

Example 1

(a) (2S,4R)—N-(Benzyloxycarbonyl)-2-t-butyldimethylsilyloxymethyl-4-hydroxypyrrolidine (1)

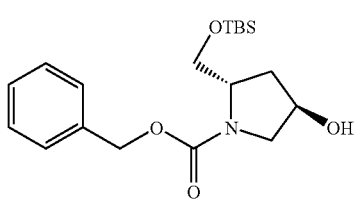

Compound 1 is formed in high yield in a four step process known in the art starting from trans-4-hydroxy-L-proline (S. J. Gregson et al., *J. Med. Chem.*, 2004, 1161-1174).

(b) (2S,4R)—N-(Benzyloxycarbonyl-2-t-butyldimethylsilyloxymethyl-4-oxyacetylpyrrolidine (2)

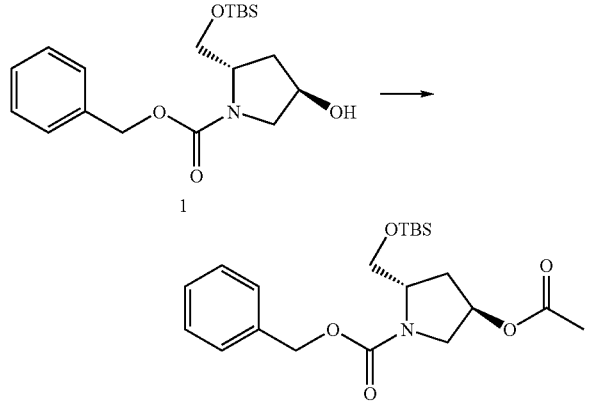

Pyridine (18.3 g, 18.7 mL, 232 mmol, 1.1 eq), acetic anhydride (23.6 g, 21.8 mL, 232 mmol, 1.1 eq) and DMAP (5.14 g, 42.1 mmol, 0.2 eq) were added to a stirred solution of 1 (76.9 g, 211 mmol) in dry THF (1 L). The reaction mixture was stirred for 16 hours after which time TLC (95:5 v/v CHCl$_3$/MeOH) showed the complete consumption of starting material. Excess solvent was removed by rotary evaporation and the residue was dissolved in EtOAc (1 L), washed with 1N HCl (2×1 L), H$_2$O (1 L), brine (1 L) and dried (MgSO$_4$). Filtration and evaporation of the solvent afforded acetate 2 as a colourless oil (80.7 g, 94%): $^1$H NMR (400 MHz, CDCl$_3$) (rotamers) δ7.36-7.12 (m, 5H), 5.30-5.10 (m, 3H), 4.09-3.97 (m, 2H), 3.74-3.55 (m, 3H), 2.36-2.29 (m, 1H), 2.11-2.06 (m, 1H), 2.02 (s, 3H), 0.87 (s, 6H), 0.86 (s, 3H), 0.03 and 0.00 (s×2, 6H); MS (ES), m/z (relative intensity) 430 ([M+Na]$^+$, 95), 408 ([M+H]$^+$, 100).

(c) (2S,4R)-2-t-Butyldimethylsilyloxymethyl-4-oxyacetylpyrrolidine (3)

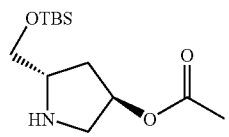

A slurry of silyl ether 2 (1.95 g, 4.80 mmol) and 10% Pd/C (0.17 g) in absolute ethanol (10 mL) was subjected to Parr hydrogenation at 45 Psi for 16 h after which time TLC (95:5 v/v CHCl$_3$/MeOH) showed the complete consumption of starting material. The reaction mixture was filtered through celite to remove the Pd/C, and the filter pad was washed repeatedly with ethanol. Excess solvent was removed by rotary evaporation under reduced pressure to afford the amine 3 as a pale orange waxy oil (1.28 g, 98%): IR (CHCl$_3$) 3315, 2930, 2858, 1739, 1652, 1472, 1435, 1375, 1251, 1088, 838, 779, 667 cm$^{-1}$.

(d) 1,1'-[[(Propane-1,3-diyl)dioxy]bis[(2S,4R)-(5-methoxy-2-nitro-1,4-phenylene)carbonyl]]bis[2-(tert-butyldimethylsilyloxymethyl)-4-oxyacetylpyrrolidine] (5)

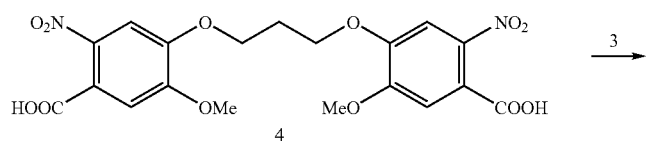

-continued

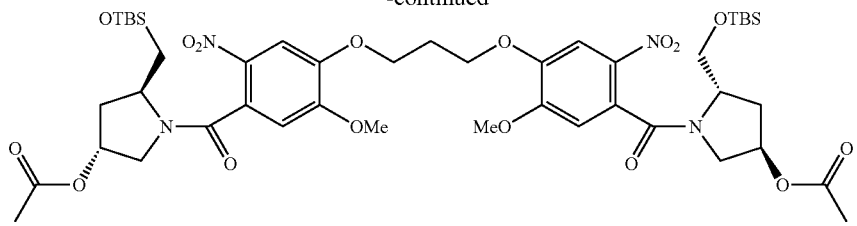

A catalytic amount of DMF (2 drops) was added to a stirred solution of the nitro-acid 4 (8.12 g, 17.4 mmol)[1] and oxalyl chloride (3.80 mL, 5.52 g, 43.5 mmol, 2.5 eq) in dry THF (250 mL). The initial precipitate dissolved gradually and the reaction mixture was allowed to stir for 16 h at room temperature. The resulting acid chloride solution was added dropwise to a stirred mixture of the amine 3 (11.9 g, 43.5 mmol, 2.5 eq), TEA (9.71 mL, 7.05 g, 69.7 mmol, 4.0 eq) and $H_2O$ (2.26 mL) in THF (100 mL) at 0° C. (ice/acetone) under a nitrogen atmosphere. The reaction mixture was allowed to warm to room temperature and stirred for a further 2.5 h. Excess THF was removed by rotary evaporation and the resulting residue was partitioned between $H_2O$ (400 mL) and EtOAc (400 mL). The layers were allowed to separate and the aqueous layer was extracted with EtOAc (3×200 mL). The combined organic layers were then washed with saturated $NH_4Cl$ (200 mL), saturated $NaHCO_3$ (200 mL), brine (200 mL) and dried ($MgSO_4$). Filtration and evaporation of the solvent gave the crude product as a dark oil. Purification by flash chromatography (99.7:0.3 v/v $CHCl_3$/MeOH) isolated the pure amide 5 as a light yellow glass (13.3 g, 78%): $^1H$ NMR (400 MHz, $CDCl_3$) δ 7.60 (s, 2H), 6.60 (s, 2H), 5.06 (br s, 2H), 4.44 (br s, 2H), 4.25-4.20 (m, 4H), 4.10-4.08 (m, 2H), 3.80 (s, 6H), 3.64-3.62 (m, 2H), 3.36-3.32 (m, 2H), 3.11-3.08 (m, 2H), 2.36-2.26 (m, 4H), 2.13-2.08 (m, 2H), 1.92 (s, 6H), 0.80 (s, 18H), 0.00 (s×2, 12H); $^{13}C$ NMR (100.6 MHz, $CDCl_3$) δ 171.0, 166.3, 154.5, 148.2, 137.4, 128.0, 127.2, 109.2, 108.5, 72.9, 65.6, 62.6, 57.4, 56.5, 54.8, 33.0, 28.6, 25.8, 21.0, 18.1; MS (ES), m/z (relative intensity) 1000 ([M+Na]+, 39), 978 ([M+H]+, 63), 977 (M+, 100), 812 (13).

(e) 1,1'-[[(Propane-1,3-diyl)dioxy]bis[(2S,4R)-(5-methoxy-2-amino-1,4-phenylene)carbonyl]]bis[2-(tert-butyldimethylsilyloxymethyl)-4-oxyacetylpyrrolidine] (6)

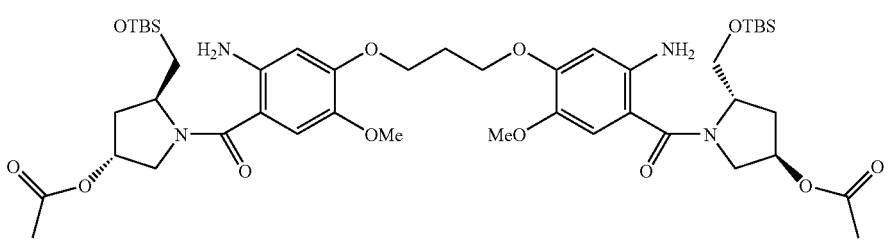

Sodium dithionite (16.59 g, 95.27 mmol, 5 eq) was added to a stirred solution of amide 5 (18.6 g, 19.1 mmol) in $H_2O$ (200 mL) and THF (400 mL). The reaction mixture was allowed to stir for 36 h after which time excess THF was removed by rotary evaporation and the resulting residue was extracted with EtOAc (3×250 mL). The combined organic layers were then washed with $H_2O$ (300 mL), brine (300 mL) and dried ($MgSO_4$). Filtration and evaporation of the solvent yielded the crude product which was purified by flash:chromatography (80:20 v/v hexane/EtOAc then gradient to neat EtOAc) to afford the product 6 as a yellow foam (9.53 g, 55%): $^1H$ NMR (400 MHz, $CDCl_3$) (rotamers) δ 6.70 and 6.67 (s×2, 2H), 6.25 and 6.23 (s×2, 2H), 5.20 (br s, 2H), 4.49 (br s, 4H), 4.16-4.05 (m, 6H), 3.70 (s, 6H), 3.68-3.57 (m, 4H), 2.36-2.27 (m, 4H), 2.12-2.04 (m, 2H), 1.96 (s, 6H), 0.85 (s, 18H), 0.01 and 0.00 (s×2, 12H); $^{13}C$ NMR (100.6 MHz, $CDCl_3$) δ 170.6, 170.0, 141.1, 116.3, 113.1, 102.3, 102.1, 102.0, 66.2, 65.3, 65.2, 57.0, 28.9, 18.2; MS (ES), m/z (relative intensity) 946 (M++29, 43), 933 ([M+16]+, 61), 932 ([M+15]+, 100), 918 ([M+H]+, 72).

(f) 1,1'-[[(Propane-1,3-diyl)dioxy]bis[(2S,4R)-[5-methoxy-1,4-phenylene-2-(2,2,2-trichloroethoxycarbonylamino)]carbonyl]]bis[2-(tert-butyldimethylsilyloxymethyl)-4-oxyacetylpyrrolidine] (7)

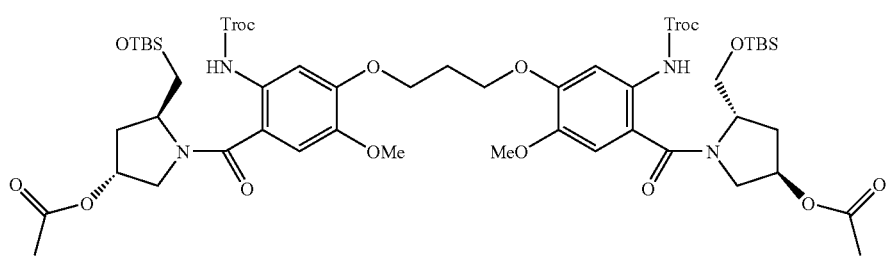

7

A solution of 2,2,2-trichloroethyl chloroformate (3.58 mL, 5.50 g, 26.0 mmol, 2.2 eq) in dry DCM (60 mL) was added dropwise to a solution of anhydrous pyridine (3.82 mL, 3.80 g, 47.2 mmol, 4.0 eq) and bis-aniline 6 (10.8 g, 11.8 mmol) in dry DCM (150 mL) at −10° C. (liq. $N_2$/ethanediol). After 16 h at room temperature, the reaction mixture was washed with saturated $NH_4Cl$ (2×150 mL), saturated $CuSO_4$ (150 mL), $H_2O$ (150 mL), brine (150 mL) and dried ($MgSO_4$). Filtration and evaporation of the solvent yielded a yellow viscous oil which was purified by flash chromatography (70:30 v/v hexane/EtOAc) to afford the product 7 as a white glass (13.8 g, 92%): $^1$H NMR (400 MHz, $CDCl_3$) δ 9.42 (br s, 1H), 7.83 (s, 2H), 6.76 and 6.74 (s×2, 2H), 5.21 (br s, 2H), 4.79 and 4.73 (d×2, 4H, J=12.0 Hz), 4.56 (br s, 2H), 4.26-4.23 (m, 4H), 4.09-4.04 (m, 2H), 3.74 (s, 6H), 3.72-3.68 (m, 2H), 3.60 (br s, 4H), 2.40-2.32 (m, 4H), 2.23-2.08 (m, 2H), 1.95 (s, 6H), 0.85 (s, 18H), 0.01 and 0.00 (s×2, 12H); $^{13}$C NMR (100.6 MHz, $CDCl_3$) δ 170.4, 169.2, 151.9, 151.5, 150.8, 143.4, 132.6, 114.4, 111.7, 95.3, 74.4, 65.5, 65.4, 57.3, 56.4, 32.5, 28.8, 25.8, 21.1, 18.1, 14.9; MS (ES), m/z (relative intensity) 1306 ([M+38]$^+$, 92), 1304 ([M+36]$^+$, 100), 1282 ([M+14]$^+$, 97), 1280 ([M+12]$^+$, 55).

(g) 1,1'-[[(Propane-1,3-diyl)dioxy]bis[(2S,4R)-[5-methoxy-1,4-phenylene-2-(2,2,2-trichloroethoxycarbonylamino)]carbonyl]]bis(2-hydroxymethyl-4-oxyacetylpyrrolidine) (8)

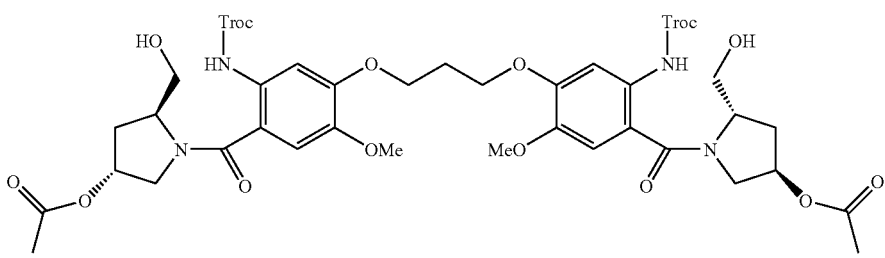

8

A mixture of glacial acetic acid (310 mL) and $H_2O$ (100 mL) was added to a solution of 7 (13.8 g, 10.9 mmol) in THF (250 mL) and was stirred for 16 h at room temperature. The reaction mixture was diluted with DCM (750 mL) and neutralised with saturated $NaHCO_3$ (5 L). The aqueous layer was extracted with DCM (3×500 mL) and the organic layers were combined, washed with brine (1 L) and dried ($MgSO_4$). TLC (60:40 v/v hexane/EtOAc) revealed the complete disappearance of the starting material. Filtration and evaporation of the solvent afforded the crude product which was purified by flash column chromatography (99.7:0.3 v/v $CHCl_3$/MeOH then gradient to 96:4 v/v $CHCl_3$/MeOH) to provide the product 8 as a white glass (11.6 g, >100%): $^1$H NMR (500 MHz, $CDCl_3$) δ 8.92 (br s, 2H), 7.55 (s, 1H), 6.71 (s, 1H), 5.18 (br s, 2H), 4.78 (d, 2H, J=12.0 Hz), 4.72 (d, 2H, J=12.0 Hz), 4.50 (br s, 2H), 4.22-4.19 (m, 4H), 4.00 (br s, 2H), 3.78 (s, 6H), 3.76-3.52 (m, 6H), 2.32-2.30 (m, 2H), 2.21-2.17 (m, 2H), 2.09-2.04 (m, 2H) 1.94 (s, 6H); $^{13}$C NMR (125.8 MHz, $CDCl_3$) δ 170.4, 152.2, 149.8, 145.0, 111.3, 106.5, 95.6, 74.4, 72.5, 65.4, 64.1, 58.7, 56.5, 56.3, 33.6, 29.1, 21.1.

(h) 1,1'-[[(Propane-1,3-diyl)dioxy]bis[(11S,11aS, 2R)-10-(2,2,2-trichloroethoxycarbonyl)-11-hydroxy-7-methoxy-2-oxyacetyl-1,2,3,10,11,11a-hexahydro-5H-pyrrolo[2,1-c][1,4]-benzodiazepin-5-one]] (9)

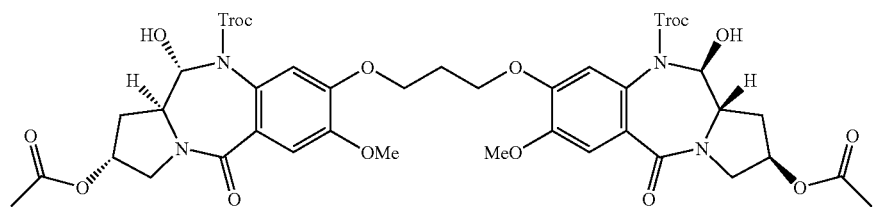

TEMPO (0.69 g, 4.42 mmol, 0.4 eq) and BAIB (15.7 g, 48.7 mmol, 4.4 eq) were added to a stirred solution of diol 8 (11.5 g, 11.1 mmol) in DCM (150 mL). The reaction mixture was allowed to stir for 2 h and diluted with DCM (400 mL), washed with saturated $NaHSO_3$ (500 mL), saturated $NaHCO_3$ (500 mL), brine (200 mL) and dried ($MgSO_4$). Filtration and evaporation of the solvent afforded the crude product which was purified by flash column chromatography (99.9:0.1 v/v $CHCl_3$/MeOH then gradient to 99.7:0.3 v/v $CHCl_3$/MeOH) to provide the product 9 as a light yellow glass (4.43 g, 39%): $^1$H NMR (400 MHz, $CDCl_3$) 7.28 (s, 2H, H6), 6.84 (s, 2H, H9), 5.68 (d, 2H, J=9.1 Hz, H11), 5.37-5.35 (m, 2H, H2), 5.18 (d, 2H, J=12.0 Hz, Troc $CH_2$), 4.32-4.21 (m, 6H, $OCH_2CH_2CH_2O$, Troc $CH_2$), 4.03 (dd, 2H, J=13.2, 2.6 Hz, H3), 3.92 (s, 6H, $OCH_3$×2), 3.39-3.69 (m, 4H, H3 and H11a), 2.39-2.35 (m, 6H, $OCH_2CH_2CH_2O$ and H1), 2.03 (s, 6H, $CH_3CO_2$×2); $^{13}$C NMR (100.6 MHz, $CDCl_3$) δ 170.4 ($CH_3CO_2$), 167.4 ($C_{quat}$), 154.3 ($C_{quat}$), 150.5 ($C_{quat}$), 149.1 ($C_{quat}$), 127.4 ($C_{quat}$), 124.9 ($C_{quat}$), 114.1 (C9), 110.9 (C6), 95.0 (Troc $CCl_3$), 87.5 (C11), 75.0 (Troc $CH_2$), 71.4 (C2), 65.5 ($OCH_2CH_2CH_2O$), 58.4 (C11a), 56.1 ($OCH_3$), 51.1 (C3), 35.8 (C1), 29.1 ($OCH_2CH_2CH_2O$), 21.0 ($CH_3CO_2$); MS (ES), m/z (relative intensity) 1058 ([M+Na]$^+$, 100).

(i) 1,1'-[[(Propane-1,3-diyl)dioxy]bis[(11S,11aS, 2R)-10-(2,2,2-trichloroethoxycarbonyl)-11-(tert-butyldimethylsilyloxy)-7-methoxy-2-oxyacetyl-1,2,3,10,11,11a-hexahydro-5H-pyrrolo[2,1-c][1,4]benzodiazepin-5-one]] (10)

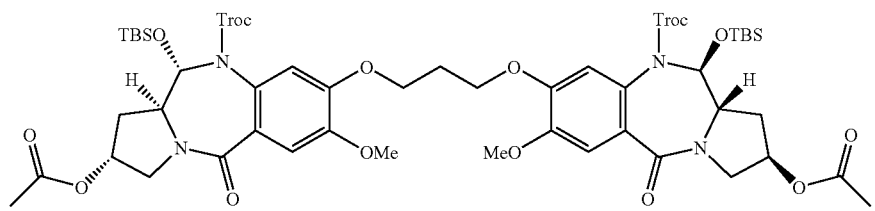

TBSOTf (2.70 mL, 3.10 g, 11.7 mmol, 3.0 eq) was added to a stirred solution of bis-alcohol 9 (4.05 g, 3.91 mmol) and 2,6-lutidine (1.82 mL, 1.68 g, 15.6 mmol, 4.0 eq) in DCM (50 mL). The reaction mixture was allowed to stir for 2.5 h and diluted with DCM (150 mL), washed with saturated $CuSO_4$ (2×100 mL), saturated $NaHCO_3$ (100 mL), brine (200 mL) and dried ($MgSO_4$). Filtration and evaporation of the solvent afforded the crude product which was purified by flash column chromatography (99.9:0.1 v/v $CHCl_3$/MeOH) to provide the product 10 as a white glass (5.05 g, >100%): $^1$H NMR (400 MHz, $CDCl_3$) δ 7.05 (s, 2H, H6), 6.52 (s, 2H, H9), 5.53 (d, 2H, J=9.0 Hz, H11), 5.14 (br s, 2H, H2), 4.99 (d, 2H, J=12.0 Hz, Troc $CH_2$), 4.06-3.87 (m, 8H, $OCH_2CH_2CH_2O$, Troc $CH_2$ and H11a), 3.71 (s, 6H, $OCH_3$×2), 3.48-3.43 (m, 4H, H3), 2.21-2.11 (m, 4H, $OCH_2CH_2CH_2O$ and H1), 2.03-1.96 (m, 2H, H1), 1.81 (s, 6H, $CH_3CO_2$×2), 0.63 (s, 18H, TBS $CH_3$×6), 0.00 (s×2, 12H, TBS $CH_3$×4); $^{13}$C NMR (100.6 MHz, $CDCl_3$) δ 170.3 ($CH_3CO_2$), 167.9 ($C_{quat}$), 153.6 ($C_{quat}$), 150.4 ($C_{quat}$), 149.2 ($C_{quat}$), 127.9 ($C_{quat}$), 125.5 ($C_{quat}$), 113.9 (C9), 110.7 (C6), 95.2 (Troc $CCl_3$), 88.2 (C11), 74.7 (Troc $CH_2$), 71.7 (C2), 65.0 ($OCH_2CH_2CH_2O$), 60.5 (C11a), 56.1 ($OCH_3$), 51.2 (C3), 36.2 (C1), 28.8 ($OCH_2CH_2CH_2O$), 25.6 (TBS $CH_3$), 21.0 ($CH_3CO_2$), 17.8 (TBS $C_{quat}$), 14.2 and 14.1 (TBS $CH_3$); MS (ES), m/z (relative intensity) 1285 ([M+21]$^+$, 100), 1265 ([M+H]$^+$, 75).

(j) 1,1'-[[(Propane-1,3-diyl)dioxy]bis[(11S,11aS, 2R)-10-(2,2,2-trichloroethoxycarbonyl)-11-(tert-butyldimethylsilyloxy)-7-methoxy-2-hydroxy-1,2,3, 10,11,11a-hexahydro-5H-pyrrolo[2,1-c][1,4] benzodiazepin-5-one]] (11)

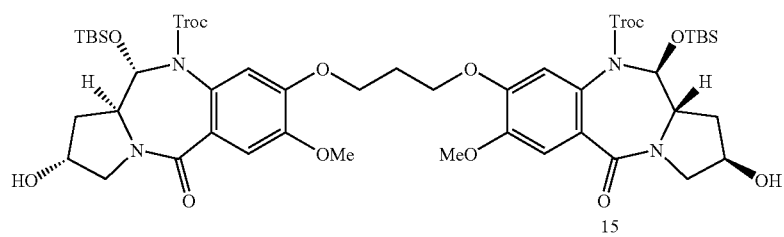

A solution of $K_2CO_3$ (93 mg, 0.67 mmol, 5.0 eq) in $H_2O$ (2 mL) was added dropwise to a stirred solution of acetate 10 (170 mg, 0.13 mmol) in MeOH (3 mL). The initial colorless solution eventually turned yellow and the formation of a white precipitate was observed. The reaction mixture was allowed to stir for 16 h when TLC (95:5 v/v $CHCl_3$/MeOH) showed the complete consumption of the starting material. Excess solvent was removed by rotary evaporation and the mixture was carefully neutralized with 1N HCl to pH 7. The resulting mixture was extracted with EtOAc (3×25 mL) and the combined organic layers were then washed with brine (40 mL) and dried ($MgSO_4$). Filtration and removal of the solvent afforded the product 11 as a white glass (151 mg, 95%): $^1$H NMR (400 MHz, $CDCl_3$) δ 6.94 (s, 2H, H6), 6.52 (s, 2H, H9), 5.53 (d, 2H, J=9.0 Hz, H11), 5.00 (d, 2H, J=12.0 Hz, Troc $CH_2$), 4.36-4.35 (m, 2H, H2), 4.06-3.82 (m, 8H, $OCH_2CH_2CH_2O$, Troc $CH_2$ and H3), 3.61 (s, 6H, $OCH_3$×2), 3.54-3.48 (m, 2H, H11a), 3.39-3.34 (m, 2H, H3), 2.96 and 2.95 (br s×2, 2H, OH×2), 2.21-2.20 (m, 2H, $OCH_2CH_2CH_2O$), 2.19-2.08 (m, 2H, H1), 1.90-1.74 (m, 2H, H1), 0.64 (s, 18H, TBS $CH_3$×6), 0.00 (s, 12H, TBS $CH_3$×4); $^{13}$C NMR (100.6 MHz, $CDCl_3$) δ 168.5 ($C_{quat}$), 153.6 ($C_{quat}$), 150.3 ($C_{quat}$), 149.1 ($C_{quat}$), 127.9 ($C_{quat}$), 125.4 ($C_{quat}$), 113.9 (C9), 110.7 (C6), 95.2 (Troc $CCl_3$), 88.3 (C11), 74.7 (Troc $CH_2$), 69.4 (C2), 65.0 ($OCH_2CH_2CH_2O$), 60.9 (C11a), 55.9 ($OCH_3$), 54.1 (C3), 38.8 (C1), 28.9 ($OCH_2CH_2CH_2O$), 25.6 (TBS $CH_3$), 17.8 (TBS $C_{quat}$); MS (ES), m/z (relative intensity) 1196 ([M+16]$^+$, 100), 1181 ([M+H]$^+$, 82).

(k) 1,1'-[[(Propane-1,3-diyl)dioxy]bis[(11S,11aS)-10-(2,2,2-trichloroethoxycarbonyl)-1'-(tert-butyldimethylsilyloxy)-7-methoxy-2-oxo-1,2,3,10,11,11a-hexahydro-5H-pyrrolo[2,1-c][1,4]benzodiazepin-5-one]] (12)

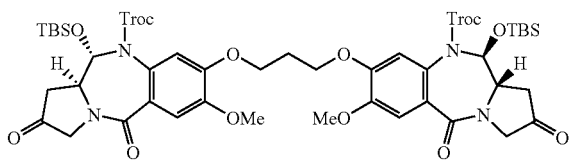

A solution of anhydrous DMSO (0.82 mL, 0.90 g, 11.5 mmol, 6.0 eq) in dry DCM (20 mL) was added dropwise to a stirred solution of oxalyl chloride (2.88 mL of a 2 M solution in DCM, 5.76 mmol, 3.0 eq) under a nitrogen atmosphere at −60° C. (liq $N_2$/$CHCl_3$). After stirring at −55° C. for 1.5 h, a solution of the substrate 11 (2.26 g, 1.92 mmol) in dry DCM (30 mL) was added dropwise to the reaction mixture, which was then stirred for a further 2 h at −45° C. A solution of TEA (10.8 mL, 7.82 g; 71.7 mmol, 4.2 eq) in dry DCM (90 mL) was added dropwise to the mixture and stirred for a further 30 min. The reaction mixture was left to warm to 0° C., washed with cold 1 N HCl (2×50 mL), $H_2O$ (50 mL), brine (50 mL) and dried ($MgSO_4$). Filtration and evaporation of the solvent in vacuo afforded the crude product which was purified by flash column chromatography (70:30 v/v hexane/EtOAc then gradient to 40:60 v/v hexane/EtOAc) to afford carbinolamine 12 as a white glass (1.62 g, 72%): $^1$H NMR (400 MHz, $CDCl_3$) δ 7.02 (s, 2H, H6), 6.54 (s, 2H, H9), 5.59 (d, 2H, J=9.2 Hz, H11), 4.98 (d, 2H, J=12.0 Hz, Troc $CH_2$), 4.09-3.86 (m, 8H, $OCH_2CH_2CH_2O$, Troc $CH_2$ and H3), 3.75-3.66 (m, 10H, $OCH_3$×2, H11a, and H3), 2.72 (dd, 2H, J=10.2, 19.6 Hz, H1), 2.82 (dd, 2H, J=2.6, 19.6 Hz, H1), 2.22-2.19 (m, 2H, $OCH_2CH_2CH_2O$), 0.63 (s, 18H, TBS $CH_3$×6), 0.00 (s×2, 12H, TBS $CH_3$×4); $^{13}$C NMR (100.6 MHz, $CDCl_3$) δ 207.7 (C2), 168.0 ($C_{quat}$), 153.7 ($C_{quat}$), 150.7 ($C_{quat}$), 149.4 ($C_{quat}$), 127.8 ($C_{quat}$), 124.6 ($C_{quat}$), 114.0 (C9), 110.6 (C6), 95.1 (Troc $CCl_3$), 87.4 (C11), 74.8 (Troc $CH_2$), 65.0 ($OCH_2CH_2CH_2O$), 58.9 (C11a), 56.1 ($OCH_3$), 53.0 (C3), 40.3 (C1), 28.8 ($OCH_2CH_2CH_2O$), 25.6 (TBS $CH_3$), 17.8 (TBS $C_{quat}$); MS (ES), m/z (relative intensity) 1224 ([M+48]$^+$, 100), 1210 ([M+34]$^+$, 60), 1199 ([M+Na]$^+$, 35), 1192 ([M+16]$^+$, 40), 1176 (M$^+$, 18).

(l) 1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-[[(trifluoromethyl)sulfonyl]oxy]-1,10,11,11a-tetrahydro-5H-pyrrolo[2,1-c][1,4]benzodiazepin-5-one]] (13)

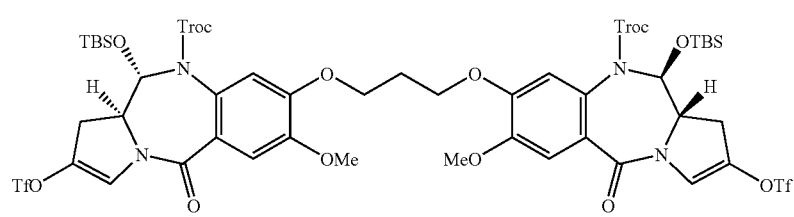

Anhydrous triflic anhydride (3.09 mL, 5.19 g, 18.4 mmol, 22 eq) taken from a freshly opened ampule was added rapidly in one portion to a vigorously stirred solution of ketone 12 (0.98 g, 0.84 mmol) and anhydrous pyridine (1.49 mL, 1.46 g, 18.4 mmol, 22 eq) in dry DCM (50 mL) at room temperature under a nitrogen atmosphere. The initial precipitate dissolved gradually and the solution eventually turned a dark red colour. The reaction mixture was allowed to stir for 4.5 h when TLC (80:20 v/v EtOAc/hexane) revealed the complete consumption of the starting material. The mixture was poured into cold saturated NaHCO$_3$ (60 mL) and extracted with DCM (3×80 mL). The combined organic layers were then washed with saturated CuSO$_4$ (2×125 mL), brine (125 mL) and dried (MgSO$_4$). Filtration and evaporation of the solvent afforded the crude product which was purified by flash column chromatography (80:20 v/v hexane/EtOAc) to afford triflate 13 as a light yellow glass (0.74 mg, 61%): $[\alpha]_D^{25}=+46.0°$ (c=0.33, CHCl$_3$); $^1$H NMR (400 MHz, CDCl$_3$) δ 7.23 (s, 2H, H6), 7.19 (s, 2H, H3), 6.77 (s, 2H, H9), 5.94 (d, 2H, J=8.9 Hz, H11), 5.23 (d, 2H, J=12.0 Hz, Troc CH$_2$), 4.31-4.28 (m, 2H, OCH$_2$CH$_2$CH$_2$O), 4.18 (d, 2H, J=12.2 Hz, Troc CH$_2$), 4.15-4.13 (m, 2H, OCH$_2$CH$_2$CH$_2$O), 3.95-3.91 (m, 8H, OCH$_3$×2, H11a), 3.35 (dd, 2H, J=11.0, 16.6 Hz, H1), 2.84 (d, 2H, J=16.6 Hz, H1), 2.46-2.44 (m, 2H, OCH$_2$CH$_2$CH$_2$O), 0.89 (s, 18H, TBS CH$_3$×6), 0.29 and 0.26 (s×2, 12H, TBS CH$_3$×4); $^{13}$C NMR (100.6 MHz, CDCl$_3$) δ 164.9 (C$_{quat}$), 153.6 (C$_{quat}$), 151.0 (C$_{quat}$), 149.5 (C$_{quat}$), 136.0 (C$_{quat}$), 127.7 (C$_{quat}$), 123.9 (C$_{quat}$), 121.0 (C3), 114.0 (C9), 110.9 (C6), 95.1 (Troc CCl$_3$), 86.3 (C11), 74.8 (Troc CH$_2$), 65.0 (OCH$_2$CH$_2$CH$_2$O), 60.6 (C11a), 56.2 (OCH$_3$), 34.4 (C1), 28.8 (OCH$_2$CH$_2$CH$_2$O), 25.6 (TBS CH$_3$), 17.8 (TBS C$_{quat}$); IR (CHCl$_3$) 3020, 2957, 2860, 1725, 1674, 1651, 1604, 1516, 1466, 1454, 1431, 1409, 1329, 1312, 1274, 1216, 1138, 1113, 1083, 1042, 1006, 900, 840, 757, 668, 646, 610 cm$^{-1}$; MS (ES), m/z (relative intensity) 1461 ([M+21]$^+$, 100), 1440 (M$^+$, 55).

(m) 1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-(p-methoxybenzene)-1,10,11,11a-tetrahydro-5H-pyrrolo[2,1-c][1,4]benzodiazepin-5-one]] (14)

A solution of TEA (0.20 mL, 148 mg, 1.46 mmol, 6.0 eq) in H$_2$O (1.5 mL) and EtOH (10 mL) was added to a solution of triflate 13 (350 mg, 0.24 mmol) in toluene (10 mL) at room temperature. To this mixture 4-methoxybenzeneboronic acid (96 mg, 0.63 mmol, 2.6 eq) and Pd(PPh$_3$)$_4$ (11 mg, 9 μmol, 0.04 eq) were added. The reaction mixture was allowed to stir for 15 min when TLC (80:20 v/v EtOAc/hexane) revealed the complete consumption of the starting material. Excess solvent was removed and the residue was dissolved in EtOAc (25 mL), washed with H$_2$O (15 mL), brine (15 mL) and dried (MgSO$_4$). Filtration and evaporation of solvent afforded the crude product which was purified by flash column chromatography (80:20 v/v hexane/EtOAc then gradient to 50:50 v/v hexane/EtOAc) to afford 14 as a yellow glass (286 mg, 87%): $^1$H NMR (400 MHz, CDCl$_3$) δ 7.38 (s, 2H, H3), 7.32-7.28 (m, 6H, H6 and H13), 6.92 (d, 4H, J=8.7 Hz, H14), 6.81 (s, 2H, H9), 5.93 (d, 2H, J=8.8 Hz, H11), 5.24 (d, 2H, J=12.0 Hz, Troc CH$_2$), 4.34-4.29 (m, 2H, OCH$_2$CH$_2$CH$_2$O), 4.20-4.11 (m, 4H, Troc CH$_2$ and OCH$_2$CH$_2$CH$_2$O), 4.00-3.96 (m, 8H, H11a and OCH$_3$×2), 3.84 (s, 6H, OCH$_3$×2), 3.36 (dd, 2H, J=10.8, 16.6 Hz, H1), 2.85 (d, 2H, J=16.5 Hz, H1), 2.48-2.45 (m, 2H, OCH$_2$CH$_2$CH$_2$O), 0.93 (s, 18H, TBS CH$_3$×6), 0.30 and 0.27 (s×2, 12H, TBS CH$_3$×4); $^{13}$C NMR (100.6 MHz, CDCl$_3$) δ 162.5 (C$_{quat}$), 161.3 (C$_{quat}$), 159.2 (C$_{quat}$), 151.1 (C$_{quat}$), 148.1 (C$_{quat}$), 140.3 (C$_{quat}$), 126.2 (C13), 126.0 (C$_{quat}$), 123.2 (C$_{quat}$), 121.9 (C3), 119.3 (C$_{quat}$), 114.3 (C6), 111.9 (C14), 111.2 (C9), 95.2 (Troc CCl$_3$), 87.3 (C11), 74.8 (Troc CH$_2$), 65.0 (OCH$_2$CH$_2$CH$_2$O), 61.5 (C11a), 56.1 and 55.3 (OCH$_3$), 35.3 (C1), 28.8 (OCH$_2$CH$_2$CH$_2$O), 25.7 (TBS CH$_3$), 17.9 (TBS C$_{quat}$); MS (ES), m/z (relative intensity) 1357 (M$^+$, 63), 1114 (48), 955 (59), 919 (78).

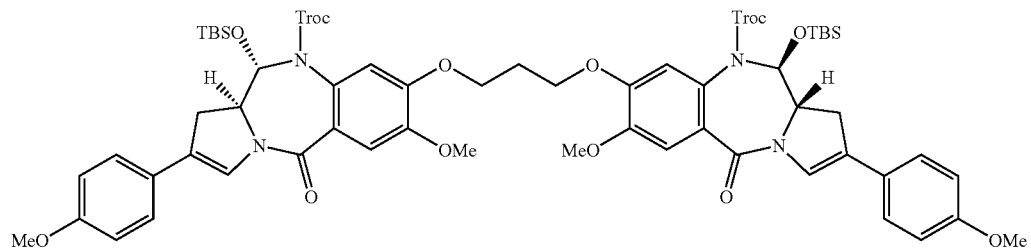

14

(n) 1,1'-[[(Propane-1,3-diyl)dioxy]bis[(11aS)-7-methoxy-2-(p-methoxybenzene)-1,11a-dihydro-5H-pyrrolo[2,1-c][1,4]benzodiazepine-5-one]] (ZC-207)

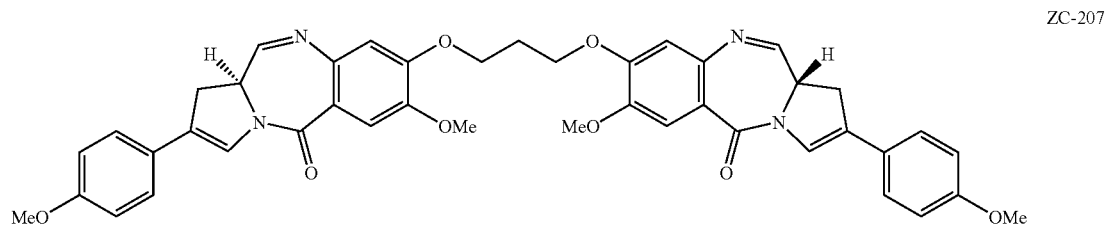 [SMILES: COc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

ZC-207

10% Cd/Pd couple (461 mg, 3.73 mmol, 20 eq) was added to a rapidly stirring mixture of 14 (253 mg, 0.19 mmol), THF (5 mL) and 1 N NH$_4$OAc (5 mL). The reaction mixture was allowed to stir for 1.5 h when TLC showed the complete consumption of the starting material. The solids were filtered and rinsed with H$_2$O and DCM. The aqueous layer was extracted with DCM (3×30 mL) and the organic extracts were combined, washed with brine (50 mL) and dried (MgSO$_4$). Filtration and evaporation of solvent afforded the crude product which was purified by flash column chromatography (99.9:0.1 v/v CHCl$_3$/MeOH then gradient to 95:5 v/v CHCl$_3$/MeOH) to afford ZC-207 as a yellow glass (132 mg, 96%): $[\alpha]_D^{20}$=+880.0° (c=0.22, CHCl$_3$); $^1$H NMR (400 MHz, CDCl$_3$) δ 7.79 (d, 2H, J=3.9 Hz, H11), 7.44 (s, 2H, H6), 7.30 (s, 2H, H3), 7.24 (d, 4H, J=8.7 Hz, H13), 6.81 (d, 4H, J=8.7 Hz, H14), 6.79 (s, 2H, H9), 4.30-4.18 (m, 6H, OCH$_2$CH$_2$CH$_2$O and H11a), 3.86 (s, 6H, OCH$_3$×2), 3.74 (s, 6H, OCH$_3$×2), 3.48 (dd, 2H, J=11.8, 16.2 Hz, H1), 2.85 (d, 2H, J=16.2 Hz, H1), 2.38-2.32 (m, 2H, OCH$_2$CH$_2$CH$_2$O); $^{13}$C NMR (62.9 MHz, CDCl$_3$) δ 162.5 (C11), 161.3 ($C_{quat}$), 159.2 ($C_{quat}$), 151.1 ($C_{quat}$), 148.1 ($C_{quat}$), 140.3 ($C_{quat}$), 126.2 (C13), 126.0 ($C_{quat}$), 123.2 ($C_{quat}$), 121.9 (C3), 114.3 (C14), 111.9 (C9), 111.2 (C6), 65.4 (OCH$_2$CH$_2$CH$_2$O), 56.2 and 55.3 (OCH$_3$), 53.8 (C11a), 35.6 (C1), 28.9 (OCH$_2$CH$_2$CH$_2$O); MS (ES), m/z (relative intensity) 741 (M$^+$, 43), 660 (71).

(o) 1,1'[[(Propane-1,5-diyl)dioxy]bis[(11aS)-11-sulpho-7-methoxy-2-(4-methoxyphenyl)-1,10,11,11a-tetrahydro-5H-pyrrolo[2,1-c][1,4]benzodiazepin-5-one]] sodium salt (ZC-423)

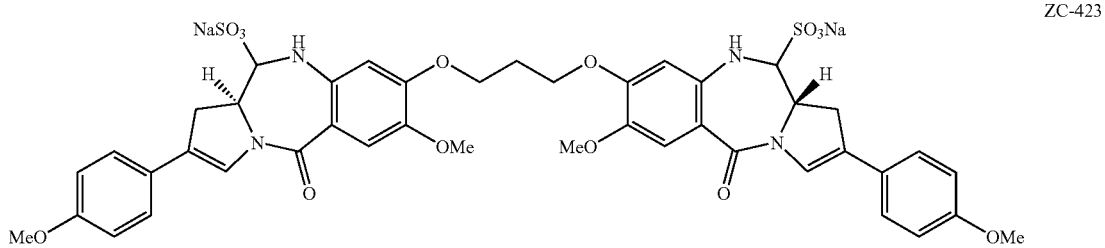

ZC-423

A solution of sodium bisulphite (6.74 mg, 65 μmol) in water (1.5 mL) was added to a stirred solution of ZC-207 (24.01 mg, 32 μmol) in dichloromethane (1.5 mL). The reaction mixture was allowed to stir vigorously for 2 h, after which time the organic and aqueous layers were separated. TLC analysis (eluent-EtOAc) of the aqueous phase revealed absence of ZC-207 and presence of baseline material with strong uv absorption. The aqueous layer was lyophilised to provide the bisulphite adduct ZC-423 as a white solid (17 mg, 55%): $^1$H NMR (400 MHz, d$_6$-DMSO) δ 7.42 (s, 2H, H-3), 7.38 (d, 4H, J=8.72 Hz, 2'-H), 7.05 (s, 2H, H-6), 6.92 (d, 4H, J=8.92 Hz, 3'-H), 6.52 (s, 2H, H-9), 5.27 (s, 2H, NH), 4.35-4.25 (m, 2H, H11a), 4.15-4.05 (m, 4H, OCH$_2$CH$_2$CH$_2$O), 3.95 (d, 2H, J=10.4 Hz, H11), 3.77 (s, 6H, OMe), 3.72 (s, 6H, OMe), 3.55-3.45 (m, 2H, H1), 3.30-3.15 (m, 2H, H1), 2.25-2.15 (m, 2H, OCH$_2$CH$_2$CH$_2$O).

Example 2

(a) 1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-(naphthalen-2-yl)-1,10,11,11a-tetrahydro-5H-pyrrolo[2,1-c][1,4]benzodiazepin-5-one]] (17)

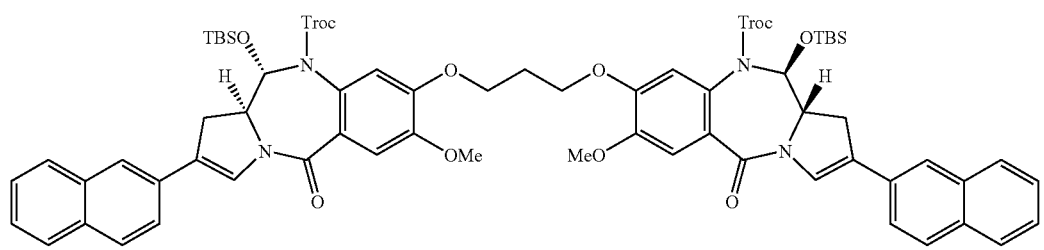

A solution of TEA (0.15 mL, 1.05 mmol, 6.0 eq) in $H_2O$ (1 mL) and EtOH (10 mL) was added to a solution of 13 (251 mg, 0.17 mmol) in toluene (6 mL) at room temperature. To this mixture 2-naphthaleneboronic acid (77.9 mg, 0.45 mmol, 2.6 eq) and $Pd(PPh_3)_4$ (8.0 mg, 7 mmol, 0.04 eq) were added. The reaction mixture was heated at 100° C. under microwave irradiation for 20 minutes when TLC (80:20 v/v EtOAc/hexane) revealed complete consumption of the starting material. Excess solvent was removed and the residue was dissolved in EtOAc (20 mL), washed with $H_2O$ (15 mL), brine (15 mL) and dried ($MgSO_4$). Filtration and evaporation of solvent afforded the crude product which was purified by flash column chromatography (80:20 v/v hexane/EtOAc then gradient to 50:50 v/v hexane/EtOAc) to afford 17 as a yellow glass (191 mg, 81%): $^1H$ NMR (400 MHz, $CDCl_3$) δ 7.32-7.29 (m, 6H, $H_{arom}$), 7.61-7.58 (m, 6H, $H_{arom}$), 7.52-7.42 (m, 4H, H3 and $H_{arom}$), 7.30 (s, 2H, H6), 6.81 (s, 2H, H9), 5.98 (d, 2H, J=8.8 Hz, H11), 5.24 (d, 2H, J=12.0 Hz, Troc $CH_2$), 4.35-4.30 (m, 2H, $OCH_2CH_2CH_2O$), 4.20-4.13 (m, 4H, Troc $CH_2$ and $OCH_2CH_2CH_2O$), 4.08-4.00 (m, 2H, H11a), 3.97 (s, 6H, $OCH_3$×2), 3.50 (dd, 2H, J=10.8, 16.6 Hz, H1), 2.98 (d, 2H, J=16.5 Hz, H1), 2.50-2.48 (m, 2H, $OCH_2CH_2CH_2O$), 0.94 (s, 18H, TBS $CH_3$×6), 0.30 and 0.28 (s×2, 12H, TBS $CH_3$×4).

(b) 1,1'-[[(Propane-1,3-diyl)dioxy]bis[(11aS)-7-methoxy-2-(naphthalen-2-yl)-1,11a-dihydro-5H-pyrrolo[2,1-c][1,4]benzodiazepine-5-one]] (18)

10% Cd/Pb couple (455 mg, 3.71 mmol, 26 eq) was added to a rapidly stirring mixture of 17 (190 mg, 0.14 mmol), THF (3.2 mL) and 1 N $NH_4OAc$ (3.2 mL). The reaction mixture was allowed to stir for 6.5 hours when TLC showed the incomplete consumption of the starting material and formation of side products. The solids were filtered and rinsed with $H_2O$ and MeOH. Excess solvent was removed and the residue was diluted with $H_2O$ (25 mL) and DCM (25 mL). The aqueous layer was extracted with DCM (3×25 mL) and the organic extracts were combined, washed with brine (50 mL) and dried ($MgSO_4$). Filtration and evaporation of solvent afforded the crude product which was purified by flash column chromatography (99:1 v/v $CHCl_3$/MeOH then gradient to 98:2 v/v $CHCl_3$/MeOH) to afford 18 as a yellow glass (38 mg, 36%): $^1H$ NMR (400 MHz, $CDCl_3$) δ 7.85 (d, 2H, J=3.9 Hz, H11), 7.77-7.65 (m, 6H, $H_{arom}$), 7.59-7.50 (m, 6H, H3 and $H_{arom}$), 7.47 (s, 2H, H6), 7.44-7.33 (m, 4H, $H_{arom}$), 6.82 (s, 2H, H9), 4.42-4.32 (m, 2H, H11a), 4.31-4.14 (m, 4H, $OCH_2CH_2CH_2O$), 3.89 (s, 6H, $OCH_3$×2), 3.69-3.56 (m, 2H, H1), 3.50-3.37 (m, 2H, H1), 2.45-2.29 (m, 2H, $OCH_2CH_2CH_2O$).

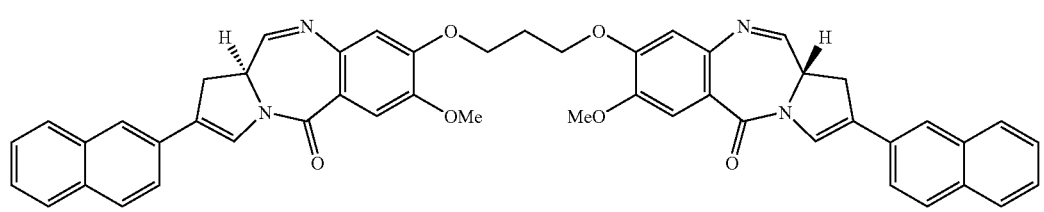

(c) 1,1'-[[(Propane-1,3-diyl)dioxy]bis[(11aS)-11-sulpho-7-methoxy-2-(naphthalen-2-yl)-1,10,11,11a-tetrahydro-5H-pyrrolo[2,1-c][1,4]benzodiazepin-5-one]] sodium salt (19)

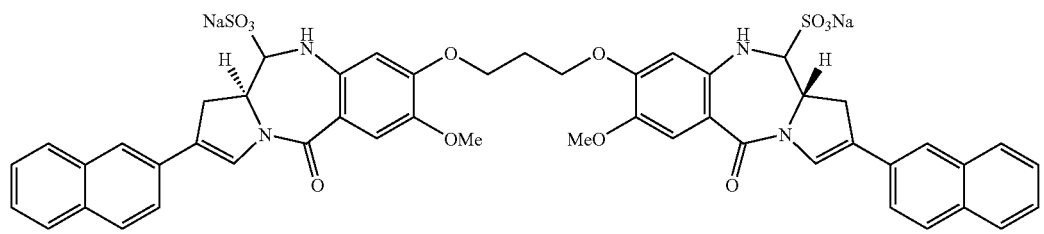

19

A solution of sodium bisulphite (6.67 mg, 0.064 mmol, 2.0 equiv.) in H$_2$O (1.5 mL) was added to a solution of compound 18 (25 mg, 0.032 mmol) in dry DCM (1.5 mL). The reaction mixture was allowed to stir for 5 hours. The reaction mixture was diluted with DCM (5 mL) and H$_2$O (5 mL). The aqueous layer was separated (without shaking the separating funnel) and dried under the freeze dryer to afford 19 as a lightweight white solid (7 mg, 22%): $^1$H NMR (400 MHz, DMSO) δ 7.78-7.72 (m, 8H, H$_{arom}$), 7.68 (s, 2H, H3), 7.59-7.27 (m, 6H, H$_{arom}$), 6.92 (s, 2H, H6), 6.41 (s, 2H, H9), 5.21 (d, 2H, J=5.2 Hz, NH), 4.38-4.31 (m, 2H, H11a), 4.12-3.96 (m, 4H, OCH$_2$CH$_2$CH$_2$O), 3.87 (d, 2H, J=10.4 Hz, H11), 3.70 (s, 3H, OCH$_3$), 3.61 (s, 3H, OCH$_3$), 3.40-3.12 (m, 4H, H1), 2.28-2.22 (m, 2H, OCH$_2$CH$_2$CH$_2$O).

Example 3

(a) 1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-(thiophen-2-yl)-1,10,11,11a-tetrahydro-5H-pyrrolo[2,1-c][1,4]benzodiazepin-5-one]] (20)

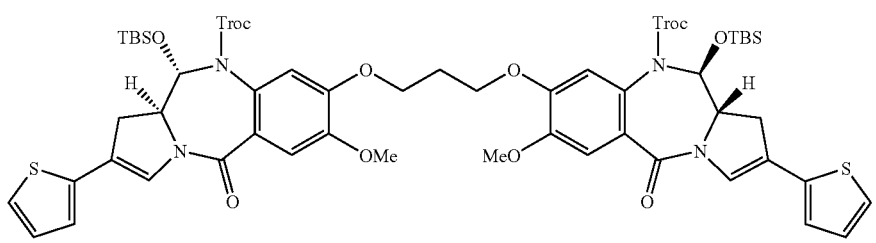

20

A solution of TEA (0.11 mL, 0.82 mmol, 6.0 eq) in H$_2$O (0.8 mL) and EtOH (5 mL) was added to a solution of 13 (197 mg, 0.14 mmol) in toluene (5 mL). To this mixture thiophene-2-boronic acid (45.5 mg, 0.36 mmol, 2.6 eq) and Pd(PPh$_3$)$_4$ (6.3 mg, 5 μmol, 0.04 eq) were added. The reaction mixture was allowed to stir at room temperature for 3 hours when TLC (80:20 v/v EtOAc/hexane) revealed complete consumption of the starting material. Excess solvent was removed and the residue was dissolved in EtOAc (20 mL), washed with H$_2$O (15 mL), brine (15 mL) and dried (MgSO$_4$). Filtration and evaporation of solvent afforded the crude product which was purified by flash column chromatography (80:20 v/v hexane/EtOAc) to afford 20 as a yellow glass (168 mg, 94%): $^1$H NMR (400 MHz, CDCl$_3$) δ 7.32 (s, 2H, H3), 7.26 (s, 2H, H6), 7.24-7.19 (m, 2H, H$_{arom}$), 7.04-6.79 (m, 2H, H$_{arom}$), 6.94-6.88 (m, 2H, H$_{arom}$), 6.78 (s, 2H, H9), 5.92 (d, 2H, J=8.9 Hz, H11), 5.24 (d, 2H, J=12.0 Hz, Troc CH$_2$), 4.36-4.25 (m, 2H, OCH$_2$CH$_2$CH$_2$O), 4.19-4.08 (m, 4H, Troc CH$_2$ and OCH$_2$CH$_2$CH$_2$O), 4.02-3.87 (m, 8H, H11a and OCH$_3$×2), 3.37 (dd, 2H, J=10.8, 16.6 Hz, H1), 2.85 (d, 2H, J=16.5 Hz, H1), 2.52-2.37 (m, 2H, OCH$_2$CH$_2$CH$_2$O), 0.91 (s, 18H, TBS CH$_3$×6), 0.28 and 0.25 (s×2, 12H, TBS CH$_3$×4).

(b) 1,1'-[[(Propane-1,3-diyl)dioxy]bis[(11aS)-7-methoxy-2-(thiophen-2-yl)-1,11a-dihydro-5H-pyrrolo[2,1-c][1,4]benzodiazepine-5-one]] (21)

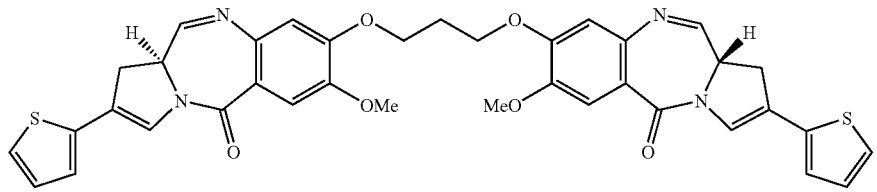

10% Cd/Pb couple (288 mg, 2.35 mmol, 20 eq) was added to a rapidly stirring mixture of 20 (154 mg, 0.12 mmol), THF (3 mL) and 1 N NH$_4$OAc (3 mL). The reaction mixture was allowed to stir for 3 hours when TLC showed complete consumption of the starting material. The solids were filtered and rinsed with H$_2$O and DCM. The aqueous layer was extracted with DCM (3×15 mL) and the organic extracts were combined, washed with brine (40 mL) and dried (MgSO$_4$). Filtration and evaporation of solvent afforded the crude product which was purified by flash column chromatography (99:1 v/v CHCl$_3$/MeOH then gradient to 98:2 v/v CHCl$_3$/MeOH) to afford 21 as a yellow glass (59 mg, 72%): $^1$H NMR (400 MHz, CDCl$_3$) δ 7.90 (d, 2H, J=4.0 Hz, H11), 7.51 (s, 2H, H6), 7.36 (s, 2H, H3), 7.22 (d, 2H, J=5.2 Hz, H$_{arom}$), 7.02 (dd, 2H, J=3.6, 5.0 Hz, H$_{arom}$), 6.98 (d, 2H, J=3.4 Hz, H$_{arom}$), 6.88 (s, 2H, H9), 4.43-4.23 (m, 6H, H11a and OCH$_2$CH$_2$CH$_2$O), 3.94 (s, 6H, OCH$_3$×2), 3.59 (ddd, 2H, J=2.0, 11.5, 16.0 Hz, H1), 2.85 (ddd, 2H, J=1.5, 5.2, 16.0 Hz, H1), 2.49-2.40 (m, 2H, OCH$_2$CH$_2$CH$_2$O).

(c) 1,1'-[[(Propane-1,3-diyl)dioxy]bis[(11aS)-11-sulpho-7-methoxy-2-(thiophen-2-yl)-1,10,11,11a-tetrahydro-5H-pyrrolo[2,1-c][1,4]benzodiazepin-5-one]] sodium salt (22)

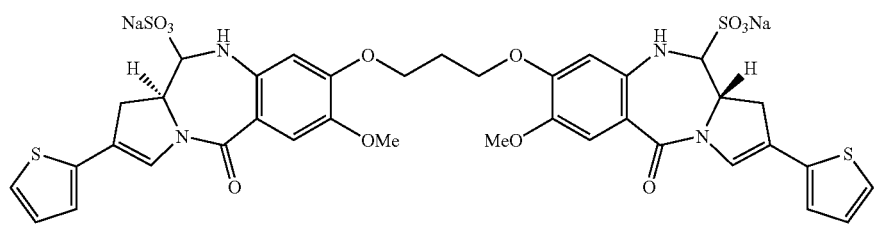

A solution of sodium bisulphite (16.5 mg, 0.159 mmol, 2.0 equiv.) in H$_2$O (3.5 mL) was added to a solution of compound 21 (55.0 mg, 0.079 mmol) in DCM (3.5 mL). The reaction mixture was allowed to stir for 4 hours. TLC (EtOAc) revealed complete consumption of the starting material and a product spot at the base line. The reaction mixture was diluted with DCM and H$_2$O. The aqueous layer was separated (without shaking the separating funnel) and dried under the freeze dryer to afford 22 as a lightweight yellow solid (53.9 mg, 75%): $^1$H NMR (400 MHz, DMSO) δ 7.42 (dd, 2H, J=1.5, 4.7 Hz, H$_{arom}$), 7.33-7.30 (m, 6H, H$_{arom}$), 6.53 (s, 2H, H9), 5.30 (d, 2H, J=3.8 Hz, NH), 4.35-4.29 (m, 2H, H11a), 4.12-4.06 (m, 4H, OCH$_2$CH$_2$CH$_2$O), 3.95 (d, 2H, J=10.3 Hz, H11), 3.72 (s, 6H, OCH$_3$×2), 3.53-3.19 (m, 4H, H1), 2.23-2.21 (m, 2H, OCH$_2$CH$_2$CH$_2$O).

Example 4

(a) 1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-(quinolin-6-yl)-1,10,11,11a-tetrahydro-5H-pyrrolo[2,1-c][1,4]benzodiazepin-5-one]] (23)

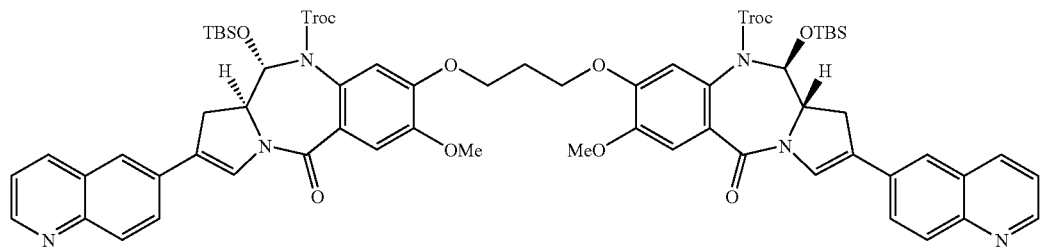

23

A solution of TEA (0.12 mL, 0.84 mmol, 6.0 eq) in H$_2$O (0.8 mL) and EtOH (5 mL) was added to a solution of triflate 13 (202 mg, 0.14 mmol) in toluene (5 mL) at room temperature. To this mixture 6-(4,4,5,5-tetramethyl-1,3,2-dioxaborolan-2-yl) quinoline (93.0 mg, 0.36 mmol, 2.6 eq) and Pd(PPh$_3$)$_4$ (6.5 mg, 6 μmol, 0.04 eq) were added. The reaction mixture was heated at 100° C. under microwave irradiation for 15 minutes when TLC (80:20 v/v EtOAc/hexane) revealed complete consumption of the starting material. Excess solvent was removed and the residue was dissolved in EtOAc (20 mL), washed with H$_2$O (15 mL), brine (15 mL) and dried (MgSO$_4$). Filtration and evaporation of solvent afforded the crude product which was purified by flash column chromatography (80:20 v/v hexane/EtOAc then gradient to 50:50 v/v hexane/EtOAc) to afford 23 as a yellow glass (126 mg, 64%): $^1$H NMR (400 MHz, CDCl$_3$) δ 8.88 (dd, 2H, J=1.6, 4.2 Hz, H$_{arom}$), 8.14 (d, 2H, J=7.6 Hz, H$_{arom}$), 8.07 (d, 2H, J=9.0 Hz, H$_{arom}$), 7.85 (dd, 2H, J=1.8, 8.9 Hz, H$_{arom}$), 7.66 (s, 2H, H3), 7.55 (d, 2H, J=1.8 Hz, H$_{arom}$), 7.41 (dd, 2H, J=4.3, 8.3 Hz, H$_{arom}$), 7.31 (s, 2H, H6), 6.82 (s, 2H, H9), 5.98 (d, 2H, J=8.8 Hz, H11), 5.25 (d, 2H, J=12.1 Hz, Troc CH$_2$), 4.34-4.31 (m, 2H, OCH$_2$CH$_2$CH$_2$O), 4.21-4.15 (m, 4H, Troc CH$_2$ and OCH$_2$CH$_2$CH$_2$O), 4.09-4.03 (m, 2H, H11a), 3.97 (s, 6H, OCH$_3$×2), 3.48 (ddd, 2H, J=1.6, 10.4, 16.1 Hz, H1), 2.98 (dd, 2H, J=2.4, 16.1 Hz, H1), 2.50-2.47 (m, 2H, OCH$_2$CH$_2$CH$_2$O), 0.95 (s, 18H, TBS CH$_3$×6), 0.32 and 0.28 (s×2, 12H, TBS CH$_3$×4).

(b) 1,1'-[[(Propane-1,3-diyl)dioxy]bis[(11aS)-7-methoxy-2-(quinolin-6-yl)-1,11a-dihydro-5H-pyrrolo[2,1-c][1,4]benzodiazepine-5-one]] (24)

10% Cd/Pb couple (516 mg, 4.21 mmol, 25 eq) was added to a rapidly stirring mixture of 23 (234 mg, 0.17 mmol), THF (5 mL) and 1 N NH$_4$OAc (5 mL). The reaction mixture was allowed to stir for 5 hours when TLC showed complete consumption of the starting material and formation of a small amount of side products. The solids were filtered and rinsed with H$_2$O and a large amount of MeOH. Excess solvent was removed and the residue was diluted with H$_2$O (35 mL) and CHCl$_3$ (35 mL). The aqueous layer was extracted with CHCl$_3$ (3×30 mL) and the organic extracts were combined, washed with brine (100 mL) and dried (MgSO$_4$). Filtration and evaporation of solvent afforded the crude product which was purified by flash column chromatography (99.5:0.5 v/v CHCl$_3$/MeOH then gradient to 96:4 v/v CHCl$_3$/MeOH) to afford 24 as a yellow glass (44 mg, 33%): $^1$H NMR (400 MHz, CDCl$_3$) 8.85 (dd, 2H, J=1.6, 4.2 Hz, H$_{arom}$), 8.09 (d, 2H, J=7.6 Hz, H$_{arom}$), 8.03 (d, 2H, J=9.0 Hz, H$_{arom}$), 7.88 (d, 2H, J=3.9 Hz, H11), 7.82 (dd, 2H, J=1.8, 8.9 Hz, H$_{arom}$), 7.24 (s, 2H, H3), 7.59 (s, 2H, H$_{arom}$), 7.52 (s, 2H, H6), 7.48 (dd, 2H, J=4.3, 8.3 Hz, H$_{arom}$), 6.88 (s, 2H, H9), 4.48-4.42 (m, 2H, H11a), 4.39-4.28 (m, 4H, OCH$_2$CH$_2$CH$_2$O), 3.94 (s, 6H, OCH$_3$×2), 3.76-3.63 (m, 2H, H1), 3.09-2.98 (m, 2H, H1), 2.46-2.43 (m, 2H, OCH$_2$CH$_2$CH$_2$O).

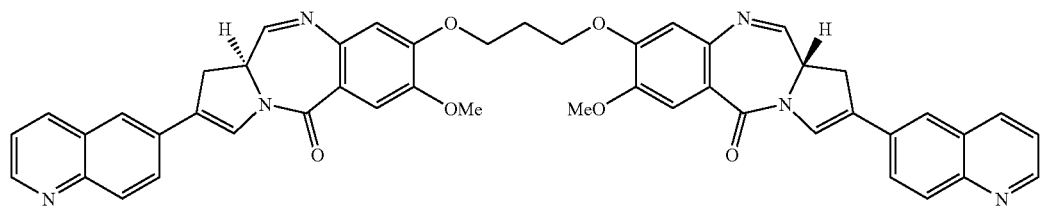

24

Example 5

(a) 1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-(3-methoxybenzene)-1,10,11,11a-tetrahydro-5H-pyrrolo[2,1-c][1,4]benzodiazepin-5-one]] (25)

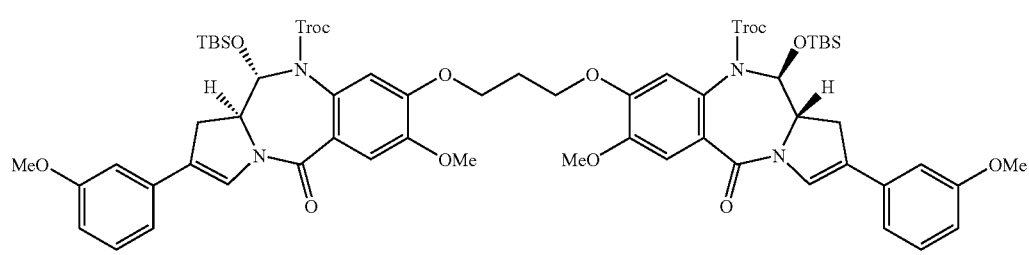

A solution of TEA (0.071 mL, 0.51 mmol, 6.0 eq) in H$_2$O (0.6 mL) and EtOH (3.5 mL) was added to a solution of triflate 13 (122 mg, 0.085 mmol) in toluene (3.5 mL) at room temperature. To this mixture 3-methoxyphenolboronic acid (33.5 mg, 0.22 mmol, 2.6 eq) and Pd(PPh$_3$)$_4$ (3.9 mg, 3.4 μmol, 0.04 eq) were added. The reaction mixture was heated at 100° C. under microwave irradiation for 5 minutes when TLC (80:20 v/v EtOAc/hexane) revealed complete consumption of the starting material. Excess solvent was removed and the residue was dissolved in EtOAc (10 mL), washed with H$_2$O (10 mL), brine (10 mL) and dried (MgSO$_4$). Filtration and evaporation of solvent afforded the crude product which was purified by flash column chromatography (80:20 v/v hexane/EtOAc then gradient to 60:40 v/v hexane/EtOAc) to afford 25 as a yellow glass (66 mg, 57%): $^1$H NMR (400 MHz, CDCl$_3$) 7.23 (s, 2H, H3), 7.05-7.00 (m, 4H, H6 and H$_{arom}$), 6.70 (d, 2H, J=8.7 Hz, H$_{arom}$), 6.64 (s, 2H, H$_{arom}$), 6.67-6.64 (m, 4H, H$_{arom}$ and H9), 5.67 (d, 2H, J=8.8 Hz, H11), 4.98 (d, 2H, J=12.0 Hz, Troc CH$_2$), 4.08-4.02 (m, 2H, OCH$_2$CH$_2$CH$_2$O), 3.92-3.84 (m, 4H, Troc CH$_2$ and OCH$_2$CH$_2$CH$_2$O), 3.74-3.66 (m, 8H, H11a and OCH$_3$×2), 3.68 (s, 6H, OCH$_3$×2), 3.10 (dd, 2H, J=10.8, 16.6 Hz, H1), 2.60 (d, 2H, J=16.5 Hz, H1), 2.22-2.19 (m, 2H, OCH$_2$CH$_2$CH$_2$O), 0.68 (s, 18H, TBS CH$_3$×6), 0.02 and 0.00 (s×2, 12H, TBS CH$_3$×4).

(b) 1,1'-[[(Propane-1,3-diyl)dioxy]bis[(11aS)-7-methoxy-2-(3-methoxybenzene)-1,11a-dihydro-5H-pyrrolo[2,1-c][1,4]benzodiazepine-5-one]] (26)

10% Cd/Pb couple (269 mg, 2.20 mmol, 25 eq) was added to a rapidly stirring mixture of 25 (119 mg, 0.088 mmol), THF (3 mL) and 1 N NH$_4$OAc (3 mL). The reaction mixture was allowed to stir for 3.5 hours when TLC showed complete consumption of the starting material. The solids were filtered and rinsed with H$_2$O and MeOH. Excess solvent was removed and the residue was diluted with H$_2$O (20 mL) and DCM (20 mL). The aqueous layer was extracted with DCM (3×20 mL) and the organic extracts were combined, washed with H$_2$O (50 mL) and brine (50 mL) and dried (MgSO$_4$). Filtration and evaporation of solvent afforded the crude product which was purified by flash column chromatography (99.9:0.1 v/v CHCl$_3$/MeOH then gradient to 98:2 v/v CHCl$_3$/MeOH) to afford 26 as a yellow glass (35 mg, 54%): NMR (400 MHz, CDCl$_3$) δ 7.79 (d, 2H, J=3.9 Hz, H11), 7.44 (s, 2H, H3), 7.42 (s, 2H, H6), 7.21-7.16 (m, 2H, H$_{arom}$), 6.90 (d, 2H, J=8.7 Hz, H$_{arom}$), 6.84-6.83 (m, 2H, H$_{arom}$), 6.80 (s, 2H, H9), 4.33-4.17 (m, 6H, OCH$_2$CH$_2$CH$_2$O and H11a), 3.86 (s, 6H, OCH$_3$×2), 3.75 (s, 6H, OCH$_3$×2), 3.44 (dd, 2H, J=11.8, 16.2 Hz, H1), 3.30 (d, 2H, J=16.2 Hz, H1), 2.39-2.33 (m, 2H, OCH$_2$CH$_2$CH$_2$O).

(c) 1,1'-[[(Propane-1,3-diyl)dioxy]bis[(11aS)-11-sulpho-7-methoxy-2-(3-methoxybenzene)-1, 10,11, 11a-tetrahydro-5H-pyrrolo[2,1-c][1,4]benzodiazepin-5-one]] sodium salt (27)

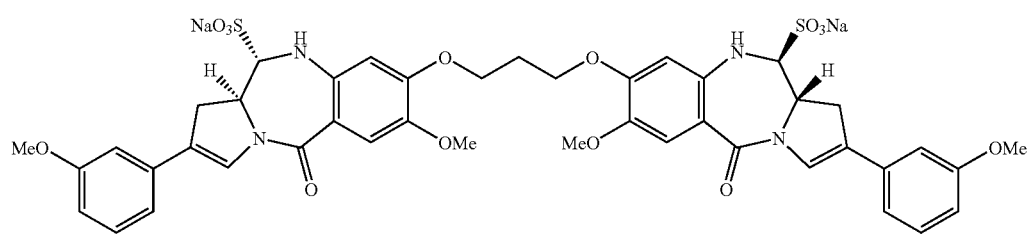

A solution of sodium bisulphite (7.6 mg, 0.073 mmol, 2.0 equiv.) in H$_2$O (1.7 mL) was added to a solution of compound 26 (27.0 mg, 0.036 mmol) in DCM (1.7 mL). The reaction mixture was allowed to stir for 2 hours. TLC (EtOAc) revealed complete consumption of the starting material and a product spot at the base line. The reaction mixture was diluted with DCM (5 mL) and H$_2$O (5 mL). The aqueous layer was separated and lyophilized to afford 27 as a lightweight white solid (12.1 mg, 35%): $^1$H NMR (400 MHz, DMSO) δ 7.61 (s, 2H, H3), 7.27-7.23 (m, 2H, H$_{arom}$), 7.08-6.99 (m, 6H, H$_{arom}$ and H6), 6.81-6.78 (m, 2H, H$_{arom}$), 6.54 (s, 2H, H9), 5.30 (s, 2H, NH), 4.37-4.30 (m, 2H, H11a), 4.17-4.08 (m, 4H, OCH$_2$CH$_2$CH$_2$O), 3.84 (d, 2H, J=10.4 Hz, H11), 3.78 (s, 6H, OCH$_3$×2), 3.62 (s, 6H, OCH$_3$×2), 3.52-3.20 (m, 4H, H1), 2.26-2.20 (m, 2H, OCH$_2$CH$_2$CH$_2$O).

Example 6

(a) 1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-(3,4-methylenedioxyphenyl)-1,10,11,11a-tetrahydro-5H-pyrrolo[2,1-c][1,4]benzodiazepin-5-one]] (28)

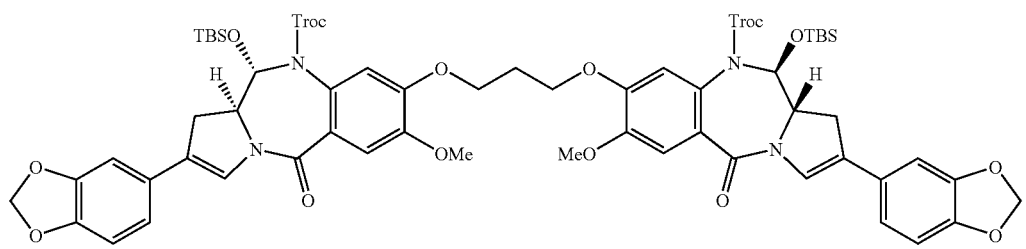

A solution of TEA (0.066 mL, 0.47 mmol, 6.0 eq) in H$_2$O (0.6 mL) and EtOH (3.5 mL) was added to a solution of triflate 13 (122 mg, 0.085 mmol) in toluene (3.5 mL) at room temperature. To this mixture 3,4-methylenedioxyphenylboronic acid (34.2 mg, 0.21 mmol, 2.6 eq) and Pd(PPh$_3$)$_4$ (3.6 mg, 3.2 μmol, 0.04 eq) were added. The reaction mixture was heated at 100° C. under microwave irradiation for 5 minutes when TLC (80:20 v/v EtOAc/hexane) revealed complete consumption of the starting material. Excess solvent was removed and the residue was dissolved in EtOAc (10 mL), washed with H$_2$O (10 mL), brine (10 mL) and dried (MgSO$_4$). Filtration and evaporation of solvent afforded the crude product which was purified by flash column chromatography (80:20 v/v hexane/EtOAc then gradient to 65:35 v/v hexane/EtOAc) to afford 28 as a yellow glass (84 mg, 77%): $^1$H NMR (400 MHz, CDCl$_3$) δ 7.34 (s, 2H, H6), 7.26 (s, 2H, H3), 6.89 (s, 2H, H9), 6.78-6.76 (m, 4H, H$_{arom}$), 5.98 (s, 2H, OCH$_2$O), 5.89 (d, 2H, J=8.8 Hz, H11), 5.23 (d, 2H, J=12.0 Hz, Troc CH$_2$), 4.32-4.27 (m, 2H, OCH$_2$CH$_2$CH$_2$O), 4.18-4.09 (m, 4H, Troc CH$_2$ and OCH$_2$CH$_2$CH$_2$O), 3.97-3.91 (m, 8H, H11a and OCH$_3$×2), 3.30 (dd, 2H, J=10.8, 16.6 Hz, H1), 2.76 (d, 2H, J=16.6 Hz, H1), 2.46-2.44 (m, 2H, OCH$_2$CH$_2$CH$_2$O), 0.88 (s, 18H, TBS CH$_3$×6), 0.28 and 0.25 (s×2, 12H, TBS CH$_3$×4).

(b) 1,1'-[[(Propane-1,3-diyl)dioxy]bis[(11aS)-7-methoxy-2-(3,4-methylenedioxyphenyl)-1,11a-dihydro-5H-pyrrolo[2,1-c][1,4]benzodiazepine-5-one]] (29)

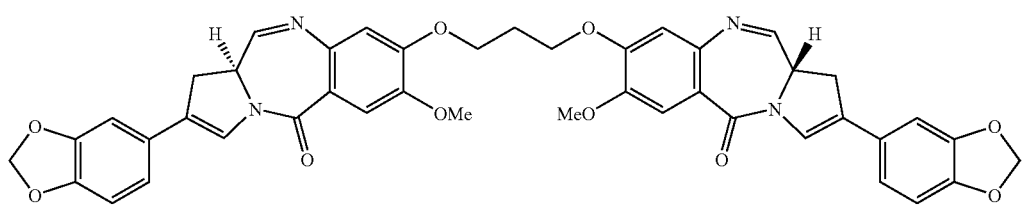

29

10% Cd/Pb couple (307 mg, 2.51 mmol, 25 eq) was added to a rapidly stirring mixture of 28 (139 mg, 0.101 mmol), THF (3.5 mL) and 1 N NH$_4$OAc (3.5 mL). The reaction mixture was allowed to stir for 5 hours when TLC showed complete consumption of the starting material and formation of a small amount of side products. The solids were filtered and rinsed with H$_2$O and MeOH. Excess solvent was removed and the residue was diluted with H$_2$O (25 mL) and DCM (25 mL). The aqueous layer was extracted with DCM (3×40 mL) and the organic extracts were combined, washed with H$_2$O (80 mL) and brine (80 mL) and dried (MgSO$_4$). Filtration and evaporation of solvent afforded the crude product which was purified by flash column chromatography (99.9:0.1 v/v CHCl$_3$/MeOH then gradient to 98:2 v/v CHCl$_3$/MeOH) to afford 26 as a yellow glass (30 mg, 39%): $^1$H NMR (400 MHz, CDCl$_3$) 7.86 (d, 2H, J=3.9 Hz, H11), 7.60 (s, 2H, H6), 7.36 (s, 2H, H3), 6.91 (d, 2H, J=0.9 Hz, H$_{arom}$), 6.86 (s, 2H), 6.82-6.78 (m, 4H, H9 and H$_{arom}$), 5.97 (s, 2H, OCH$_2$O), 4.36-4.25 (m, 6H, H11a and OCH$_2$CH$_2$CH$_2$O), 3.93 (s, 6H, OCH$_3$×2), 3.52 (dd, 2H, J=10.8, 16.6 Hz, H1), 3.33 (d, 2H, J=16.6 Hz, H1), 2.46-2.40 (m, 2H, OCH$_2$CH$_2$CH$_2$O).

(c) 1,1'-[[(Propane-1,3-diyl)dioxy]bis[(11aS)-11-sulpho-7-methoxy-2-(3,4-methylenedioxyphenyl)-1,10,11,11a-tetrahydro-5H-pyrrolo[2,1-c][1,4]benzodiazepin-5-one]] sodium salt (30)

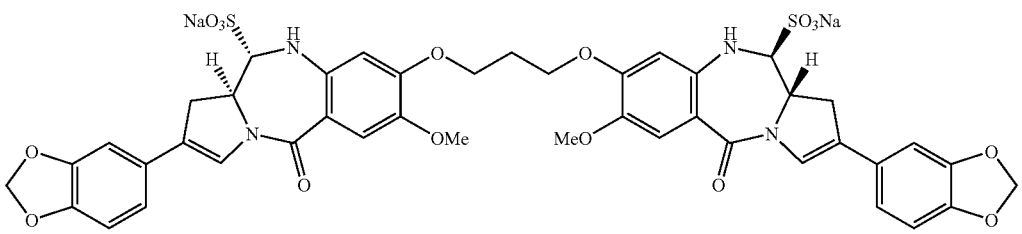

30

A solution of sodium bisulphite (2.2 mg, 0.021 mmol, 2.0 equiv.) in H$_2$O (0.5 mL) was added to a solution of compound 29 (8.1 mg, 0.0105 mmol) in DCM (0.5 mL). The reaction mixture was allowed to stir for 5 hours. TLC (EtOAc) revealed complete consumption of the starting material and a product spot at the base line. The reaction mixture was diluted with DCM (1.5 mL) and H$_2$O (1.5 mL). The aqueous layer was separated and lyophilized to afford 30 as a lightweight white solid (3.5 mg, 34%): $^1$H NMR (400 MHz, DMSO) δ 7.47 (s, 2H, H3), 6.98 (s×2, 2H, H6), 7.06-6.78 (m, 6H, H$_{arom}$), 6.51 (s×2, 2H, H9), 5.27 (s, 2H, NH), 4.32-4.26 (m, 2H, H11a), 4.17-4.07 (m, 4H, OCH$_2$CH$_2$CH$_2$O), 3.93 (d, 2H, J=10.4 Hz, H11), 3.72 (s, 6H, OCH$_3$×2), 3.50-3.20 (m, 4H, H1), 2.27-2.20 (m, 2H, OCH$_2$CH$_2$CH$_2$O).

Example 7

(a) 1,1'-[[(Propane-1,3-diyl)dioxy]bis[(11S,11aS)-10-(2,2,2-trichloroethoxycarbonyl)-11-(tert-butyldimethylsilyloxy)-7-methoxy-2-(4-fluorobenzene)-1,10,11,11a-tetrahydro-5H-pyrrolo[2,1-c][1,4]benzodiazepin-5-one]] (31)

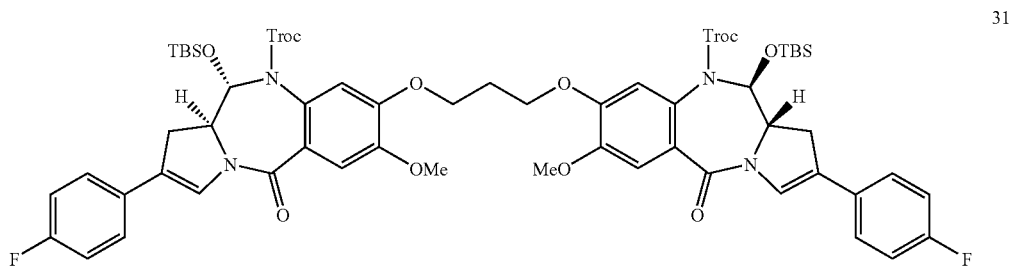

A solution of TEA (0.072 mL, 0.52 mmol, 6.0 eq) in $H_2O$ (0.6 mL) and EtOH (3.5 mL) was added to a solution of triflate 13 (125 mg, 0.086 mmol) in toluene (3.5 mL) at room temperature. To this mixture 4-fluorobenzeneboronic acid (31.6 0.22 mmol, 2.6 eq) and $Pd(PPh_3)_4$ (4.0, 3.4 µmol, 0.04 eq) were added. The reaction mixture was heated at 100° C. under microwave irradiation for 5 minutes when TLC (80:20 v/v EtOAc/hexane) revealed complete consumption of the starting material. Excess solvent was removed and the residue was dissolved in EtOAc (10 mL), washed with $H_2O$ (10 mL), brine (10 mL) and dried ($MgSO_4$). Filtration and evaporation of solvent afforded the crude product which was purified by flash column chromatography (80:20 v/v hexane/EtOAc then gradient to 65:35 v/v hexane/EtOAc) to afford 31 as a yellow glass (82 mg, 71%): $^1H$ NMR (400 MHz, $CDCl_3$) δ 7.40 (s, 2H, H3), 7.42 (dd, 4H, J=5.2, 8.7 Hz, $H_{arom}$), 7.28 (s, 2H, H6), 7.06 (dd, 4H, J=8.7 Hz, $H_{arom}$), 6.70 (s, 2H, H9), 5.92 (d, 2H, J=8.8 Hz, H11), 5.22 (d, 2H, J=12.0 Hz, Troc $CH_2$), 4.32-4.29 (m, 2H, $OCH_2CH_2CH_2O$), 4.19-4.10 (m, 4H, Troc $CH_2$ and $OCH_2CH_2CH_2O$), 4.00-3.92 (m, 8H, H11a and $OCH_3$×2), 3.33 (dd, 2H, J=10.8, 16.5 Hz, H1), 2.84 (d, 2H, J=16.5 Hz, H1), 2.49-2.44 (m, 2H, $OCH_2CH_2CH_2O$), 0.92 (s, 18H, TBS $CH_3$×6), 0.30 and 0.27 (s×2, 12H, TBS $CH_3$×4).

(b) 1,1'-[[(Propane-1,3-diyl)dioxy]bis[(11aS)-7-methoxy-2-(4-fluorobenzene)-1,11a-dihydro-5H-pyrrolo[2,1-c][1,4]benzodiazepine-5-one]] (32)

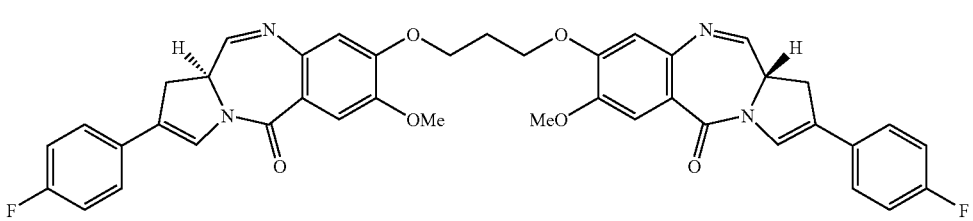

10% Cd/Pb couple (342 mg, 2.80 mmol, 25 eq) was added to a rapidly stirring mixture of 31 (149 mg, 0.112 mmol), THF (4.5 mL) and 1N $NH_4OAc$ (4.5 mL). The reaction mixture was allowed to stir for 5 hours when TLC showed complete consumption of the starting material. The solids were filtered and rinsed with $H_2O$ and MeOH. Excess solvent was removed and the residue was diluted with $H_2O$ (30 mL) and DCM (30 mL). The aqueous layer was extracted with DCM (3×30 mL) and the organic extracts were combined, washed with $H_2O$ (80 mL) and brine (80 mL) and dried ($MgSO_4$). Filtration and evaporation of solvent afforded the crude product which was purified by flash column chromatography (99.9:0.1 v/v $CHCl_3$/MeOH then gradient to 98:2 v/v $CHCl_3$/MeOH) to afford 32 as a yellow glass (60 mg, 75%): $^1H$ NMR (400 MHz, $CDCl_3$) 7.88 (d, 2H, J=3.9 Hz, H11), δ 7.51 (s, 2H, H6), 7.43 (s, 2H, H3), 7.34 (dd, 4H, J=5.3, 8.6 Hz, $H_{arom}$), 7.06 (dd, 4H, J=8.7 Hz, $H_{arom}$), 6.87 (s, 2H, H9), 4.41-4.25 (m, 6H, H11a and $OCH_2CH_2CH_2O$), 3.93 (s, 3H, $OCH_3$×2), 3.55 (dd, 2H, J=10.8, 16.5 Hz, H1), 3.37 (d, 2H, J=16.5 Hz, H1), 2.46-2.42 (m, 2H, $OCH_2CH_2CH_2O$).

(c) 1,1'-[[(Propane-1,3-diyl)dioxy]bis[(11aS)-11-sulpho-7-methoxy-2-(4-fluorobenzene)-1,10,11,11a-tetrahydro-5H-pyrrolo[2,1-c][1,4]benzodiazepin-5-one]] sodium salt (33)

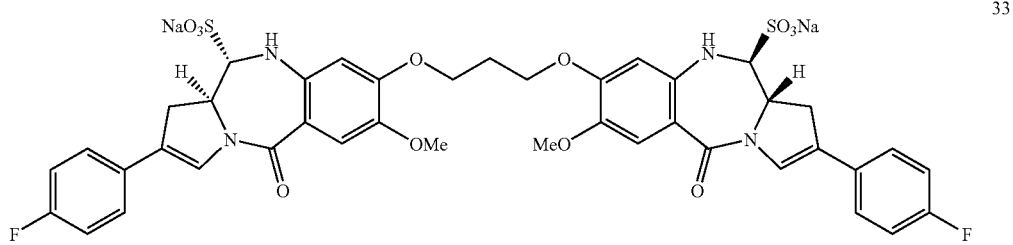

A solution of sodium bisulphite (13.9 mg, 0.134 mmol, 2.0 equiv.) in H₂O (3 mL) was added to a solution of compound 32 (48.0 mg, 0.067 mmol) in DCM (3 mL). The reaction mixture was allowed to stir for 2 hours. TLC (EtOAc) revealed complete consumption of the starting material and a product spot at the base line. The reaction mixture was diluted with DCM (8 mL) and H₂O (8 mL). The aqueous layer was separated and lyophilized to afford 33 as a lightweight white solid (35.5 mg, 58%): $^1$H NMR (400 MHz, DMSO) δ 7.56 (s, 2H, H3), 7.49 (dd, 4H, J=5.3, 8.6 Hz, $H_{arom}$), 7.17 (dd, 4H, J=8.7 Hz, $H_{arom}$), 7.07 (s, 2H, H6), 6.53 (s, 2H, H9), 5.28 (s, 2H, NH), 4.36-4.30 (m, 2H, H11a), 4.17-4.09 (m, 4H, OCH₂CH₂CH₂O), 3.95 (d, 2H, J=10.4 Hz, H11), 3.73 (s, 6H, OCH₃×2), 3.53-3.22 (m, 4H, H1), 2.27-2.19 (m, 2H, OCH₂CH₂CH₂O).

Example 8

(a) 1,1'-[[(Pentane-1,5-diyl)dioxy]bis[(2S,4R)-(5-methoxy-2-nitro-1,4-phenylene)carbonyl]]bis[2-(tert-butyldimethylsilyloxymethyl)-4-hydroxy-acetylpyrrolidine] (36)

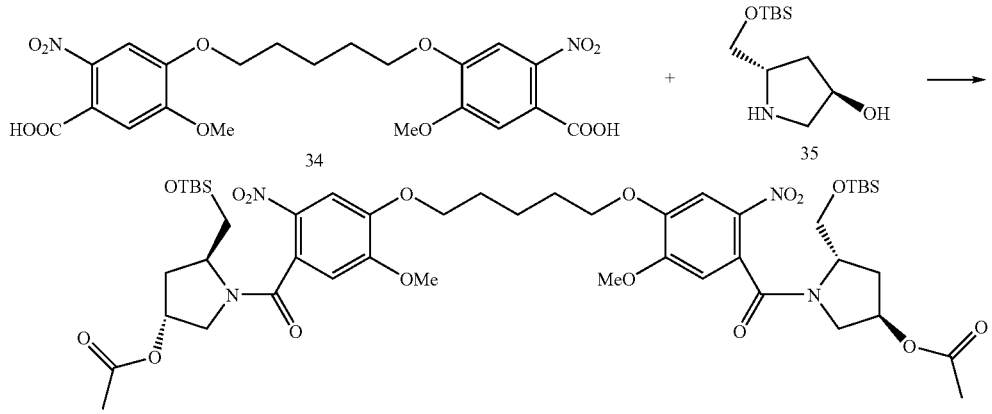

A catalytic amount of DMF (2 drops) was added to a stirred solution of the nitro-acid 34 (15.0 g, 30.4 mmol) and oxalyl chloride (13.5 mL, 19.3 g, 152 mmol) in dry THF (300 mL). The reaction mixture was allowed to stir for 16 hours at room temperature and the solvent was removed by evaporation in vacuo. The resulting residue was re-dissolved in dry THF (225 mL) and the acid chloride solution was added dropwise to a stirred mixture of the amine 35 (20.7 g, 76.0 mmol) and TEA (84 mL, 61.52 g, 608 mmol) in THF (150 mL) at 0° C. (ice/acetone) under a nitrogen atmosphere. The reaction mixture was allowed to warm to room temperature and stirred for a further 16 hours. Excess THF was removed by rotary evaporation and the resulting residue was partitioned between H₂O (400 mL) and EtOAc (400 mL). The layers were allowed to separate and the aqueous layer was extracted with EtOAc (3×130 mL). The combined organic layers were then washed with saturated NH₄Cl (200 mL), saturated NaHCO₃ (200 mL), brine (200 mL) and dried (MgSO₄). Filtration and evaporation of the solvent gave the crude product as a dark coloured oil. Purification by flash chromatography (gradient elution: 60:40 v/v Hexane/EtOAc to 40:60 v/v Hexane/EtOAc) isolated the pure amide 36 as a light yellow coloured glass (23.56 g, 77%): $^1$H NMR (400 MHz, CDCl₃) (rotamers) δ 7.66 (s, 2H), 6.71 (s, 2H), 5.21-5.17 (m, 2H), 4.57-4.53 (m, 2H), 4.21-4.08 (m, 6H), 3.91 (s, 6H), 3.76-3.72 (m, 2H), 3.46 (dd, 2H, J=11.8, 4.6 Hz), 3.21 (d, 2H, J=11.9 Hz), 2.44-2.37 (m, 2H), 2.24-2.18 (m, 2H), 2.03-1.94 (m, 10H), 1.75-1.67 (m, 2H), 0.91-0.84 (m, 18H), 0.11-0.05 (m, 12H); $^{13}$C NMR (100 MHz, CDCl₃) δ 171.0, 166.4, 154.4, 148.5, 137.5, 127.7, 109.2, 108.3, 72.9, 69.3, 62.6, 57.4, 56.5, 54.8, 33.0, 28.5, 25.8, 22.5, 21.0, 18.2, −5.4 and −5.5; LC/MS 2.93 min (ES+) m/z (relative intensity) 1006 ([M+H]⁺, 100).

(b) 1,1'-[[(Pentane-1,5-diyl)dioxy]bis[(2S,4R)-(5-methoxy-2-amino-1,4-phenylene)carbonyl]]bis[2-(tert-butyldimethylsilyloxymethyl)-4-hydroxy-acetylpyrrolidine] (37)

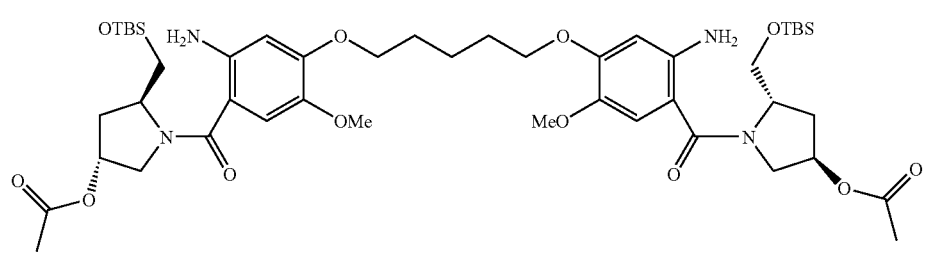

37

A slurry of 10% Pd—C (550 mg) in EtOAc (20 mL) was added to a solution of the nitro compound 36 (5.5 g, 5.47 mmol) in EtOAc (73 mL). The mixture was subjected to hydrogenation using Parr apparatus at 30 psi for a total of 24 hours. The mixture was degassed and analysed by TLC (EtOAc) where complete consumption of starting material was observed. The catalyst was removed by vacuum filtration through Whatman GF/F filter paper and the filtrate evaporated to provide the aniline 37 as a grey coloured foam (5.17 g, 100%): $^1$H NMR (400 MHz, CDCl$_3$) δ 6.71 (s, 2H), 6.22 (s, 2H), 5.25-5.23 (m, 2H), 4.58-4.30 (m, 6H), 4.14-4.05 (m, 2H), 3.99 (t, J=6.6 Hz, 4H), 3.79-3.73 (m, 8H), 3.69-3.54 (m, 4H), 2.40-2.33 (m, 2H), 2.16-2.08 (m, 2H), 2.00 (s, 6H), 1.94-1.87 (m, 4H), 1.68-1.60 (m, 2H), 0.89 (s, 18H), 0.05 and 0.04 (s×2, 12H); $^{13}$C NMR (100 MHz, CDCl$_3$) δ 170.6, 170.0, 151.5, 141.7, 141.2, 113.1, 111.0, 102.0, 73.5, 68.5, 62.6, 57.0, 56.2, 32.9, 28.7, 25.6, 22.6, 21.1, 18.1, −5.1 and −5.4; LC/MS 2.78 min (ES+) m/z (relative intensity) 946 ([M+H]$^+$, 52), 672 (30), 399 (20), 274 (65), 166 (20).

(c) 1,1'-[[(Pentane-1,5-diyl)dioxy]bis[(2S,4R)-[5-methoxy-1,4-phenylene-2-(2,2,2-trichloroethoxycarbonylamino)]carbonyl]]bis[2-(tert-butyldimethylsilyloxymethyl)-4-hydroxyacetylpyrrolidine] (38)

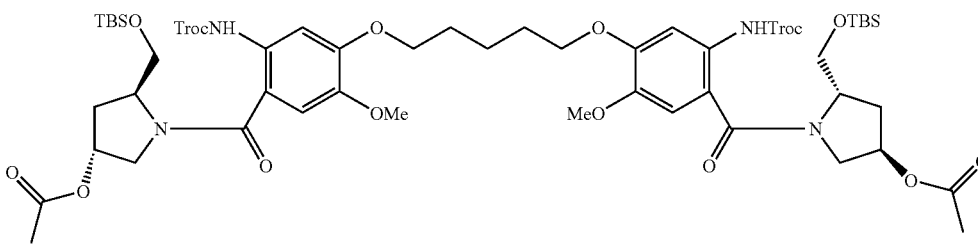

38

A solution of 2,2,2-trichloroethyl chloroformate (2.63 mL, 4.05 g, 19.1 mmol) in dry DCM (45 mL) was added dropwise to a stirred solution of amine 37 (8.21 g, 8.70 mmol) and anhydrous pyridine (2.81 mL, 2.75 g, 34.8 mmol) in dry DCM (120 mL) at −10° C. (liquid N$_2$/ethanediol). After 16 hours stirring at room temperature TLC (50:50 v/v Hexane/EtOAc) revealed complete consumption of starting material. The reaction mixture was washed with saturated NH$_4$Cl (2×70 mL), saturated CuSO$_4$ (70 mL), H$_2$O (70 mL), brine (70 mL) and dried (MgSO$_4$). Filtration and evaporation of the solvent yielded the Troc-carbamate 38 as a yellow foam (11.25 g, 99%): $^1$H NMR (400 MHz, CDCl$_3$) δ 9.48 (br s, 1H), 7.85 (s, 2H), 6.79 (s, 2H), 5.28-5.24 (m, 2H), 4.86-4.76 (m, 4H), 4.70-4.53 (m, 2H), 4.12 (t, J=6.4 Hz, 4H), 4.14-4.10 (m, 2H), 3.80 (s, 6H), 3.76 (dd, 2H, J=12.2, 3.8 Hz), 3.69-3.62 (m, 4H), 2.44-2.37 (m, 2H), 2.16 (dd, 2H, J=14.1, 8.1 Hz), 2.10-1.92 (m, 10H), 1.72-1.65 (m, 2H), 0.90 (s, 18H), 0.06 and 0.04 (s×2, 12H); $^{13}$C NMR (100 MHz, CDCl$_3$) δ 170.5, 169.3, 152.0, 151.1, 144.2, 132.4, 114.4, 111.8, 105.2, 95.3, 74.4, 73.4, 68.7, 62.3, 57.3, 57.2, 56.5, 32.6, 28.7, 25.8, 22.6, 21.1, 18.1, −5.4 and −5.5; LC/MS 3.23 min (ES+/ES−) m/z (M$^+$ not observed), 472 (30), 416 (15), 302 (85), 274 (60), 198 (20), 170 (100), 142 (50), 110 (80).

(d) 1,1'-[[(Pentane-1,5-diyl)dioxy]bis[(2S,4R)-[5-methoxy-1,4-phenylene-2-(2,2,2-trichloroethoxycarbonylamino)]carbonyl]]bis(2-hydroxymethyl-4-hydroxyacetylpyrrolidine) (39)

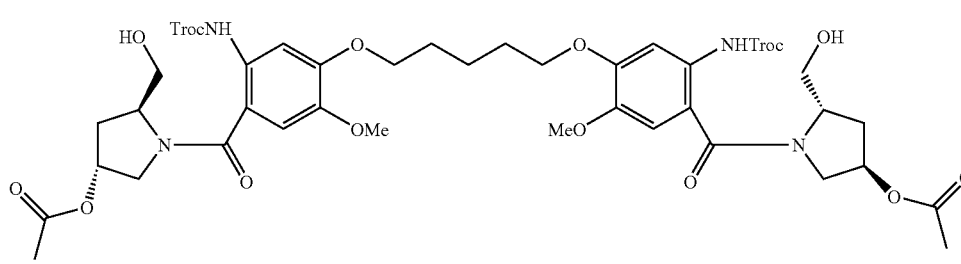

Glacial acetic acid (90 mL) was added to a stirred solution of 38 (5.06 g, 3.91 mmol) in H₂O (30 mL) and THF (30 mL). The reaction mixture was allowed to stir at room temperature for 16 h at which point TLC (95:5 v/v CHCl₃/MeOH) revealed completion of the reaction. The acidic solution was added dropwise to a stirred solution of NaHCO₃ (132 g) in H₂O (1.3 L) at 0° C. (ice/acetone). The aqueous layer was extracted with EtOAc (3×200 mL) and the organic layers were combined, washed with H₂O (200 mL), brine (200 mL) and dried (MgSO₄). Filtration and evaporation of the solvent in vacuo afforded the crude product which was purified by flash column chromatography (98:2 v/v CHCl₃/MeOH) to provide the bis-alcohol 39 as a white glass (4.04 g, 97%): $^1$H NMR (400 MHz, CDCl₃) δ 9.01 (br s, 2H), 7.66 (s, 2H), 6.79 (s, 2H), 5.23-5.20 (m, 2H), 4.84 (d, 2H, J=12.0 Hz), 4.77 (d, 2H, J=12.0 Hz), 4.63-4.55 (m, 2H), 4.10 (t, J=6.4 Hz, 4H), 4.08-4.01 (m, 2H), 3.82 (s, 6H), 3.75 (dd, 2H, J=12.6, 3.7 Hz), 3.70-3.58 (m, 4H), 2.26 (dd, 2H, J=14.1, 7.6 Hz), 2.15-2.06 (m, 2H), 2.01 (s, 6H), 1.98-1.92 (m, 4H), 1.74-1.65 (m, 2H); $^{13}$C NMR (100 MHz, CDCl₃) 170.6, 170.4, 152.1, 150.9, 144.8, 131.0, 115.6, 111.3, 105.7, 95.3, 74.3, 72.5, 68.7, 64.3, 58.8, 56.6, 56.5, 33.6, 28.5, 22.6, 21.1.

(e) 1,1'-[[(Pentane-1,5-diyl)dioxy]bis[(11S,11aS,2R)-10-(2,2,2-trichloroethoxycarbonyl)-11-hydroxy-7-methoxy-2-hydroxyacetyl-1,2,3,10,11,11a-hexahydro-5H-pyrrolo[2,1-c][1,4]benzodiazepin-5-one]] (40)

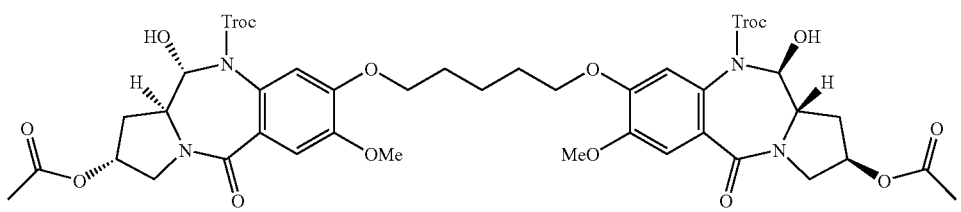

TEMPO (234 mg, 1.50 mmol) and BAIB (5.31 g, 16.5 mmol) were added to a stirred solution of bis-alcohol 39 (4.0 g, 3.75 mmol) in DCM (140 mL). The reaction mixture was allowed to stir under a nitrogen atmosphere for 24 hours at which point TLC (95:5 v/v CHCl₃/MeOH) revealed conversion of starting material to product. The mixture was diluted with DCM (30 mL), washed with saturated aqueous NaHSO₃ (2×30 mL), saturated aqueous NaHCO₃ (2×30 mL), brine (30 mL) and dried (MgSO₄). Filtration and evaporation of the solvent afforded the crude product which was purified by flash column chromatography (gradient elution: CHCl₃ to 99.5:0.5 v/v CHCl₃/MeOH) to provide the cyclised product 40 as a light coloured yellow glass (1.99 g, 50%): $^1$H NMR (400 MHz, CDCl₃) δ 7.27 (s, 2H), 6.78 (s, 2H), 5.68 (d, 2H, J=9.7 Hz), 5.41-5.35 (m, 2H), 5.24 (d, 2H, J=12.0 Hz), 4.23 (d, 2H, J=12.0 Hz), 4.14-3.97 (m, 6H), 3.93 (s, 6H), 3.77-3.69 (m, 4H), 2.46-2.33 (m, 4H), 2.05 (s, 6H), 2.03-1.87 (m, 4H), 1.70-1.62 (m, 2H); $^{13}$C NMR (100 MHz, CDCl₃) δ 170.4, 167.5, 154.4, 150.6, 149.0, 127.3, 124.5, 113.7, 110.8, 95.0, 87.5, 75.0, 71.4, 68.8, 58.3, 56.2, 51.1, 35.8, 28.5, 22.4, 21.0.

(f) 1,1'-[[(Pentane-1,5-diyl)dioxy]bis[(11S,11aS,2R)-10-(2,2,2-trichloroethoxycarbonyl)-11-(tert-butyldimethylsilyloxy)-7-methoxy-2-hydroxyacetyl-1,2,3,10,11,11a-hexahydro-5H-pyrrolo[2,1-[1,4]benzodiazepin-5-one]] (41)

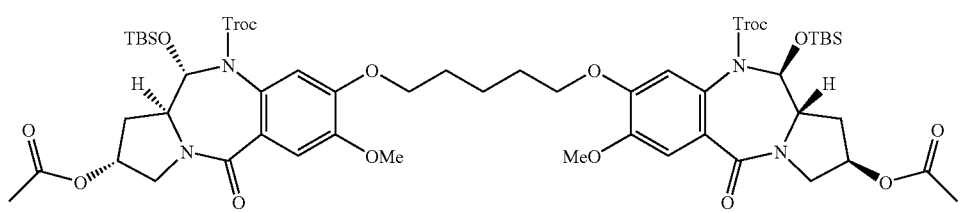

TBSOTf (1.27 mL, 1.47 g, 5.54 mmol) was added to a stirred solution of bis-alcohol 40 (1.96 g, 1.85 mmol) and 2,6-lutidine (0.86 mL, 0.79 g, 7.39 mmol) in dry DCM (40 mL). The reaction mixture was allowed to stir under a $N_2$ atmosphere for 5 hours after which time TLC (EtOAc) revealed consumption of starting material. Following dilution with DCM (50 mL), the organic mixture was washed with saturated $CuSO_4$ (30 mL), saturated $NaHCO_3$ (30 mL), brine (50 mL) and dried ($MgSO_4$). Filtration and evaporation of the solvent in vacuo afforded the crude product which was purified by flash column chromatography (40:60 v/v Hexane/EtOAc) to provide the product 41 as a white glass (1.31 g, 55%): $^1$H NMR (400 MHz, $CDCl_3$) δ 7.27 (s, 2H), 6.72 (s, 2H), 5.76 (d, 2H, J=9.0 Hz), 5.37 (br s, 2H), 5.24 (d, 2H, J=12.1 Hz), 4.17 (d, 2H, J=12.1 Hz), 4.14-3.96 (m, 6H), 3.93 (s, 6H), 3.75-3.66 (m, 4H), 2.40-2.33 (m, 2H), 2.28-2.18 (m, 2H), 2.04 (s, 6H), 1.98-1.90 (m, 4H), 1.69-1.62 (m, 2H), 0.86 (s, 18H), 0.23 and 0.22 (s×2, 12H); $^{13}$C NMR (100 MHz, $CDCl_3$) δ 170.4, 168.0, 153.6, 150.5, 149.1, 127.9, 125.3, 113.9, 110.7, 95.2, 88.2, 74.7, 71.7, 68.7, 60.5, 56.2, 51.2, 36.3, 28.7, 25.6, 22.7, 21.1, 17.8, −4.2 and −5.2.

(g) 1,1'-[[(Pentane-1,5-diyl)dioxy]bis[(11S,11aS,2R)-10-(2,2,2-trichloroethoxycarbonyl)-11-(tert-butyldimethylsilyloxy)-7-methoxy-2-hydroxy-1,2,3,10,11,11a-hexahydro-5H-pyrrolo[2,1-c][1,4]benzodiazepin-5-one]] (42)

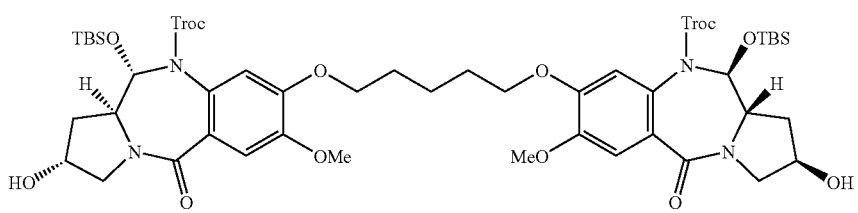

A solution of $K_2CO_3$ (685 mg, 4.96 mmol) in $H_2O$ (15 mL) was added to a stirred solution of acetate compound 41 (1.28 g, 0.99 mmol) in MeOH (15 mL). The initial colourless solution eventually turned yellow and the formation of a white precipitate was observed. The reaction mixture was heated at reflux for 5 hours at which point TLC (EtOAc) revealed complete conversion of starting material to product. Excess solvent was removed by rotary evaporation and the mixture was carefully neutralized with 1N HCl to pH 7. The resulting mixture was extracted with DCM (5×20 mL) and the combined organic layers were then washed with brine (50 mL) and dried ($MgSO_4$). Filtration followed by removal of the solvent by evaporation in vacuo afforded the product 42 as a white solid (982 mg, 82%): $^1$H NMR (400 MHz, $CDCl_3$) δ 7.19 (s, 2H), 6.72 (s, 2H), 5.75 (d, 2H, J=9.0 Hz), 5.22 (d, 2H, J=12.0 Hz), 4.58-4.56 (m, 2H), 4.18 (d, 2H, J=12.0 Hz), 4.11-3.95 (m, 6H), 3.85 (s, 6H), 3.75-3.69 (m, 2H), 3.59 (dd, 2H, J=12.7, 4.2 Hz), 2.55 (br s, 2H), 2.38-2.25 (m, 2H), 2.14-2.03 (m, 2H), 1.97-1.85 (m, 4H), 1.74-1.62 (m, 2H), 0.86 (s, 18H), 0.22 and 0.21 (s×2, 12H); $^{13}$C NMR (100 MHz, $CDCl_3$) δ 168.5, 153.6, 150.6, 149.1, 127.9, 125.3, 114.0, 110.8, 95.3, 88.3, 74.7, 69.5, 68.8, 60.8, 56.0, 54.0, 38.8, 28.8, 25.6, 22.7, 17.8, −4.2 and −5.2.

(h) 1,1'-[[(Pentane-1,5-diyl)dioxy]bis[(11S,11 aS)-10-(2,2,2-trichloroethoxycarbonyl)-11-(tert-butyldimethylsilyloxy)-7-methoxy-2-oxo-1,2,3,10,11,11a-hexahydro-5H-pyrrolo[2,1-c][1,4]benzodiazepin-5-one]] (43)

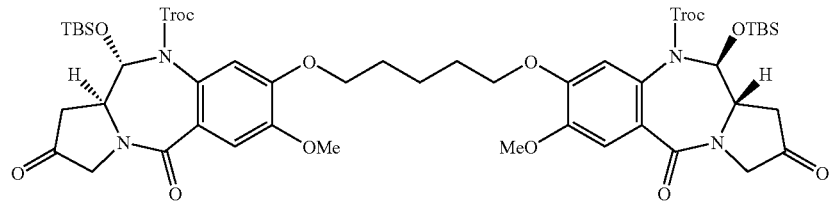

A solution of anhydrous DMSO (0.34 mL, 0.37 g, 4.78 mmol) in dry DCM (4 mL) was added dropwise over a period of 5 minutes to a stirred solution of oxalyl chloride (1.20 mL of a 2M solution in DCM, 2.39 mmol) under a nitrogen atmosphere at −60° C. (liq N$_2$/CHCl$_3$). After stirring at −55° C. for 15 minutes, a slurry of the substrate 42 (962 mg, 0.80 mmol) in dry DCM (8 mL) was added dropwise over a period of 10 minutes to the reaction mixture. After stirring for a further 1 h at −55° C., a solution of TEA (1.56 mL, 1.13 g; 11.2 mmol) in dry DCM (4 mL) was added dropwise over a period of 5 minutes to the reaction mixture. The reaction mixture was allowed to warm to 0° C. and then diluted with DCM (50 mL). The organic solution was washed with cold 1N HCl (20 mL), H$_2$O (20 mL), brine (30 mL) and dried (MgSO$_4$). Filtration and evaporation of the solvent in vacuo afforded the crude product which was purified by flash column chromatography (50:50 v/v Hexane/EtOAc) to afford bis-ketone 43 as a foam (550 mg, 57%): $^1$H NMR (400 MHz, CDCl$_3$) δ 7.25 (s, 2H), 6.76 (s, 2H), 5.82 (d, 2H, J=9.3 Hz), 5.22 (d, 2H, J=12.0 Hz), 4.32 (d, 2H, J=20.4 Hz), 4.22 (d, 2H, J=12.0 Hz), 4.17-4.08 (m, 4H), 4.03-3.89 (m, 10H), 2.96 (dd, 2H, J=19.6, 10.2 Hz), 2.56 (dd, 2H, J=19.6, 2.8 Hz), 1.99-1.92 (m, 4H), 1.72-1.64 (m, 2H), 0.86 (s, 18H), 0.24 and 0.23 (s×2, 12H); $^{13}$C NMR (100 MHz, CDCl$_3$) δ 207.7, 168.0, 153.8, 151.0, 149.5, 127.9, 124.4, 114.1, 110.8, 95.2, 87.5, 74.8, 68.8, 58.9, 56.2, 52.9, 40.4, 28.7, 25.6, 22.8 17.8, −4.12 and −5.31.

(i) 1,1'-[[(Pentane-1,5-diyl)dioxy]bis[(11S,11 aS)-10-(2,2,2-trichloroethoxycarbonyl)-11-(tert-butyldimethylsilyloxy)-7-methoxy-2-[[(trifluoromethyl)sulfonyl]oxy]-1,10,11,11a-tetrahydro-5H-pyrrolo[2,1-c][1,4]benzodiazepin-5-one]] (44)

Anhydrous triflic anhydride taken from a freshly opened ampoule (1.61 mL, 2.71 g, 9.60 mmol) was added rapidly in one portion to a vigorously stirred solution of ketone 43 (525 mg, 0.44 mmol) and anhydrous pyridine (0.78 mL, 759 mg, 9.60 mmol) in dry DCM (25 mL) at 0-5° C. (ice) under a nitrogen atmosphere. The reaction mixture was immediately allowed to warm to room temperature and eventually turned a dark red colour. The reaction mixture was allowed to stir for a total of 28 hours at which point TLC (80:20 v/v EtOAc/hexane) revealed the complete consumption of starting material. The mixture was poured into cold saturated NaHCO$_3$ (50 mL) and extracted with DCM (3×20 mL). The combined organic layers were then washed with saturated CuSO$_4$ (30 mL), brine (30 mL) and dried (MgSO$_4$). Filtration and evaporation of the solvent in vacuo afforded the crude product which was purified by flash column chromatography (80:20 v/v Hexane/EtOAc) to afford triflate 44 as a yellow foam (249 mg, 39%): $^1$H NMR (400 MHz, CDCl$_3$) δ 7.23 (s, 2H), 7.17 (s, 2H), 6.73 (s, 2H), 5.93 (d, 2H, J=8.9 Hz), 5.22 (d, 2H, J=12.1 Hz), 4.21 (d, 2H, J=12.0 Hz), 4.15-4.07 (m, 2H), 4.02-3.86 (m, 8H), 3.33 (ddd, 2H, J=16.6, 10.7, 2.3 Hz), 2.82 (dd, 2H, J=16.7, 2.6 Hz), 1.98-1.91 (m, 4H), 1.71-1.63 (m, 2H), 0.88 (s, 18H), 0.28 and 0.25 (s×2, 12H); $^{13}$C NMR (100 MHz, CDCl$_3$) δ 164.9, 153.6, 151.3, 149.6, 136.0, 127.8, 123.7, 121.0, 118.6 (q, J=321.5 Hz), 114.2, 111.0, 95.1, 86.4, 74.9, 68.8, 60.6, 56.2, 34.4, 28.7, 25.6, 22.8, 17.8, −4.2 and −5.4.

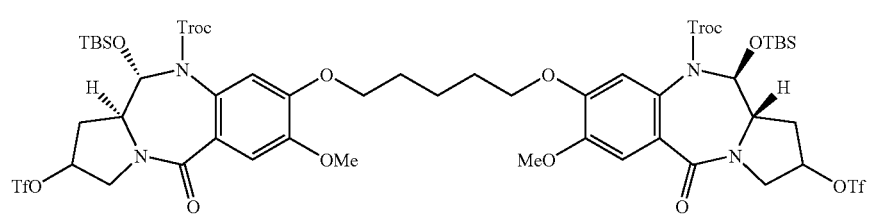

(j) 1,1'-[[(Pentane-1,5-diyl)dioxy]bis[(11S,11aS)-10-(2,2,2-trichloroethoxycarbonyl)-11-(tert-butyldimethylsilyloxy)-7-methoxy-2-(p-methoxyphenyl)-1,10,11,11a-tetrahydro-5H-pyrrolo[2,1-c][1,4]benzodiazepin-5-one]] (45)

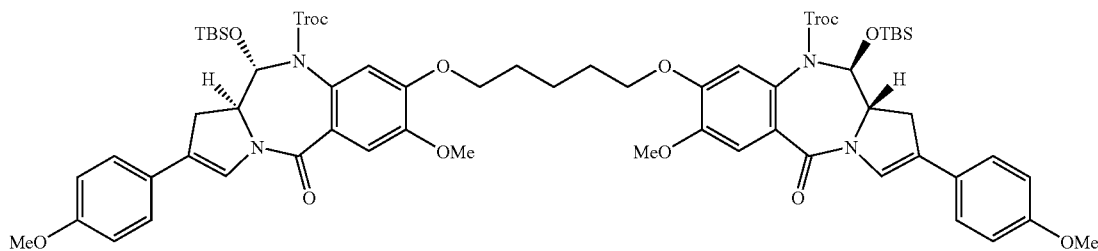

Pd(PPh₃)₄ (7.43 mg, 6.43 μmol) was added to a solution of the triflate 44 (236 mg, 0.16 mmol), 4-methoxyphenylboronic acid (63 mg, 0.42 mmol), TEA (0.13 mL, 98 mg, 0.97 mmol) in H₂O (0.8 mL), EtOH (5 mL) and toluene (5 mL) at room temperature. The reaction mixture was heated in the microwave at 100° C. for 30 minutes after which time TLC (80:20 v/v EtOAc/hexane) revealed the complete consumption of the starting material. Excess solvent was removed by evaporation in vacuo and the resulting residue was dissolved in EtOAc (50 mL), washed with H₂O (20 mL), brine (20 mL) and dried (MgSO₄). Filtration and evaporation of solvent afforded the crude product which was purified by flash column chromatography (gradient elution: 80:20 v/v Hexane/EtOAc to 50:50 v/v Hexane/EtOAc) to afford C2-aryl product 45 as a yellow glass (117 mg, 52%): $^1$H NMR (400 MHz, CDCl₃) δ 7.35 (s, 2H), 7.31 (s, 2H), 7.31-7.27 (m, 6H), 6.90 (d, 4H, J=8.8 Hz), 6.76 (s, 2H), 5.92 (d, 2H, J=8.8 Hz), 5.23 (d, 2H, J=12.0 Hz), 4.20 (d, 2H, J=12.1 Hz), 4.14-4.05 (m, 4H), 4.04-3.95 (m, 2H), 3.93 (s, 6H), 3.83 (s, 6H), 3.34 (ddd, 2H, J=16.3, 10.4, 2.0 Hz), 2.86-2.75 (m, 2H), 2.02-1.94 (m, 4H), 1.72-1.66 (m, 2H), 0.93 and 0.86 (s×2, 18H), 0.28 and 0.25 (s×2, 12H); $^{13}$C NMR (100 MHz, CDCl₃) δ 163.7, 159.1, 153.7, 150.8, 149.3, 127.8, 126.3, 126.1, 125.4, 122.3, 122.2, 114.3, 114.2, 110.9, 95.3, 87.3, 74.8, 68.8, 61.5, 56.2, 55.4, 35.3, 28.8, 25.7, 22.8, 17.9, −4.0 and −5.1.

(k) 1,1'-[[(Pentane-1,5-diyl)dioxy]bis[(11aS)-7-methoxy-2-(p-methoxyphenyl)-1,11a-dihydro-5H-pyrrolo[2,1-[1,4]benzodiazepine-5-one]] (46)

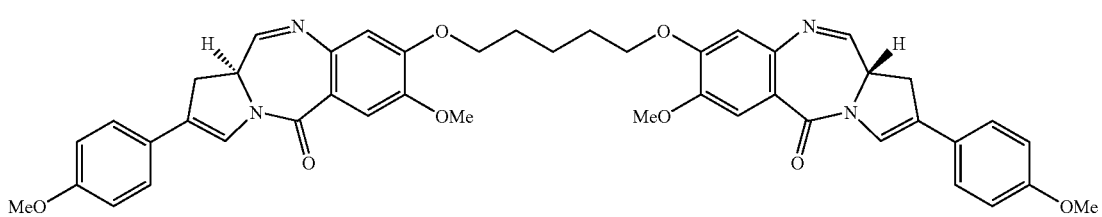

10% Cd/Pb couple (192 mg, 1.55 mmol) was added to a rapidly stirring mixture of 45 (107 mg, 77.3 μmol), THF (2.5 mL) and 1N NH₄OAc (2.5 mL). The reaction mixture was allowed to stir for 3 hours at which point TLC (95:5 v/v CHCl₃/MeOH) showed the formation of desired PBD accompanied by side-products. The solids were collected by filtration and rinsed with H₂O and DCM. The aqueous layer was extracted with DCM (3×10 mL) and the organic extracts were combined, washed with brine (50 mL) and dried (MgSO₄). Filtration and evaporation of solvent afforded the crude product which was purified by flash column chromatography (gradient elution: CHCl₃ to 99:1 v/v CHCl₃/MeOH) to afford the imine 46 as a yellow glass (32.5 mg, 55%): $^1$H NMR (400 MHz, CDCl₃) δ 7.89 (d, 2H, J=3.9 Hz), 7.53 (s, 2H), 7.39 (s, 2H), 7.34 (d, 4H, J=8.8 Hz), 6.90 (d, 4H, J=8.8 Hz), 6.82 (s, 2H), 4.43-4.38 (m, 2H), 4.18-4.05 (m, 4H), 3.95 (s, 6H), 3.83 (s, 6H), 3.58 (ddd, 2H, J=16.2, 11.5, 1.9 Hz), 3.38 (ddd, 2H, J=16.3, 5.1, 1.6 Hz), 2.01-1.94 (m, 4H), 1.73-1.66 (m, 2H); $^{13}$C NMR (100 MHz, CDCl₃) δ 162.6, 161.3, 159.2, 151.3, 148.1, 140.3, 126.2, 126.0 (×2), 123.2, 122.0, 119.1, 114.3, 111.9, 110.9, 68.8, 56.2, 55.4, 53.9, 35.6, 28.7, 22.6.

(j) 1,1'-[[(Pentane-1,5-diyl)dioxy]bis[(11aS)-11-sulpho-7-methoxy-2-(p-methoxyphenyl)-1,10,11,11a-tetrahydro-5H-pyrrolo[2,1-c][1,4]benzodiazepin-5-one]] sodium salt (47)

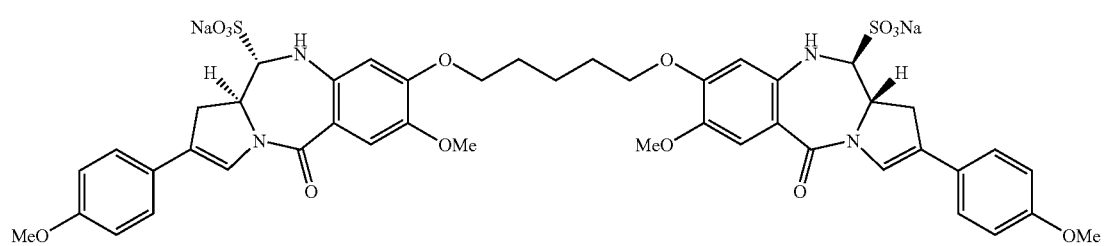

A solution of sodium bisulphite (4.90 mg, 47.2 μmol) in water (3 mL) was added to a stirred solution of 46 (18.11 mg, 23.6 μmol) in dichloromethane (1.5 mL). The reaction mixture was allowed to stir vigorously for 24 hours, after which time the organic and aqueous layers were separated. TLC analysis (95:5 v/v $CHCl_3$/MeOH) of the aqueous phase revealed absence of 46 ($R_f$~0.3) and the presence of baseline material with strong UV-absorption. The aqueous layer was lyophilised to provide the bisulphite adduct 47 as a light-weight solid (10 mg, 43%): $^1$H NMR (400 MHz, DMSO-$d_6$) δ 7.41 (s, 2H), 7.37 (d, 4H, J=8.7 Hz), 7.04 (s, 2H), 6.91 (d, 4H, J=8.9 Hz), 6.47 (s, 2H), 5.24 (s, 2H), 4.31-4.21 (m, 2H), 4.06-3.86 (m, 6H), 3.76 (s, 6H), 3.71 (s, 6H), 3.51-3.21 (m, 4H), 1.90-1.70 (m, 4H), 1.62-1.51 (m, 2H).

Example 9

Determination of In Vitro Cytotoxicity

K562 Cell Line (MTT Assay)
1 Hour Exposure
K562 human chronic myeloid leukaemia cells were maintained in RPM1 1640 medium supplemented with 10% fetal calf serum and 2 mM glutamine at 37° C. in a humidified atmosphere containing 5% $CO_2$ and were incubated with a specified dose of drug for 1 hour at 37° C. in the dark. The incubation was terminated by centrifugation (5 min, 300 g) and the cells were washed once with drug-free medium. Following the appropriate drug treatment, the cells were transferred to 96-well microtiter plates ($10^4$ cells per well, 8 wells per sample). Plates were then kept in the dark at 37° C. in a humidified atmosphere containing 5% $CO_2$. The assay is based on the ability of viable cells to reduce a yellow soluble tetrazolium salt, 3-(4,5-dimethylthiazol-2-yl)-2,5-diphenyl-2H-tetrazolium bromide (MTT, Aldrich-Sigma), to an insoluble purple formazan precipitate. Following incubation of the plates for 4 days (to allow control cells to increase in number by approximately 10 fold), 20 μL of MTT solution (5 mg/mL in phosphate-buffered saline) was added to each well and the plates further incubated for 5 h. The plates were then centrifuged for 5 min at 300 g and the bulk of the medium pipetted from the cell pellet leaving 10-20 μL per well. DMSO (200 μL) was added to each well and the samples agitated to ensure complete mixing. The optical density was then read at a wavelength of 550 nm on a Titertek Multiscan ELISA plate reader, and a dose-response curve was constructed. For each curve, an $IC_{50}$ value was read as the dose required to reduce the final optical density to 50% of the control value.

96 Hour Exposure
In a modification of the above method, $5 \times 10^4$ K562 cells (as above) were maintained in RPMI 1640 medium (Sigma) supplemented with 10% foetal calf serum (Sigma) and 20 mM L-glutamine (Sigma) and 190 μL of this solution incubated with specific doses of the drug (10 μL) for 96 hours at 37° C. in 5% $CO_2$. 250 μg/ml (final) MTT was added to each well and the plates incubated for a further 4 hours. Absorbance was read at 450 nm using an Envision plate reader (Applied Biosystems). Data was then analysed by Graphpad PRISM, and an $IC_{50}$ obtained (defined as the compound concentration needed to reduce the cell population by half).
Results

| Compound | $IC_{50}$ (μM) |
|---|---|
| ZC-207 | 0.0053[a] |
| ZC-423 | 0.0015[b] |

[a] 1 hour incubation
[b] 96 hour incubation

K562 Cell Line (Alamar Blue Assay)
The compounds to be tested were dissolved in 100% Biotech grade DMSO (Sigma) and subsequently diluted to stock concentrations of either 2 μM or 200 nM in 2% DMSO. 100 μl of the stock concentrations were serially diluted 1 in 3 in 2% DMSO in intermediate polystyrene 96 well cell culture plates (Nunc). 2% DMSO was placed in the outer columns for use as blanks, and in the $2^{nd}$ or $11^{th}$ column (depending on whether the top or bottom of an assay plate was to be used) for use as a control. The entire row of the intermediate plate was then transferred in triplicate to either rows B to D or E to G of a fluorescence compatible polystyrene 96 well cell culture plate (Greiner BioOne); 10 μl to each well. A cell solution containing $5 \times 10^4$ cells/ml was made up in phenol red free RPMI 1640 (Sigma) supplemented with 10% foetal calf serum (Sigma) and 20 mM L-glutamine (Sigma). 190 μl cell solution was added to each well of the assay plate, from columns 2 to 11. 190 μl culture media was added to columns 1 and 12. Plates were incubated for 96 hours at 37° C. in 5% $CO_2$. 1 μM (final) rezasurin (converted to fluorescent resofurin by viable cells) was added to each well and the plates incubated for a further 4 hours. Fluorescence was read at 530-570 nm excitation, 580-620 nm emission using an Envision plate reader (Applied Biosystems). Data was then analysed by Graphpad PRISM, and an $IC_{50}$ obtained (defined as the compound concentration needed to reduce the cell population by half).

Results

| Compound | IC$_{50}$ (nM) |
|---|---|
| 19 | <1 |
| 22 | <1 |
| 26 | <1 |
| 27 | <1 |
| 29 | <1 |
| 30 | <1 |
| 32 | <1 |
| 33 | <1 |

LOXIMVI and OVCAR-5 Cell Lines

A cell solution containing 5×10$^4$ cells/ml of either LOX-IMVI human melanoma cells or OVCAR-5 human ovarian tumour cells was made up in phenol red free RPMI 1640 (Sigma) supplemented with 10% foetal calf serum (Sigma) and 20 mM L-glutamine (Sigma). 190 µl cell solution was added to each well of a fluorescence compatible polystyrene 96 well cell culture plate (Greiner BioOne), from columns 2 to 11. 190 µl culture media was added to columns 1 and 12. Plates were incubated overnight at 37° C. in 5% CO$_2$. Compounds were dissolved in 100% Biotech grade DMSO (Sigma) and subsequently diluted to stock concentrations in 2% DMSO. 100 µl of the stock concentrations were serially diluted 1 in 3 in 2% DMSO in intermediate polystyrene 96 well cell culture plates (Nunc). 2% DMSO was placed in the outer columns for use as blanks, and in the 2$^{nd}$ or 11$^{th}$ column (depending on whether the top or bottom of an assay plate was to be used) for use as a control. The entire row of the intermediate plate was then transferred in triplicate, 10 µl per well, to either rows B to D or E to G of the cell plate. Plates were incubated for 96 hours at 37° C. in 5% CO$_2$ 1 µM (final) rezasurin (converted to fluorescent resofurin by viable cells) was added to each well and the plates incubated for a further 4 hours. Fluorescence was read at 530-570 nm excitation, 580-620 nm emission using an Envision plate reader (Applied Biosystems). Data was then analysed by Graphpad PRISM, and an IC$_{50}$ obtained (defined as the compound concentration needed to reduce the cell population by half).

Results

| Cell line | ZC-423 IC$_{50}$ (nM) |
|---|---|
| LOXIMVI | 4.83 |
| OVCAR-5 | 5.2 |

Example 10

Anti Tumour Activity

The following experiments was carried out under a project licence approved by the Home Office, London, UK, and UK CCCR guidelines (Workman, P., et al., *British Journal of Cancer*, 77, 1-10 (1998)) were followed throughout.

LOX IMVI (human melanomas) were grown subcutaneously in nude mice (B&K Universal, Hull, UK). Tumours were transplanted as single tumour fragments in the flank by trocar. Groups of 8 tumour-bearing mice were treated with ZC423 at the previously established single intravenous (iv) maximum tolerated dose (MTD) of 3 mgkg$^{-1}$ using 5% DMA/saline as the vehicle. Control mice (n=8) were treated with vehicle alone.

Treatment commenced when tumours could be reliably measured by calipers (mean dimensions 4×4 mm) and therapeutic effects were assessed by daily caliper measurements of the tumour and mouse weights. Tumour volumes were determined by the formula $a^2 \times b/2$ where a is the smaller and b is the larger diameter of the tumour. The results are shown in FIG. 1 as a graphs of relative tumour volume against time (■ ZC423; ♦ Control—solvent alone). The activity of ZC423 was shown to be statistically significant when assessed by Mann-Whitney analysis (as described, for example, in Essential Statistics 2$^{nd}$ Edition (1989), D. G. Rees, ISBN 0 412 32030 4, Chapman and Hall, London).

Figure 2:
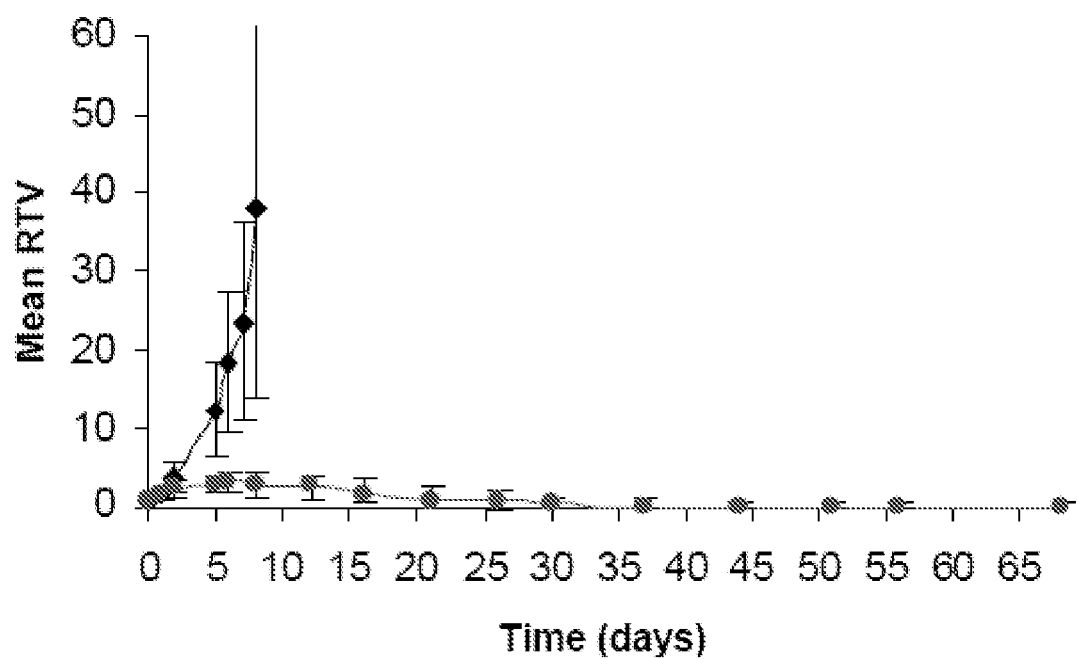
FIG. 2 is a graph of relative tumour volume (RTV) versus time during treatment of mice bearing LOX IMVI (human melanoma) with ZC423, with results presented over a longer period of time.

FIG. 2 shows the results of the same test (● ZC423; ♦ Control—solvent alone) but extended over a longer period, and with a larger scale for the Mean RTV. The control group was ceased at 16 days, at which point there were no tumour free mice, compared to the treated group where all animals were tumour free at 68 days.

Figure 3:
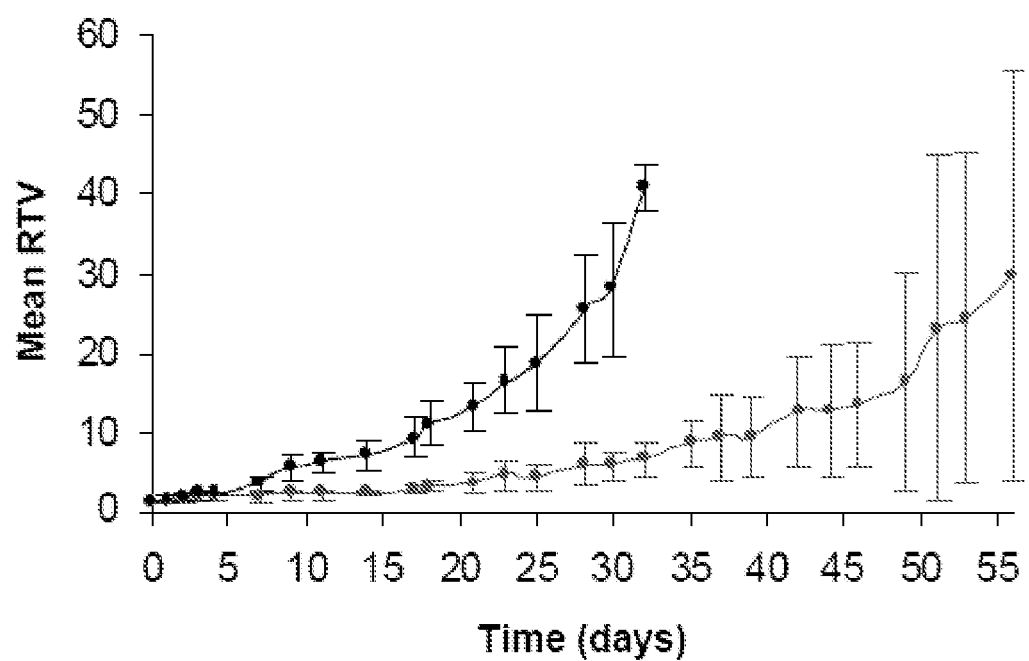
FIG. 3 is a graph of relative tumour volume (RTV) versus time during treatment of mice bearing OVCAR-5 (human ovarian tumour) with ZC423.

A study was carried out using OVCAR-5 (human ovarian tumours) under the same conditions as described above. The results are shown in FIG. 3 (● ZC423; ♦ Control—solvent alone). In this study the control group was ceased at 32 days.

Example 11

Cross-Linking and Solubility

DNA Cross-Linking

Closed-circular puc18 DNA was linearized with HindIII, then dephosphorylated, and finally 5' end labeled with [y32P]-ATP using polynucleotide kinase. Reactions containing 10 ng of DNA and drug were carried out in aqueous 1×TEOA (25 mM triethanolamine, 1 mM EDTA, pH 7.2) buffer at a final volume of 50 µL at 37° C. Reactions were terminated by addition of an equal volume of stop solution (0.6 M NaOAc, 20 mM EDTA, 100 µg/mL tRNA) followed by precipitation with ethanol. Following centrifugation of the samples, the supernatants were discarded and the pellets were dried by lyophilization. Samples were resuspended in 10 µL of alkaline denaturing buffer (4 mg bromophenol blue, 600 mg sucrose and 40 mg NaOH) and vortexed for three minutes at room temperature. The non-denatured controls were re-suspended in 10 µL of standard sucrose loading dye (2.5 mg bromophenol blue, 2.5 mg xylene cyanol blue and 4 g sucrose). Both samples and controls were loaded directly onto an agarose gel.

Electrophoresis was performed on a 0.8% submerged horizontal agarose gel, 20 cm in length for 16 hours at 38-40 V in 1×TAE running buffer (2.42 g Tris Base, 0.372 g EDTA, 0.571 ml glacial acetic acid). Gels were dried under vacuum for 80 minutes at 80° C. on a Savant SG210D SpeedGel gel dryer onto one layer of Whatman 3MM with a layer of DE81 filter paper underneath. An autoradiograph was obtained, after overnight exposure onto FujiRX x-ray film. The film bands were quantitated using a BioRad GS-670 imaging laser densitometer. The percentage of cross-linking was calculated by measuring the total DNA in each lane (the sum of the densities for the double-stranded and single-stranded bands) relative to the amount of density of double-stranded band alone. A dose response curve was derived by plotting drug concentration against the determined percentage level of cross-linked DNA, from which was derived the amount required to cross-link 50% of the DNA (XL$_{50}$).

Solubility

Solubility was determined by dissolving the test compound in the minimum amount of water to produce a saturated solution.

Results

DNA Cross-linking

| Compound | IC$_{50}$ (µM) |
|---|---|
| 18 | 0.2 |
| 19 | 2 |
| 21 | 0.5 |
| 22 | 0.3 |

Solubility

| Compound | Amount of compound (g) in 1 L water |
|---|---|
| ZC-207 | Insoluble |
| ZC-423 | 11 |
| 27 | 9 |
| 30 | 4 |
| 33 | 3 |

The invention claimed is:

1. A compound of formula:

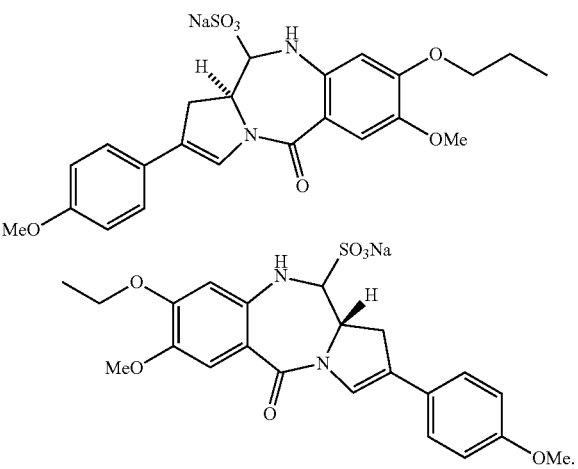

2. A pharmaceutical composition comprising a compound according to claim 1, and a pharmaceutical excipient.

3. A method of treating a proliferative disease comprising administering a therapeutically effective amount of a compound according to claim 1, wherein the proliferative disease is selected from the group consisting of leukemia, melanoma, and ovarian cancer.

* * * * *